US009684771B2

(12) United States Patent
Cope et al.

(10) Patent No.: US 9,684,771 B2
(45) Date of Patent: Jun. 20, 2017

(54) METHODS, SYSTEMS, AND SOFTWARE FOR IDENTIFYING BIO-MOLECULES USING MODELS OF MULTIPLICATIVE FORM

(71) Applicant: Codexis, Inc., Redwood City, CA (US)

(72) Inventors: Gregory Allan Cope, Menlo Park, CA (US); Nicholas John Agard, San Francisco, CA (US)

(73) Assignee: Codexis, Inc., Redwood City, CA (US)

( * ) Notice: Subject to any disclaimer, the term of this patent is extended or adjusted under 35 U.S.C. 154(b) by 92 days.

(21) Appl. No.: 14/167,713

(22) Filed: Jan. 29, 2014

(65) Prior Publication Data

US 2014/0221216 A1    Aug. 7, 2014

Related U.S. Application Data

(60) Provisional application No. 61/799,377, filed on Mar. 15, 2013, provisional application No. 61/759,276, filed on Jan. 31, 2013.

(51) Int. Cl.

| | |
|---|---|
| *G01N 33/48* | (2006.01) |
| *G06F 19/00* | (2011.01) |
| *G06F 19/12* | (2011.01) |
| *G06F 19/16* | (2011.01) |
| *G06F 19/18* | (2011.01) |
| *G06G 7/58* | (2006.01) |
| *C40B 50/02* | (2006.01) |

(52) U.S. Cl.
CPC ............ *G06F 19/701* (2013.01); *G06F 19/12* (2013.01); *G06F 19/16* (2013.01); *G06F 19/18* (2013.01); *C40B 50/02* (2013.01)

(58) Field of Classification Search
CPC ........... G06F 19/18; G06F 19/22; G06F 19/24
See application file for complete search history.

(56) References Cited

U.S. PATENT DOCUMENTS

| | | | |
|---|---|---|---|
| 6,117,679 | A | 9/2000 | Stemmer |
| 6,171,820 | B1 | 1/2001 | Short |
| 6,376,246 | B1 | 4/2002 | Crameri et al. |
| 6,537,776 | B1 | 3/2003 | Short |
| 6,586,182 | B1 | 7/2003 | Patten et al. |
| 6,605,449 | B1 | 8/2003 | Short |
| 7,315,786 | B2 | 1/2008 | Dahiyat et al. |
| 7,747,391 | B2 | 6/2010 | Gustafsson et al. |
| 7,747,393 | B2 | 6/2010 | Fox |
| 7,751,986 | B2 | 7/2010 | Gustafsson et al. |
| 7,783,428 | B2 | 8/2010 | Gustafsson et al. |
| 8,762,066 | B2 | 6/2014 | Fox |
| 2002/0045175 | A1 | 4/2002 | Wang et al. |
| 2002/0048772 | A1 | 4/2002 | Dahiyat et al. |
| 2002/0155460 | A1 | 10/2002 | Schellenberger et al. |
| 2004/0161796 | A1 | 8/2004 | Gustafsson et al. |
| 2005/0084907 | A1 | 4/2005 | Fox |
| 2007/0239364 | A1 | 10/2007 | Fox |
| 2008/0132416 | A1 | 6/2008 | Fox |
| 2008/0147369 | A1 | 6/2008 | Fox |
| 2009/0312196 | A1 | 12/2009 | Colbeck et al. |
| 2010/0004135 | A1 | 1/2010 | Fox |
| 2010/0004136 | A1 | 1/2010 | Fox |
| 2010/0005047 | A1 | 1/2010 | Fox |
| 2011/0257023 | A1 | 10/2011 | Gustafsson et al. |
| 2013/0017540 | A1 | 1/2013 | Yen et al. |
| 2014/0214391 | A1 | 7/2014 | Cope et al. |
| 2014/0249035 | A1 | 9/2014 | Fox |
| 2015/0065357 | A1 | 3/2015 | Fox |

FOREIGN PATENT DOCUMENTS

| | | |
|---|---|---|
| CN | 101855242 A | 10/2010 |
| JP | 2004-068729 A | 3/2004 |
| JP | 2005-519384 | 6/2005 |
| JP | 2008-503589 A | 2/2008 |
| WO | WO 03/055978 | 7/2003 |
| WO | 03/075129 | 9/2003 |
| WO | WO 03/085548 | 10/2003 |

(Continued)

OTHER PUBLICATIONS

U.S. Appl. No. 14/256,692, filed Apr. 18, 2014, Fox.
US Notice of Allowance (Notice of Allowability) dated Apr. 17, 2014 issued in U.S. Appl. No. 11/981,578.
US Notice of Allowance dated May 30, 2014 issued in U.S. Appl. No. 11/981,578.
PCT International Preliminary Report on Patentability and Written Opinion dated Dec. 28, 2006 issued in PCT/US2005/022119.
PCT International Search Report and Written Opinion dated May 20, 2014 issued in PCT/US14/13666.
PCT International Search Report and Written Opinion dated Apr. 23, 2014 issued in PCT/US14/13668.
Abecassis et al., (2000) "High Efficiency Family Shuffling Based on Multi-Step PCR and in vivo DNA Recombination in Yeast: Statistical and Functional Analysis of a Combinatorial Library Between Human Cytochrome P460 1A1 and 1A2," *Nucleic Acids Res.*, 28:E88.

(Continued)

*Primary Examiner* — Eric S Dejong
(74) *Attorney, Agent, or Firm* — Weaver Austin Villeneuve & Sampson LLP

(57) ABSTRACT

The present invention provides methods for identifying bio-molecules with desired properties, or which are most suitable for acquiring such properties, from complex bio-molecule libraries or sets of such libraries. More specifically, some embodiments of the present invention provide methods for building sequence-activity models comprising multiplicative terms and using the models to guide directed evolution. In some embodiments, the sequence-activity models include one or more interaction terms, each of which including an interaction coefficient representing the contribution to activity of two or more defined residues. In some embodiments, the models describe relation between protein or nucleic acid sequences and protein activities. In some embodiments, the present invention also provides methods for preparing sequence-activity models, including but not limited to stepwise addition or subtraction techniques, Bayesian regression, ensemble regression and other methods. The present invention further provides digital systems and software for performing the methods provided herein.

37 Claims, 22 Drawing Sheets

(56) References Cited

FOREIGN PATENT DOCUMENTS

| WO | 2006/002267 | 1/2006 |
|---|---|---|
| WO | WO 2012/061585 | 5/2012 |
| WO | WO 2012/093483 | 7/2012 |
| WO | WO 2014/120819 | 8/2014 |
| WO | WO 2014/120821 | 8/2014 |

OTHER PUBLICATIONS

Adenot et al., (1999) "Peptides Quantitative Structure-Function Relationships: An Automated Mutation Strategy to Design Peptides and Pseudopeptides from Substitution Matrices," *Journal of Molecular Graphics and Modelling*, 17:292-309.
Agrafiotis, D.K., (2001) "Multiobjective Optimization of Combinatorial Libraries", IBM J. Res & Dev., 45(3):545-566.
Aita et al., (2000) "Theory of Evolutionary Molecular Engineering Through Simultaneous Accumulation of Advantageous Mutations," *J. Theor. Biol.*, 207:543-556.
Aita et al., (Accepted Jan. 14, 2000) "Analysis of Local Fitness Landscape with a Model of the Rough Mt. Fuji-Type Landscape: Application to Prolyl Endopeptidase and Thermolysin," *Biopolymers.* 54:64-79.
Aita et al., (2001) "A Cross-Section of the Fitness Landscape of Dihydrofolate Reductase," *Protein Eng*, 14:633-638.
Aita et al., (2002) "Surveying a Local Fitness Landscape of a Protein with Epistatic Altee for the Study of Directed Evolution," *Biopolymers*, 64:95-106.
Benner et al., (1994) "Amino Acid Substitution During Functionally Constrained Divergent Evolution of Protein Sequences," *Protein Engineering*, 7(11):1323-1332.
Benos et al., (2002) "Additivity in Protein-DNA Interactions: How Good an Approximation is it?" *Nucleic Acids Res* 30(20):4442-51.
Bogarad et al., (1999) "A Hierarchical Approach to Protein Molecular Evolution," *Proc Natl Acad Sci USA*, 96:2591-2595.
Bucht et al., (1999) "Optimising the Signal Peptide for Glycosyl Phosphatidylinositol Modification of Human Acetylcholinesterase Using Mutational Analysis and Peptide-Quantitative Structure-Activity Relationships," *Biochimica et Biophysica Acta* 1431:471-482.
Carlsen et al., (2002) "QSAR's Based on Partial Order Ranking," *SAR QSAR Environmental Research*, 13(1):153-165.
Casari et al., (1995) "A Method to Predict Functional Residues in Proteins," *Nat. Struct Biol.*, 2:171-178.
Choulier et al., (2002) "QSAR Studies Applied to the Prediction of Antigen-Antibody Interaction Kinetics as Measured by BIACORE," *Protein Eng*, 15(5):378-382.
Crameri et al., (1998) "DNA Shuffling of a Family of Genes from Diverse Species Accelerates Directed Evolution," *Nature* 391:288-291.
Dahiyat et al., (1996) "Protein Design Automation," *Protein Science* 5:895-903.
Damborsky, Jiri, (1998) "Quantitative Structure-Function and Structure-Stability Relationships of Purposely Modified Proteins," *Protein Engineering*, 11(1):21-30.
Darius et al., (Nov. 1994) "Simulated Molecular Evolution of Computer Generated Artifacts?," *Biophysical Journal*, 67:2120-2122.
del Sol Mesa et al., (2003) "Automatic Methods for Predicting Functionality Important Residues," *J Mol Biol*, 326:1289-1302.
Dill K.A., (1997) "Additivity Principles in Biochemistry," *J Biol Chem*, 272(2):701-704.
Dimmic et al., (2002) "rtREV: An Amino Acid Substitution Matrix for Inference of Retrovirus and Reverse Transcriptase Phylogeny," *J. Mol Evol*, 55:65-73.
Distefano et al., (2002) "Quantifying β-Sheet Stability by Phage Display," *J Mol Biol*, 322(1):179-188.
Dobrynin et al., (1980) "Synthesis of model promoter for gene expression in *Escherichia coli,*" *Nucleic Acid Research*, Symposium Series No. 7 :365-376.

Eriksson et al., (1990) "Peptide QSAR on Substance P Analogues, Enkephalins and Bradykinins Containing $_L$-and $_D$-Amino Acids," *Acta Chemica Scandinavica*, 44:50-56.
Eroshkin et al., (1993) "Algortihm and Computer Program Pro_Anal for Analysis of Relationship Between Structure and Activity in a Family of Proteins or Peptides," *Comput. Appl. Biosci.*, 9(5):491-497.
Eroshkin et al., (1995) "PROANAL version 2: Multifunctional Program for Analysis of Multiple Protein Sequence Alignments and for Studying the Structure-Activity Relationships in Protein Families," *Comput. Appl. Biosci.*, 11(1):39-44.
Fariselli et al., (2001) "Prediction of Contact Maps with Neural Networks and Correlated Mutations," *Protein Eng*, 14(11):835-843.
Fariselli et al., (2002)"Prediction of Protein-Protein Interaction Sites in Heterocomplexes with Neural Networks," *Eur. J. Biochem.*, 269:1356-1361.
Fox et al., (2003) "Optimizing the Search Algorithm for Protein Engineering by Directed Evolution," *Protein Engineering, Oxford Univ Press*, 16(8):589-597.
Geladi et al., (1986) "Partial Least-Squares Regression: A Tutorial," *Analytica Chimica Acta*, 185:1-17.
Glieder et al., (2002) "Laboratory Evolution of a Soluble, Self-Sufficient, Highly Active Alkaline Hydroxylase," *Nat Biotechnol*, 20:1135-1139.
Gogos et al., (2000) "Assignment of Enzyme Substrate Specificity by Principal Component Analysis of Aligned Protein Sequences: An Experimental Test Using DNA Glycosylase Homologs," *Proteins: Structure, Function, and Genetics*, 40:98-105.
Goodacre et al., (2000) "Detection of the Dipicolinic Acid Biomarker in *Bacillus* Spores Using Curie-Point Pyrolysis Mass Spectrometry and Fourier Transform Infrared Spectroscopy," *Anal. Chem.* 72:119-127.
Govindarajan et al., (2003) "Systematic Variation of Amino Acid Substitutions for Stringent Assessment of Pairwise Covariation," *J. Mol. Biol*, 328:1061-1069.
Gunn, Steve R., (May 10, 1998) "Support Vector Machines for Classification and Regression," *Technical Report, Department of Electronics and Computer Science, University of Southampton*, 65 pages.
Hanes et al., (May 1997)"In vitro selection and evolution of functional proteins by using ribosomes display," *Proc. Natl. Acad. Sci. USA*, 94:4937-4942.
Hayes et al., (2002) "Combining Computational and Experimental Screening for Rapid Optimization of Protein Properties," *Proc Natl Acad Sci USA*, 99(25):15926-15931.
Hellberg et al., (1986) "A Multivariate Approach to QSAR," Ph.D. Thesis, Department of Organic Chemistry, Research Group for Chemometrics, University of Umea, Sweden, 198 pages.
Hellberg et al., (1988) "The Prediction of Bradykinin Potentiating Potency of Pentapeptides. An Example of a Peptide Quantitative Structure-Activity Relationship," *Acia Chemica Scandinaviea B* 40:135-140.
Hellberg et al., (1991) "Minimum Analogue Peptide Sets (MAPS) for Quantitative Structure-Activity Relationships," *Int J Pept Protein Res*, 37:414-424.
Holowachuk et al., (1995) "Efficient Gene Synthesis by Klenow Assembly/Extension-*Pfu* Polymerase Amplification (KAPPA) of Overlapping Olingonucleotides," *PCR Methods Appl*, 4:299-302.
Hoover et al., (2002) "DNAWorks: An Automated Method for Designing Oligonucleotides for PCR-Based Gene Synthesis," *Nucleic Acids Res*, 30(10):e43.
Ivanisenko et al., (1997) "Search for Sites With Functionally Important Substitutions in Sets of Related or Mutant Protein," *Molecular Biology* 31(5):749-755. *Translated from Molekulyarnaya Biologiya*, 31(5):880-887.
Johnson et al., (1997) "The Traveling Salesman Problem: A Case Study in Local Optimization," In *Local Search in Combinatorial Optimization*, Edited by Aarts et al., John Wiley & Sons Ltd., 216-310.
Jonsson et al., (1993) "Quantitative Sequence-Activity Models (QSAM)—Tools for Sequence Design," *Nucleic Acids Res.*, 21(3):733-739.

(56) References Cited

OTHER PUBLICATIONS

Kell, D.B., (2002) "Metabolomics and Machine Learning: Explanatory Analysis of Complex Metabolome Data Using Genetic Programming to Produce Simple, Robust Rules," *Molecular Biology Reports*, 29(1-2):237-241.

Koshi et al., (1995) "Context-Dependent Optimal Substitution Matrices," *Protein Eng*, 8(7):641-645.

Koshi et al., (1997) "Mutation Matrices and Physical-Chemical Properties: Correlations and Implications," *Proteins* 27(3):336-344.

Krogh, Anders (1998) "An Introduction to Hidden Markov Models for Biological Sequences," *Chapter 4 in Computational Methods in Molecular Biology*, edited by S.L. Salzberg, D.B. Searls and S. Kasif, pp. 45-63.

Kwasigroch et al., (2002) "PoPMuSiC, Rationally Designing Point Mutations in Protein Structures," *Bioinformatics*, 18(12):1701-1702.

Lahr et al., (1999) "Patterned Library Analysis: A Method for the Quantitative Assessment of Hypotheses Concerning the Determinants of Protein Structure," *Proc Natl Acad Sci USA*, 96(26):14860-14865.

Lapinsh et al., (2001) "Classification of G-Protein Coupled Receptors by Alignment Independent Extraction of Principal Chemical Properties of Primary Amino Acid Sequences," *Protein Sci* 11(4):795-805.

Lapinsh et al., (2001) "Development of Proteo-Chemometrics: A Novel Technology for the Analysis of Drug-Receptor Interactions," *Biochim Biophys Acata*, 1525(1-2):180-190.

Lapinsh et al., (2002) "Protechemometrics Modeling of the Interaction of Amine G-Protein Coupled Receptors with a Diverse Set of Ligands," *Mol Pharmacol* 61(6):1465-1475.

Lapinsh et al., (2003) "QSAR and Proteo-Chemometric Analysis of the Interaction of a Series of Organic Compounds with Melanocortin Receptor Subtypes," *J Med Chem*, 46(13):2572-2579.

Lathrop R.H., (1994) "The protein threading problems with sequence amino acids interaction preference is NP-complete," *Protein Eng.*, 7(9):1059-1068.

Lathrop et al., (1996) "Global Optimum Protein Threading with Gapped Alignment and Empirical Pair Score Functions," *J. Mol. Biol.*, 255:641-665.

Lee et al., (2000) "Mathematical Modelling of Inset Neuropeptide Potencies. Are Quantitatively Predictive Models Possible?" *Insect Biochem Mol Biol*, 30(10):899-907.

Lehmann et al., (2000) "Exchanging the Active Site Between Phytases for Altering the Functional Properties of the Enzyme," *Protein Sci*, 9:1866-1872.

Lehmann et al., (2001) "Engineering Proteins Thermostability: the Use of sequence Alignments Versus Rational Design and Directed Evolution," *Current Opinion in Biotechnology* 12:371-375.

Lehmann et al., (2002) "The Consensus Concept for Thermostability Engineering of Proteins: Further Proof of Concept," *Protein Eng.*, 15(5):403-411.

Lin et al., (1999) "Functional Expression of Horseradish Peroxidase in *E. coli* by Directed Evolution," *Biotechnol. Prog*, 15:467-471.

Linusson et al., (2000) "Statistical Molecular Design of Building Blocks for Combinatorial Chemistry," *J Med Chem*, 43(7):1320-1328.

Looger et al., (2003)"Computational Design of Receptor and Sensor Proteins with Novel Functions," *Nature*, 423:185-190.

Lu et al., (2001) "Predicting the Reactivity of Proteins from Their Sequence Alone: Kazal Family of Protein Inhibitors of Serine Proteinases," *Proc Natl Acad Sci USA*, 98(4):1410-1415.

Martin et al., (1995) "Measuring Diversity: Experimental Design of Combinatorial Libraries for Drug Discovery," *J. Med. Chem.* 38:1431-1436.

Marvanova et al., (2001) "Biochemical Characterization of Broad-Specificity Enzymes Using Multivariate Experimental Design and a Colorimetric Microplate Assay: Characterization of the Haloalkane Dehalogenase Mutants," *J. Microbiol Methods*, 44:14-157.

Matsuura et al., (1998) "Nonaddivity of Mutational Effects on the Properties of Catalasa I and its Application to Efficient Directed Evolution," *Protein Eng*, 11(9):789-795.

Moore et al., (Feb. 2004) "Computational Challenges in Combinatorial Library Design in Protein Engineering," *AIChE Journal*, 50(2):262-272.

Nakai et al., (1985) "Structure Modification and Functionality of Whey Proteins: Quantitative Structure-Activity Relationship Approach," *J Dairy Sci*, 68(10):2763-2772.

Nakai et al., (1993) "Recent Advances in Structure and Function of Food Proteins: QSAR Approach," *Crit Rev Food Sci Nutr*, 33(6):477-499.

Nambiar et al., (1984) "Total Synthesis and Cloning of a Gene Coding for the Ribonuclease S Protein," *Science*, 223:1299-1301.

Nielsen et al., (2004) "Improved prediction of MHC class I and class II epitopes using a novel Gibbs sampling approach," *Bioinformatices*, 20(9):1388-1397.

Ness et al., (2000) "Molecular Breeding: The Natural Approach to Protein Design," *Adv Protein Chem*, 55:261-292.

Niggemann et al., (2000) "Exploring Local and Non-Local Interactions for Protein Stability by Structural Motif Engineering," *J Mol Biol*, 296(1):181-195.

Nikolova et al., (1998) "Semirational Design of Active Tumor Suppressor p53 DNA Binding Domain with Enhanced Stability," *Proc Natl Acad Sci USA*, 95(25):14675-14680.

Norinder et al., (1997) "A Quantitative Structure-Activity Relationship Study of Some Substance P-Related Peptides," *J. Peptide Res.*, 49:155-162.

Patel et al., (1998) "Patenting Computer-Designed Peptides," *Journal of Computer-Aided Molecular Design*, 12:543-556.

Perelson et al., (Oct. 10, 1995) "Protein evolution on partially correlated landscapes", *PNAS USA* 92(21):9657-9661.

Pierce et al., (2002)"Protein Design is *NP*-Hard," *Protein Eng*, 15:779-782.

Prusis et al., (2001)"PLS Modeling of Chimeric MS04/MSH-Peptide and $MC_1/MC_3$- Receptor Interaction Reveals a Novel Method for the Analysis of Ligand-Receptor Interactions," *Biochim Biophys Acta*, 1544(1-2):350-357.

Prusis et al., (2002) "Proteo-chemometrics Analysis of MSH Peptide Binding to Melancortin Receptors," *Protein Eng*, 15(4):305-311.

Reymond et al., (2002) "Substrate Arrays as Enzyme Fingerprinting Tools," *Chembiochem*, 3(8):701-708.

Ryu D.D.Y. et al., (2000)"Recent Progress in Biomolecular Engineering," *Biotechnol Prog.*, 16:2-16.

Sadowski et al., (2003) "Automated Generation and Refinement of Protein Signatures: Case Study with G-Protein Coupled Receptors," *Bioinformatics*, 19(6):727-734.

Sandberg et al., (Sep. 1993) "Engineering Multiple Properties of a Protein by Combinatorial Mutagenesis," *Proc. Natl. Acad. Sci. USA*, 90:8367-8371.

Sandberg, (1997) "Deciphering Sequence Data a Multivariate Approach," Ph.D Thesis, Umea: Umea University, 78 pages.

Sandberg et al., (1998) "New Chemical Descriptors Relevant for the Design of Biologically Active Peptides. A Multivariate Characterization of 87 Amino Acids," *J. Med Chem.*, 41:2481-2491.

Schein et al., (2001) "Chloroplast Transit Peptide Prediction: A Peek Inside the Black Box," *Nucleic Acids Res*, 29(16):e82.

Schneider et al., (Oct. 1998) "Peptide Design by Artificial Neural Networks and Compouter-Based Evolutionary Search," *Proc Natl Acad Sci USA*, 95:12179-12184.

Shaw et al., (2002) "Predicting Amino Acid Residues Responsible for Enzyme Specificity Solely from Protein Sequences," *Biotechnol Bioeng*, 79(3):295-300.

Sheridan et al., (1995) "Using a Genetic Algorithm to Suggest Combinatorial Libraries," *J. Chem. Inf. Compu. Sci.*, 35:310-320.

Sheridan et al., (2000) "Designing Targeted Libraries with Genetic Algorithms," *J Mol Graph Model*, 18(4-5):320-334, 525.

Siebert, K.J., (2001) "Quantitative Structure-Activity Relationship Modeling of Peptide and Protein Behavior as a Function of Amino Acid Composition," *J Agric Food Chem*, 49(2): 851-858.

Siebert, K.J., (2003) "Modeling Protein Function Properties from Amino Acid Composition," *J Agric Food Chem*, 51(26):7792-7797.

(56) References Cited

OTHER PUBLICATIONS

Singh et al., (1996) "Application of Genetic Algorithms to Combinatorial Synthesis: A Computational Approach to Lead Identification and Lead Optimization," *J. Am. Chem. Soc.*, 118:1669-1676.
Sjostrom et al.,(1987) "Signal Peptide Amino Acid Sequences in *Escharichla coli* Contain Information Related to Final Protein Localization, A Multivariate Data Analysis," *EMBO*, 6(3):823-891.
Skinner et al., (Oct. 1996) "Potential Use of Additivity of Mutational Effects in Simplifying Protein Engineering," *Proc. Natl. Acad. Sci.*, 93:10753-10757.
Soyer et al., (2002) "Using Evolutionary Methods to Study G-Protein Coupled Receptors," *Pac Symp Biocomput*: 625-636.
Steipe, B., (1999) "Evolutionary Approaches to Protein Engineering," *Curr Top Microbiol Immunol*, 243:55-86.
Strom et al., (2002) "Important Structural Features of 15-Residue Lactoferricin Derivatives and Methods for Improvement of Antimicrobial Activity," *Biochem Cell Biol*, 80:65-74.
Suzuki et al., (1999) "A Method for Detecting Positive Selection at Single Amino Acid Sites," *Mol. Biol. Evol.* 16(10):1315-1328.
Tangri et al., (2002) "Rationally Engineered Proteins or Antibodies with Absent or Reduced Immunogenicity," *Curr Med Chem*, 9:2191-2199.
The GMAX: printed from website http://www.abergc.com, prior to Jul. 21, 2003, 3 pages.
Tobin et al., (2000) "Directed Evolution: The 'Rational' Bases for 'Irrational' Design," *Curr. Opin Struct Biol.*, 10:421-427.
Ufkes et al., (1982) "Further Studies on the Structure-Activity Relationships of Bradykinin-Potentiating Peptides," *European Journal of Pharmacology*, 79:155-158.
Umeno et al., (2002) "Evolution of the $C_{30}$ Carotenoid Synthase CrtM for Function in a $C_{40}$ Pathway," *J Bacteriology* 184(23): 6690-6699.
van Regenmortel, M.H., (2000) "Are There Two Distinct Research Strategies for Developing Biologically Active Molecules: Rational Design and Empirical Selection?", *J. Mol. Recognit*, 13:1-4.
Vector NTI Suite 7.0 User's Manual (portion) describing software believed to be available prior to Feb. 1, 2000, 478 pages.
Veraverbeke et al., (2002) "Wheat Protein Composition and Properties of Wheat Glutenin in Relation to Breadmaking Functionality," *Crit Rev Food Sci Nutr*, 42(3):179-208.
Wahler et al., (2001) "Enzyme Fingerprints by Fluorogenic and Chromogenic Substrate Arrays," *Angew Chem Int Ed Engl.*, 40(23): 4457-4460.
Wahler et al., (2002) "Enzyme Fingerprints of Activity, and Stereo and Enantioselectivity from Fluorogenic and Chromogenic Substrate Arrays," *Chemistry*, 8(14):3211-3228.
Wang et al., (2002) "Designing Gene Libraries from Protein Profiles for Combinatorial Protein Experiments," *Nucleic Acids Res*, 30(21):e120.
Welch et al., (2005) "The *nk* model and population genetics," *Journal of Theoretical Biology*, 234:329-340.
Wells, J.A., (Sep. 18, 1990) "Additivity of Mutational Effects in Proteins," *Biochemistry*, 29(37):8509-8517.
Wells et al., (1992) "Rapid Evolution of Peptide and Protein Binding Properties in vitro," *Curr Opin Biotechnol*, 3:355-362.
Wikberg et al., (2003) "Melanocortin Receptors: Ligands and Protechemometrics Modeling," *Ann NY Acad Sci*, 994:21-26.
Wrede et al., (1998) "Peptide Design Aided by Neural Networks: Biological Activity of Artificial Signal Peptidase I Cleavage Sites," *Biochemistry*, 37:3588-3593.
Wu et al., (1996) "Discovering Empirically Conserved Amino Acid Substitution Groups in Databases of Protein Families," *Proc. Int. Conf. Intell. Syst. Mol. Biol.*, 4:230-240.
Zhang et al., (Feb. 2002) "Genome Shuffling Leads to Rapid Phenotypic Improvement in Bacteria," *Nature*, 415:644-646.
US Office Action dated Mar. 13, 2007 issued in U.S. Appl. No. 10/874,802.
US Office Action dated Jun. 10, 2009 issued in U.S. Appl. No. 11/706,034.
US Notice of Allowance dated Mar. 9, 2010 issued in U.S. Appl. No. 11/706,034.
US Office Action dated Jan. 3, 2011 issued in U.S. Appl. No. 11/981,578.
US Office Action Final dated Sep. 27, 2011 issued in U.S. Appl. No. 11/981,578.
US Office Action dated Oct. 9, 2013 issued in U.S. Appl. No. 11/981,578.
US Notice of Allowance dated Jan. 21, 2014 issued in U.S. Appl. No. 11/981,578.
US Office Action dated Jun. 14, 2010 issued in U.S. Appl. No. 12/557,465.
US Office Action dated Jun. 14, 2010 issued in U.S. Appl. No. 12/557,467.
US Office Action dated Jun. 15, 2010 issued in U.S. Appl. No. 12/557,469.
European Examination Report dated Dec. 23, 2008 issued in EP 05 779 687.2-2405.
European Examination Report dated Jun. 7, 2010 issued in EP 05 779 687.2-2405.
European Examination Report dated Dec. 8, 2011 issued in EP 05 779 687.2-2405.
Japanese Office Action dated Jan. 21, 2011 issued in JP 2007-518248.
Japanese Office Action dated Feb. 8, 2012 issued in JP 2007-518248.
PCT International Search Report dated Nov. 24, 2005 issued in PCT/US2005/022119.
Hellberg et al. (1987) "Peptide Quantitative Structure-Activity Relationships, a Multivariate Approach," Journal of Medicinal Chemistry, 30:1126-1135.
Berglund, et al. (1997) "INLR, Implicit Non-Linear Latent Variable Regression," Journal of Chemometrcis, vol. 11, 141-156.
Fox, Richard (2005) "Directed Molecular Evolution by Machine Learning and the Influence of Nonlinear Interactions," Journal of Theoretical Biology 234:187-199.
Gribskov et al. (1987) "Profile Analysis: Detection of Distantly Related Proteins," Proc. Acad. Sci. USA, vol. 84, 4355-4358.
Hu et al. (2004) "Developing Optimal Non-Linear Scoring Function for Protein Design," Bioinformatics, 20(17):3080-3098.
Voigt, et al. (2001) "Computationally Focusing the Directed Evolution of Proteins," Journal of Callular Biochemistry Supplement 37: 58-63.
US Office Action dated Jan. 14, 2016 issued in U.S. Appl. No. 14/167,709.
PCT International Preliminary Report on Patentability and Written Opinion dated Aug. 13, 2015 issued in PCT/US2014/013666.
PCT International Preliminary Report on Patentability and Written Opinion dated Aug. 13, 2015 issued in PCT/US2014/013668.
Wold et al., (2001) "Some recent developments in PLS modeling," *Chemometrics and Intelligent Laboratory Systems*, 58:131-150.
US Office Action dated Sep. 19, 2016 issued in U.S. Appl. No. 14/256,692.
European Supplementary Search Report dated Oct. 28, 2016 issued in EP 14 74 6677.5.
European Office Action dated Nov. 11, 2016 issued in EP 14 74 6677.5.
Japanese Office Action dated Oct. 11, 2016 issued in JP 2015-556112.
Chinese Office Action dated Sep. 13, 2016 issued in CN 2014800193892.
European Search Report dated Aug. 23, 2016 issued in EP 14 74 6406.9.
European Office Action dated Sep. 2, 2016 issued in EP 14 74 6406.9.
Singapore Search Report and Written Opinion dated Aug. 2, 2016 issued in SG 11201505977R.
Anonymous: "Akaike information criterion—Wikipedia, the free encyclopedia," Jan. 9, 2013 (Jan. 9, 2013), [Retrieved from the Internet on Oct. 11, 2016, at URL:https://en.wikipedia.org/w/index.php?title=Akaike_information_criterion&oldid=532118266], 6pp.
Anonymous: "Saturated mutagenesis—Wikipedia, the free encyclopedia," Dec. 17, 2012 (Dec. 17, 2012), [Retrieved from the Internet

(56) References Cited

OTHER PUBLICATIONS on Aug. 11, 2016, at URL:https://en.wikipedia.org/w/index.php?title=Saturated_mutagenesis&oldid=528472424], 1 page.
US Notice of Allowance dated Jan. 13, 2017 issued in U.S. Appl. No. 14/167,709.

METHODS, SYSTEMS, AND SOFTWARE FOR IDENTIFYING BIO-MOLECULES USING MODELS OF MULTIPLICATIVE FORM

CROSS-REFERENCE TO RELATED APPLICATIONS

This application claims benefit under 35 U.S.C. §119(e) to U.S. Provisional Patent Application No. 61/759,276, entitled: METHODS, SYSTEMS, AND SOFTWARE FOR IDENTIFYING BIO-MOLECULES WITH INTERACTING COMPONENTS, filed Jan. 31, 2013, and U.S. Provisional Patent Application No. 61/799,377, entitled: METHODS, SYSTEMS, AND SOFTWARE FOR IDENTIFYING BIO-MOLECULES USING MODELS OF MULTIPLICATIVE FORM, filed Mar. 15, 2013, which are herein incorporated by reference in their entirety for all purposes.

BACKGROUND

The present disclosure relates to the fields of molecular biology, molecular evolution, bioinformatics, and digital systems. More specifically, the disclosure relates to methods for computationally predicting the activity of a biomolecule and/or guiding directed evolution. Systems, including digital systems, and system software for performing these methods are also provided. Methods of the present disclosure have utility in the optimization of proteins for industrial and therapeutic use.

Protein design has long been known to be a difficult task if for no other reason than the combinatorial explosion of possible molecules that constitute searchable sequence space. The sequence space of proteins is immense and is impossible to explore exhaustively using methods currently known in the art. Because of this complexity, many approximate methods have been used to design better proteins; chief among them is the method of directed evolution. Today, directed evolution of proteins is dominated by various high throughput screening and recombination formats, often performed iteratively.

In parallel, various computational techniques have been proposed for exploring sequence-activity space. While each computational technique has advantages in certain contexts, new ways to efficiently search sequence space to identify functional proteins would be highly desirable.

SUMMARY

The present invention provides methods for identifying bio-molecules with desired properties, or which are most suitable for acquiring such properties, from complex bio-molecule libraries or sets of such libraries. More specifically, some embodiments of the present invention provide methods for building sequence-activity models that include a product of a plurality of multiplicative terms and using the models to guide directed evolution.

Form of the Model

Some embodiments disclosed herein provide methods for building sequence-activity models. Each of the models includes a product of a plurality of multiplicative terms. At least some of the multiplicative terms are non-interaction multiplicative terms, each of which comprises a coefficient representing a defined amino acid or nucleotide's contribution to activity of interest. The defined amino acid or nucleotide is of a specific residue type at a specific position in a protein or nucleic acid sequence. Each of the non-interactive multiplicative terms also includes an independent variable (typically only one independent variable), which may take the form of a dummy variable. The independent variable represents the presence or absence of the defined amino acid or nucleotide, of a specific type at a specific sequence location. These multiplicative terms are termed as non-interaction terms because each of them represents the contribution of a single residue at single position in the protein or nucleic acid sequence. The independent variables in non-interaction terms do not represent two or more interacting residues. In addition, each of the sequence-activity models in some embodiments include a dependent variable representing the activity of a protein variant, where the model describes a relationship between the activity of the protein variant and the product of the plurality of multiplicative terms.

In some embodiments of the invention, the sequence-activity models also include interaction terms, each of which comprises an interaction coefficient representing the contribution to activity of a defined combination of (i) a first amino acid or nucleotide at a first position in the protein sequence, and (ii) a second amino acid or nucleotide at a second position in the protein sequence. The contribution represented by the interaction coefficient is independent and different from the contribution by each of the first residue and second residue in isolation.

In some embodiments, the models combine the interaction terms by multiplication. In some embodiments, the models combine the interaction terms by addition. In some embodiments, the models combine the interaction terms with the non-interaction multiplicative terms by multiplication or addition. In some embodiments, the models are purely multiplicative, combining the non-interaction and interaction terms into a single product. In other embodiments, the models include at least one product of multiple terms combined with one or more other terms by addition.

In some embodiments of the invention, the sequence-activity models have an additive form comprising a sum of one or more non-interaction terms and at least one interaction term. In a context relevant to additive models, a non-interaction term is also referred to as a linear term, while an interaction term is also referred to as a non-linear or cross-product term. Each of the non-interaction terms represents the presence of a defined residue of a specific type at a specific sequence position in a training set of a protein variant library. The at least one interaction term is a cross-product term containing a product of one variable representing the presence of one interacting residue and another variable representing the presence of another interacting residue.

In some embodiments, the non-interaction multiplicative terms and/or the interaction terms have the form of (coefficient×independent variable). In other embodiments, the terms take on the form of (1+coefficient×independent variable). One skilled in the art may apply other expression of the terms when keeping the multiplicative nature of the model. In some embodiments, the coefficients are provided in a look-up table.

In some embodiments, rather than using amino acid sequences, the methods employ nucleotide sequences to generate the models and predict activity. Variations in groups of nucleotides, e.g., codons, affect the activity of peptides encoded by the nucleotide sequences. In some embodiments, the model may provide a bias for codons that are preferentially expressed (compared to other codons encoding the same amino acid) depending upon the host employed to express the peptide.

In some embodiments, methods are provided for directed evolution. While directed evolution may be applied to proteins or nucleic acids that encode proteins, in some cases directed evolution is applied to biological molecules above and beyond proteins. In such embodiments, the sequence-activity models may be employed to characterize relationships between activity and sequence of various biological molecules. For example, the sequence may be that of a whole genome, a whole chromosome, a chromosome segment, a collection of gene sequences for interacting genes, a gene, a nucleic acid sequence, a protein, a polysaccharide, etc. In one or more embodiments, sub-units of the sequence are chromosomes, chromosome segments, haplotypes, genes, nucleotides, codons, mutations, amino acids, carbohydrates (mono, di, tri, or oligomeric), lipid, etc.

In some embodiments, methods for directed evolution of biological molecules may be characterized as follows:
(a) obtaining sequence and activity data for a plurality of biological molecules, each biological molecule comprising a sequence having subunits of various types and sequence positions;
(b) building a sequence-activity model from the obtained data, wherein the sequence-activity model predicts activity as a function of the type and sequence position of subunits, the sequence-activity model comprises a product of a plurality of non-interaction multiplicative terms, each of the non-interaction multiplicative terms comprising (1) a dummy variable representing the presence/absence of a defined subunit of a specific type at a specific sequence position, and (2) a coefficient representing the defined subunit's contribution to activity; and
(c) using the sequence-activity model to identify one or more subunits of specific types at specific positions for variation to impact a desired activity of the biological molecules.

Building and Refining the Model

In one or more implementations consistent with the embodiments above, a training set for generating a sequence activity model is derived from a plurality of protein variants, which may be provided as a protein library. The protein library may include proteins from various sources. In one example, the members include naturally occurring proteins such as those encoded by members of a single gene family. In another example, the sequences include proteins obtained by using a recombination-based diversity generation mechanism. For example, DNA fragmentation-mediated recombination, synthetic oligonucleotide-mediated recombination or a combination thereof may be performed on nucleic acids encoding all or part of one or more naturally occurring parent proteins for this purpose. In still another example, the members are obtained by implementing a design of experiment (DOE) protocol to identify the systematically varied sequences.

In some embodiments, the sequence and activity data for each of the plurality of protein variants are obtained by (i) assaying each of the plurality of protein variants to determine its activity, and (ii) sequencing each of the plurality of protein variants to determine its sequence. The obtained data for each sequence is also referred to as an observation. Collectively, the observations comprise a training set.

Some embodiments provide techniques for selecting terms and coefficients for models that best describe the activity of the sequence. Note that there are often far more possible pair-wise or higher-order interaction terms than there are true interactions between residues. Hence, to avoid overfitting, only a limited number of interaction terms are typically considered and those employed should reflect interactions that affect activity.

Some embodiments provide methods for generating the sequence-activity model by performing a stepwise addition, subtraction, or multiplication of interaction and/or non-interaction terms.

Genetic algorithms are among the techniques that may be employed to generate models having the form of products of interaction or non-interaction terms as described above. Regression techniques and genetic algorithms are among the techniques that may be employed to generate models having the form of sums of interaction or non-interaction terms as described above.

One aspect of the disclosure provides a stepwise method of preparing a sequence-activity model that can assist identifying biological molecules to affect a desired activity, the method comprising: (a) receiving sequence and activity data for a plurality of biological molecules; (b) preparing a base model from the sequence and activity data, wherein the base model predicts activity as a function of the presence or absence of sub-units of the sequence; (c) preparing at least one new model by adding, subtracting, or multiplying at least one new interaction term to/from the base model, where the new interaction term represents the interaction between two or more interacting sub-units; (d) determining the ability of the at least one new model to predict activity as a function of the presence or absence of the subunits; and (e) determining whether to add/subtract the new interaction term to/from the base model based on the ability of the at least one new model to predict activity as determined in (d) and with a bias against adding the new interaction term. The model derived can then be used in various applications, such as in directed evolution of protein libraries to identify proteins with desired biological activities and properties.

Some embodiments provide methods of using a genetic algorithm to select one or more terms of the sequence-activity models. Other embodiments provide methods of using a genetic algorithm to adjust the values of the coefficients to fit the models to the obtained data.

In one or more embodiments, a model including interaction terms is fitted to observed data using Bayesian regression techniques, wherein prior knowledge is used to determine posterior probability distributions of the model.

In one or more embodiments, two or more new models are created, each of which includes at least one different interaction term. In such embodiments, the method further comprises preparing an ensemble model based on the two or more new models. The ensemble model includes interaction terms from the two or more new models. The ensemble model weights the interaction terms according to the two or more new models' abilities to predict activity of interest.

The sequence-activity model may be produced from the training set by many different techniques. In certain embodiments, the model is a regression model such as a partial least squares model, a Bayesian regression model, or a principal component regression model. In another embodiment, the model is a neural network.

Unless explicitly stated or otherwise inherently incompatible, the methods to refine the models and the various forms of models described herein are compatible with each other. They can be used in various combinations to generate desired sequence-activity models. In some embodiments of the invention, the generated models can be used to guide directed evolution.

Using the Model to Guide Directed Evolution

In certain embodiments, protein variants of desired activity are identified through directed evolution. Some embodiments provide methods to guide directed evolution of protein variants using the generated sequence-activity models. The various sequence-activities models prepared and refined according to the methods described above are suitable to guide directed evolution of proteins or biological molecules. As part of the process, the methods may identify sequences that are to be used for generating a new protein variant library. Such sequences include variations on the defined residues identified above, or are precursors used to subsequently introduce such variations. The sequences may be modified by performing mutagenesis or a recombination-based diversity generation mechanism to generate the new library of protein variants. Either or both forms of diversity generation may form part of a directed evolution procedure. The new library may also be used in developing a new sequence-activity model. The new protein variant library is analyzed to assess effects on a particular activity such as stability, catalytic activity, therapeutic activity, resistance to a pathogen or toxin, toxicity, etc.

In some embodiments, preparation of oligonucleotides or nucleic acid sequences is achieved by synthesizing the oligonucleotides or nucleic acid sequences using a nucleic acid synthesizer. Some embodiments of the invention include performing a round of directed evolution using the prepared oligonucleotides or protein sequence as building blocks for directed evolution. Various embodiments of the invention apply recombination and/or mutagenesis to these building blocks to generate diversity.

As one example, some embodiments apply recombination techniques to oligonucleotides. In these embodiments, the methods involve selecting one or more mutations for a round of directed evolution by evaluating the coefficients of the terms of a sequence-activity model. Selected mutations represent defined amino acids or nucleotides of specific types at specific positions based on their contributions to the activity of proteins as predicted by the models. In some embodiments, selection of mutations involves identifying one or more coefficients that are determined to be larger than others of the coefficients (or otherwise indicated a strong impact on activity), and selecting the defined amino acids or nucleotides at defined positions represented by the one or more coefficients so identified. In some embodiments, after selecting mutations according to the sequence-activity models, the methods involve preparing a plurality of oligonucleotides containing or encoding the one or more mutations, and performing a round of directed evolution using the oligonucleotides so prepared. In some embodiments, the directed evolution techniques involve combining and/or recombining the oligonucleotides. A shuffling reaction may be performed using the oligonucleotides.

Other embodiments apply recombination techniques to protein sequences. In some embodiments, the methods involve identifying a new protein or a new nucleic acid sequence, and preparing and assaying the new protein or a protein encoded by the new nucleic acid sequence. In some embodiments, the methods further involve using the new protein or protein encoded by the new nucleic acid sequence as a starting point for further directed evolution. In some embodiments, the directed evolution process involves fragmenting and recombining the protein sequence that is predicted by the model to have a desired level of activity.

In some embodiments, the methods identify and/or prepare a new protein or a new nucleic acid sequence based on individual mutations that are predicted to be important by the model. These methods involve: selecting one or more mutations by evaluating the coefficients of the terms of the sequence-activity model to identify one or more of the defined amino acids or nucleotides at the defined positions that contribute to the activity; identifying a new protein or a new nucleic acid sequence comprising the one or more mutations selected above, and preparing and assaying the new protein or a protein encoded by the new nucleic acid sequence.

In other embodiments, the methods identify and/or prepare a new protein or a new nucleic acid sequence based on the predicted activity of a whole sequence instead of individual mutations. In some of these embodiments, the methods involve applying multiple protein sequences or multiple amino acid sequences to the sequence-activity model and determining activity values predicted by the sequence-activity model for each of the multiple protein sequences or nucleic acid sequences. The methods further involve selecting a new protein sequence or a new nucleic acid sequence from among the multiple protein sequences or multiple amino acid sequences applied above by evaluating the activity values predicted by the sequence-activity model for the multiple sequences. The methods also involve preparing and assaying a protein having the new protein sequence or a protein encoded by the new nucleic acid sequence.

Some embodiments include selecting one or more positions in the protein sequence or nucleic acid sequence and conducting saturation mutagenesis at the one or more positions so identified. In some embodiments, the positions are selected by evaluating the coefficients of the terms of the sequence-activity model to identify one or more of the defined amino acids or nucleotides at the defined positions that contribute to the activity. Accordingly, in some embodiments, a round of directed evolution includes performing saturation mutagenesis on a protein sequence at positions selected using the sequence-activity models. In some embodiments involving models comprising one or more interaction terms, the methods involve applying mutagenesis simultaneously at the two or more interacting residues.

In some embodiments, the method involves selecting one or more members of the new protein variant library for production. One or more of these may then be synthesized and/or expressed in an expression system. In a specific embodiment, the method continues in the following manner: (i) providing an expression system from which a selected member of the new protein variant library can be expressed; and (ii) expressing the selected member of the new protein variant library.

Some embodiments use the sequence-activity model to identify a backbone or reference sequence in which residues are identified for fixing or variation. In some cases, the reference sequence is a sequence predicted by the model to have the highest value (or one of the highest values) of the desired activity. In another case, the reference sequence is a member of the original protein variant library. From the reference sequence, the method may select subsequences for effecting the variations. Additionally or alternatively, the sequence-activity model ranks residue positions (or specific residues at certain positions) in order of impact on the desired activity.

Another aspect of the disclosure pertains to apparatus and computer program products including machine-readable media on which are provided program instructions and/or arrangements of data for implementing the methods and software systems described above. Frequently, the program instructions are provided as code for performing certain method operations. Data, if employed to implement features of this disclosure, may be provided as data structures, database tables, data objects, or other appropriate arrangements of specified information. Any of the methods or systems described herein may be represented, in whole or in part, as such program instructions and/or data provided on any suitable machine-readable media.

These and other features are described in more detail below in the detailed description and in conjunction with the following figures.

BRIEF DESCRIPTION OF THE DRAWINGS

FIG. 4A illustrates a specific example of a stepwise addition method for preparing a model; and FIG. 4B illustrates a specific example of a stepwise subtraction method for preparing a model.

DETAILED DESCRIPTION

I. Definitions

Figure 1A:
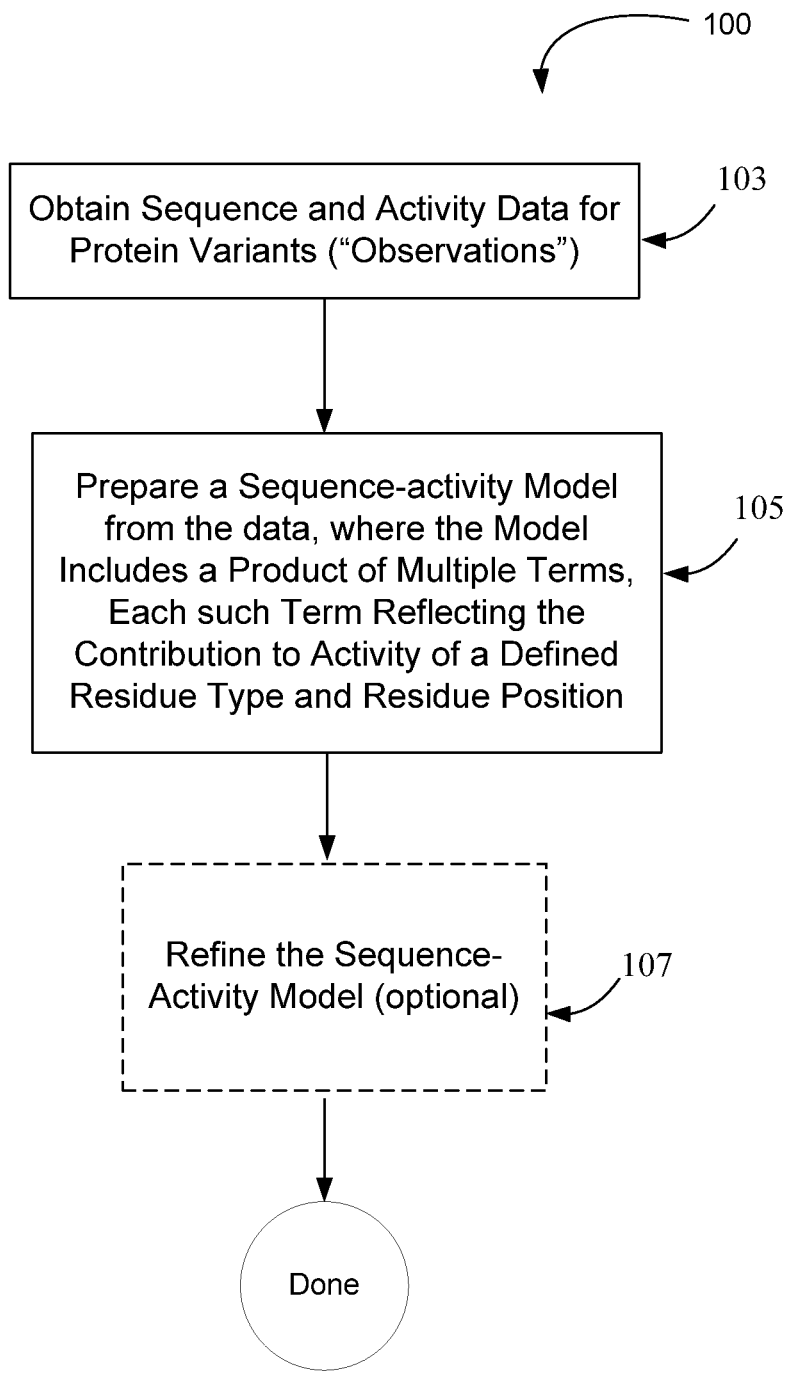
FIG. 1A is a flow chart depicting the general process to generate a multiplicative sequence-activity model.

Unless defined otherwise herein, all technical and scientific terms used herein have the same meaning as commonly understood by one of ordinary skill in the art. Various scientific dictionaries that include the terms included herein are well known and available to those in the art. Any methods and materials similar or equivalent to those described herein find use in the practice of the embodiments disclosed herein.

The terms defined immediately below are more fully understood by reference to the specification as a whole. The definitions are for the purpose of describing particular embodiments only and aiding in understanding the complex concepts described in this specification. They are not intended to limit the full scope of the disclosure. Specifically, it is to be understood that this disclosure is not limited to the particular sequences, compositions, algorithms, systems, methodology, protocols, and reagents described, as these may vary, depending upon the context they are used by those of skill in the art.

As used in this specification and appended claims, the singular forms "a", "an", and "the" include plural referents unless the content and context clearly dictates otherwise. Thus, for example, reference to "a device" includes a combination of two or more such devices, and the like.

Unless indicated otherwise, an "or" conjunction is intended to be used in its correct sense as a Boolean logical operator, encompassing both the selection of features in the alternative (A or B, where the selection of A is mutually exclusive from B) and the selection of features in conjunction (A or B, where both A and B are selected). In some places in the text, the term "and/or" is used for the same purpose, which shall not be construed to imply that "or" is used with reference to mutually exclusive alternatives.

A "bio-molecule" or "biological molecule" refers to a molecule that is generally found in a biological organism. In some embodiments, biological molecules comprise polymeric biological macromolecules having multiple subunits (i.e., "biopolymers"). Typical bio-molecules include, but are not limited to, molecules that share some structural features with naturally occurring polymers such as RNAs (formed from nucleotide subunits), DNAs (formed from nucleotide subunits), and peptides or polypeptides (formed from amino acid subunits), including, e.g., RNAs, RNA analogues, DNAs, DNA analogues, polypeptides, polypeptide analogues, peptide nucleic acids (PNAs), combinations of RNA and DNA (e.g., chimeraplasts), or the like. It is not intended that bio-molecules be limited to any particular molecule, as any suitable biological molecule finds use in the present invention, including but not limited to, e.g., lipids, carbohydrates, or other organic molecules that are made by one or more genetically encodable molecules (e.g., one or more enzymes or enzyme pathways) or the like.

The terms "polynucleotide" and "nucleic acid" refer to deoxyribonucleotides or ribonucleotides and polymers (e.g., oligonucleotides, polynucleotides, etc.) thereof in either single- or double-stranded form. These terms include, but are not limited to, single-, double- or triple-stranded DNA, genomic DNA, cDNA, RNA, DNA-RNA hybrid, polymers comprising purine and pyrimidine bases, and/or other natural, chemically or biochemically modified, non-natural or derivatized nucleotide bases. The following are non-limiting examples of polynucleotides: genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracyl, other sugars and linking groups such as fluororibose and thioate, and/or nucleotide branches. In some alternative embodiments, the sequence of nucleotides is interrupted by non-nucleotide components.

Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260: 2605-2608; Rossolini et al. (1994) Mol. Cell. Probes 8:91-98). The term nucleic acid is used interchangeably with, e.g., oligonucleotide, polynucleotide, cDNA, and mRNA.

The terms "protein," "polypeptide" and "peptide" are used interchangeably to denote a polymer of at least two amino acids covalently linked by an amide bond, regardless of length or post-translational modification (e.g., glycosylation, phosphorylation, lipidation, myristilation, ubiquitination, etc.). In some cases, the polymer has at least about 30 amino acid residues, and usually at least about 50 amino acid residues. More typically, they contain at least about 100 amino acid residues. The terms include compositions conventionally considered to be fragments of full-length proteins or peptides. Included within this definition are D- and L-amino acids, and mixtures of D- and L-amino acids. The polypeptides described herein are not restricted to the genetically encoded amino acids. Indeed, in addition to the genetically encoded amino acids, the polypeptides described herein may be made up of, either in whole or in part, naturally-occurring and/or synthetic non-encoded amino acids. In some embodiments, a polypeptide is a portion of the full-length ancestral or parental polypeptide, containing amino acid additions or deletions (e.g., gaps) or substitutions as compared to the amino acid sequence of the full-length parental polypeptide, while still retaining functional activity (e.g., catalytic activity).

As used herein, the term "cellulase" refers to a category of enzymes capable of hydrolyzing cellulose (β-1,4-glucan or β-D-glucosidic linkages) to shorter cellulose chains, oligosaccharides, cellobiose and/or glucose. In some embodiments, the term "cellulase" encompasses beta-glucosidases, endoglucanases, cellobiohydrolases, cellobiose dehydrogenases, endoxylanases, beta-xylosidases, arabinofuranosidases, alpha-glucuronidases, acetylxylan esterases, feruloyl esterases, and/or alpha-glucuronyl esterases. In some embodiments, the term "cellulase" encompasses hemicellulose-hydrolyzing enzymes, including but not limited to endoxylanases, beta-xylosidases, arabinofuranosidases, alpha-glucuronidases, acetylxylan esterase, feruloyl esterase, and alpha-glucuronyl esterase. A "cellulase-producing fungal cell" is a fungal cell that expresses and secretes at least one cellulose hydrolyzing enzyme. In some embodiments, the cellulase-producing fungal cells express and secrete a mixture of cellulose hydrolyzing enzymes. "Cellulolytic," "cellulose hydrolyzing," "cellulose degrading," and similar terms refer to enzymes such as endoglucanases and cellobiohydrolases (the latter are also referred to as "exoglucanases") that act synergistically to break down the cellulose to soluble di- or oligosaccharides such as cellobiose, which are then further hydrolyzed to glucose by beta-glucosidase. In some embodiments, the cellulase is a recombinant cellulase selected from β-glucosidases (BGLs), Type 1 cellobiohydrolases (CBH1s), Type 2 cellobiohydrolases (CBH2s), glycoside hydrolase 61s (GH61s), and/or endoglucanases (EGs). In some embodiments, the cellulase is a recombinant Myceliophthora cellulase selected from β-glucosidases (BGLs), Type 1 cellobiohydrolases (CBH1s), Type 2 cellobiohydrolases (CBH2s), glycoside hydrolase 61s (GH61s), and/or endoglucanases (EGs). In some additional embodiments, the cellulase is a recombinant cellulase selected from EG1b, EG2, EG3, EG4, EG5, EG6, CBH1a, CBH1b, CBH2a, CBH2b, GH61a, and/or BGL.

The term "sequence" is used herein to refer to the order and identity of any biological sequences including but not limited to a whole genome, whole chromosome, chromosome segment, collection of gene sequences for interacting genes, gene, nucleic acid sequence, protein, polysaccharide, etc. In some contexts, a sequence refers to the order and identity of amino acid residues in a protein (i.e., a protein sequence or protein character string) or to the order and identity of nucleotides in a nucleic acid (i.e., a nucleic acid sequence or nucleic acid character string). A sequence may be represented by a character string. A "nucleic acid sequence" refers to the order and identity of the nucleotides comprising a nucleic acid. A "protein sequence" refers to the order and identity of the amino acids comprising a protein or peptide.

"Codon" refers to a specific sequence of three consecutive nucleotides that is part of the genetic code and that specifies a particular amino acid in a protein or starts or stops protein synthesis.

"Native sequence" or "wild type sequence" refers to a polynucleotide or polypeptide isolated from a naturally occurring source. Included within "native sequence" are recombinant forms of a native polypeptide or polynucleotide which have a sequence identical to the native form.

The term "gene" is used broadly to refer to any segment of DNA or other nucleic acid associated with a biological function. Thus, genes include coding sequences and optionally, the regulatory sequences required for their expression. Genes also optionally include nonexpressed nucleic acid segments that, for example, form recognition sequences for other proteins. Genes can be obtained from a variety of sources, including cloning from a source of interest or synthesizing from known or predicted sequence information, and may include sequences designed to have desired parameters.

A "motif" refers to a pattern of subunits in or among biological molecules. For example, the term "motif" can be used in reference to a subunit pattern of the unencoded biological molecule or to a subunit pattern of an encoded representation of a biological molecule.

The term "chromosome" is used in reference to an organized structure of DNA and associated protein found cells, comprising a single piece of coiled DNA including many genes, regulatory elements, and other nucleotide sequences. The term is also used in reference to the DNA sequence of the structure.

In the context of genetic algorithm, the term "chromosome" is used as an alias for an individual model (or a set of model parameters) in a population of models. It is so used because a model from a parent generation passes its parameters (or genes) onto the models of a child generation, which resembles the manners that a parent chromosome passing its genes to a child chromosome.

"Screening" refers to the process in which one or more properties of one or more bio-molecules are determined. For example, typical screening processes include those in which one or more properties of one or more members of one or more libraries are determined.

An "expression system" is a system for expressing a protein or peptide encoded by a gene or other nucleic acid.

"Host cell" or "recombinant host cell" refers to a cell that comprises at least one recombinant nucleic acid molecule. Thus, for example, in some embodiments, recombinant host cells express genes that are not found within the native (i.e., non-recombinant) form of the cell.

"Directed evolution," "guided evolution," or "artificial evolution" refers to in vitro or in vivo processes of artificially changing one or more biomolecule sequences (or a character string representing that sequence) by artificial selection, mutation, recombination, or other manipulation. In some embodiments, directed evolution occurs in a reproductive population in which there are (1) varieties of individuals, with some varieties being (2) heritable, of which some varieties (3) differ in fitness. Reproductive success is determined by outcome of selection for a predetermined property such as a beneficial property. The reproductive population can be, e.g., a physical population or a virtual population in a computer system.

In certain embodiments, directed evolution methods generate protein variant libraries by recombining genes encoding variants of a parent protein variant library. The methods may employ oligonucleotides containing sequences or subsequences for encoding the proteins of a parental variant library. Some of the oligonucleotides of the parental variant library may be closely related, differing only in the choice of codons for alternate amino acids selected to be varied by recombination with other variants. The method may be performed for one or multiple cycles until desired results are achieved. If multiple cycles are used, each involves a screening step to identify which variants having acceptable performance are to be used in a subsequent recombination cycle.

In some embodiments, directed evolution methods generate protein variants by sited directed mutagenesis at defined locations identified by sequence-activity models. Some embodiments employ saturation mutagenesis, in which one tries to generate all possible (or as close to as possible) mutations at a specific site, or narrow region of a gene.

"Shuffling" and "gene shuffling" refer to directed evolution methods for introducing diversity by recombining a collection of fragments of the parental polynucleotides through a series of chain extension cycles. In certain embodiments, one or more of the chain extension cycles is self-priming; i.e., performed without the addition of primers other than the fragments themselves. Each cycle involves annealing single stranded fragments through hybridization, subsequent elongation of annealed fragments through chain extension, and denaturing. Over the course of shuffling, a growing nucleic acid strand is typically exposed to multiple different annealing partners in a process sometimes referred to as "template switching." As used herein, "template switching" refers to the ability to switch one nucleic acid domain from one nucleic acid with a second domain from a second nucleic acid (i.e., the first and second nucleic acids serve as templates in the shuffling procedure).

Template switching frequently produces chimeric sequences, which result from the introduction of crossovers between fragments of different origins. The crossovers are created through template switched recombinations during the multiple cycles of annealing, extension, and denaturing. Thus, shuffling typically leads to production of variant polynucleotide sequences. In some embodiments, the variant sequences comprise, a "library" of variants. In some embodiments of these libraries, the variants contain sequence segments from two or more of parent polynucleotides.

When two or more parental polynucleotides are employed, the individual parental polynucleotides are sufficiently homologous that fragments from different parents hybridize under the annealing conditions employed in the shuffling cycles. In some embodiments, the shuffling permits recombination of parent polynucleotides having relatively limited homology. Often, the individual parent polynucleotides have distinct and/or unique domains and/or other sequence characteristics of interest. When using parent polynucleotides having distinct sequence characteristics, shuffling can produce highly diverse variant polynucleotides.

Various shuffling techniques are known in the art. See e.g., U.S. Pat. Nos. 6,917,882, 7,776,598, 8,029,988, 7,024, 312, and 7,795,030, all of which are incorporated herein by reference in their entireties.

"Gene Splicing by Overlap Extension" or "gene SOEing" is a PCR-based method of recombining DNA sequences without reliance on restriction sites and of directly generating mutated DNA fragments in vitro. By modifying the sequences incorporated into the 5'-ends of the primers, any pair of polymerase chain reaction products can be made to share a common sequence at one end. Under polymerase chain reaction conditions, the common sequence allows strands from two different fragments to be complementary to each other and hybridize to one another, forming a new sequence having the two fragments on each end joined by an overlap of the common sequence. Extension of this overlap by DNA polymerase yields a recombinant molecule.

"Mutagenesis" is the process of introducing a mutation into a standard or reference sequence such as a parent nucleic acid or parent polypeptide.

Site directed mutagenesis is one example of a useful technique for introducing mutations, although any suitable method finds use. Thus, alternatively or in addition, the mutants may be provided by gene synthesis, saturating random mutagenesis, semi-synthetic combinatorial libraries of residues, directed evolution, recursive sequence recombination ("RSR") (See e.g., US Patent Application No. 2006/0223143, incorporated by reference herein in its entirety), gene shuffling, error-prone PCR, and/or any other suitable method.

One example of a suitable saturation mutagenesis procedure is described in US Published Patent Application No. 20100093560, which is incorporated herein by reference in its entirety.

A "fragment" is any portion of a sequence of nucleotides or amino acids. Fragments may be produced using any suitable method known in the art, including but not limited to cleaving a polypeptide or polynucleotide sequence. In some embodiments, fragments are produced by using nucleases that cleave polynucleotides. In some additional embodiments, fragments are generated using chemical and/or biological synthesis techniques. In some embodiments, fragments comprise subsequences of at least one parental sequence, generated using partial chain elongation of complementary nucleic acid(s).

"Parental polypeptide," "parental polynucleotide," "parent nucleic acid," and "parent" are generally used to refer to the wild-type polypeptide, wild-type polynucleotide, or a variant used as a starting point in a diversity generation procedure such as a directed evolution. In some embodiments, the parent itself is produced via shuffling or other diversity generation procedure. In some embodiments, mutants used in directed evolution are directly related to a parent polypeptide. In some embodiments, the parent polypeptide is stable when exposed to extremes of temperature, pH and/or solvent conditions and can serve as the basis for generating variants for shuffling. In some embodiments, the parental polypeptide is not stable to extremes of temperature, pH and/or solvent conditions, and the parental polypeptide is evolved to make a robust variants.

A "parent nucleic acid" encodes a parental polypeptide.

"Mutant," "variant," and "variant sequence" as used herein, refer to a biological sequence that differs in some respect from a standard or reference sequence. The difference may be referred to as a "mutation". In some embodiments, a mutant is an amino acid (i.e., polypeptide) or polynucleotide sequence that has been altered by at least one substitution, insertion, cross-over, deletion, and/or other genetic operation. For purposes of the present disclosure, mutants and variants are not limited to a particular method by which they are generated. In some embodiments, a mutant or variant sequence has increased, decreased, or substantially similar activities or properties, in comparison to the parental sequence. In some embodiments, the variant polypeptide comprises one or more amino acid residues that have been mutated, as compared to the amino acid sequence of the wild-type polypeptide (e.g., a parent polypeptide). In some embodiments, one or more amino acid residues of the polypeptide are held constant, are invariant, or are not mutated as compared to a parent polypeptide in the variant polypeptides making up the plurality. In some embodiments, the parent polypeptide is used as the basis for generating variants with improved stability, activity, or other property.

A "library" or "population" refers to a collection of at least two different molecules, character strings, and/or models, such as nucleic acid sequences (e.g., genes, oligonucleotides, etc.) or expression products (e.g., enzymes or other proteins) therefrom. A library or population generally includes a number of different molecules. For example, a library or population typically includes at least about 10 different molecules. Large libraries typically include at least about 100 different molecules, more typically at least about 1000 different molecules. For some applications, the library includes at least about 10000 or more different molecules. In certain embodiments, the library contains a number variant or chimeric nucleic acids or proteins produced by a directed evolution procedure.

Two nucleic acids are "recombined" when sequences from each of the two nucleic acids are combined in a progeny nucleic acid. Two sequences are "directly" recombined when both of the nucleic acids are substrates for recombination.

"Selection" refers to the process in which one or more bio-molecules are identified as having one or more properties of interest. Thus, for example, one can screen a library to determine one or more properties of one or more library members. If one or more of the library members is/are identified as possessing a property of interest, it is selected. Selection can include the isolation of a library member, but this is not necessary. Further, selection and screening can be, and often are, simultaneous.

A "dependent variable" represents an output or effect, or is tested to see if it is the effect. The "independent variables" represent the inputs or causes, or are tested to see if they are the cause. A dependent variable may be studied to see if and how much it varies as the independent variables vary.

In the simple stochastic linear model $$y_i = a + bx_i + e_i$$

where the term $y_i$ is the $i^{th}$ value of the dependent variable and $x_i$ is $i^{th}$ value of the independent variable. The term $e_i$ is known as the "error" and contains the variability of the dependent variable not explained by the independent variable.

An independent variable is also known as a "predictor variable", "regressor", "controlled variable", "manipulated variable", "explanatory variable", or "input variable".

An "additive model" is a model describing the relationship between a dependent variable y as a function of multiple independent variables $x_i$, wherein the model combines the independent variables' contributions to the dependent variable by adding multiple terms, each term including an expression of an independent variable. The expression of the independent variable reflects the independent variable's contribution to the dependent variable.

In some embodiments, a mathematical model is used to describe the relationship between one or more independent variables (IVs) and a dependent variable (DV). The model can be written as DV=Algebraic expression of (IVs). An "algebraic expression" can include variables, coefficients, constants, and operating symbols, such as plus and minus signs. $4x^2+3xy+7y+5$ is a bivariate algebraic expression.

In an additive model, terms are the elements separated by the plus or minus signs. The example above takes the form of an additive model. It has four terms, $4x^2$, $3xy$, $7y$, and 5. Terms may consist of variables and coefficients ($4x^2$, $3xy$, and $7y$), or constants (5). In algebraic expressions, variables can take on various values to represent changing conditions of a system. For instance, it can be a continuous variable representing the speed of a traveling car or a discrete variable with multiple non-continuous values representing amino acid types. A variable can be a bit value variable representing the presence or absence of an entity, e.g., the presence or absence of a residue of a specific type at a specific position. In the algebraic expression above, the variables are x and y.

In some embodiments, "terms" of an expression may be elements of the expression that are demarcated by other signs. For instance, a multiplicative model has terms connected by multiplication as further explained below.

"Coefficient" refers to a scalar value multiplied by a dependent variable or an expression containing a dependent variable. In the example above, "coefficients" are the number part of the terms in an algebraic expression. In $4x^2+3xy+7y+5$, the coefficient of the first term is 4. The coefficient of the second term is 3, and the coefficient of the third term is 7. If a term consists of only variables, its coefficient is 1.

"Constants" are the terms in the algebraic expression that contain only numbers. That is, they are the terms without variables. In the expression $4x^2+3xy+7y+5$, the constant term is "5."

A "linear term" is a term with a degree of 1, or a single variable raised to the power of 1. In the example above, the term 7y is a linear term because its degree is 1 ($y^1$ or simply y). In contrast, the term $4x^2$ is a quadratic term because the x has a degree of 2, and 3xy is a bivariate quadratic term because x and y each has a degree of 1, the product leading to a degree of 2.

An additive model may include linear and/or non-linear terms. "Linear term" refers to a term of an additive model comprising the product of a single independent variable and an associated coefficient, wherein the quantity of the model changes linearly as the independent variable changes. The term "linear model" or "linear additive model" refers to any additive model whose terms are all linear terms. It assumes there are no interactions between the independent variable (i.e., each independent variable contributes independently to the overall fitness of the protein). The simple stochastic linear model describe above is an example of a linear additive model.

In the context of additive models, unless specified otherwise, "non-linear term," "cross-product term," and "interaction term" are used interchangeably, and they refer to a term of a model comprising an expression including the product of two or more independent variables. In some embodiments, this expression can be simply a constant coefficient times the product: $c_{i,j} \times x_i x_j$. In the context of additive models, the term "non-linear model" or "non-linear additive model" refers to any additive model including at least one non-linear term in the meaning above. However, in some places in the text, "non-linear term" refers to a broader sense wherein the term comprises various forms of a single independent variable, including but not limited to a power function or exponential function of the independent variable.

A "multiplicative model" is a model describing the relationship between a dependent variable y as a function of multiple independent variables $x_i$, wherein the model combines the independent variables' contributions to the dependent variable by multiplying multiple terms, each of which comprises an expression of an independent variable. The expression of the independent variable reflects the independent variable's contribution to the dependent variable.

Note that "linear term" and "linear model" are not applicable to a multiplicative model. So a multiplicative model is only described as interaction or non-interaction rather than linear or non-linear. A multiplicative model may include non-interaction and/or interaction terms. A "non-interaction term" in a multiplicative model refers to a term of a model comprising an expression of a single independent variable.

Similar to additive models, an "interaction term" in a multiplicative model refers to a term of a model comprising an expression including the product of two or more independent variables. In some embodiments, this expression can be simply a constant coefficient times the product: $c_{i,j} \times x_i x_j$. In other embodiments, the expression can be $(1 + c_{i,j} \times x_i x_j)$.

"Interacting sub-units" refers to two or more sub-units of a sequence that have synergistic effects on the modeled activity of the sequence, the synergistic effects being separate and different from the sub-units' individual effects on the modeled activity.

"Product" refers to the result of multiplying two or more variables or terms.

"Coefficient" refers to a scalar value multiplied by a dependent variable or an expression containing a dependent variable.

"Orthogonal/orthogonality" refers to an independent variable that is uncorrelated with other independent variables in a model or other relationship.

The term "sequence-activity model" refers to any mathematical models that describe the relationship between activities, characteristics, or properties of biological molecules on the one hand, and various biological sequences on the other hand.

The term "encoded character string" refers to a representation of a biological molecule that preserves sequence/structural information regarding that molecule. In some embodiments, the encoded character string contains information about sequence mutations in a library of variants. Encoded character strings of bio-molecules along with activity information for the bio-molecules may be used as a training set for a sequence activity model. Non-sequence properties of bio-molecules can be stored or otherwise associated with encoded character strings for the bio-molecules.

"Reference sequence" is a sequence from which variation of sequence is effected. In some cases, a "reference sequence" is used to define the variations. Such sequence may be one predicted by a model to have the highest value (or one of the highest values) of the desired activity. In another case, the reference sequence may be that of a member of an original protein variant library. It certain embodiments, a reference sequence is the sequence of a parent protein or nucleic acid.

"Training set" refers to a set of sequence-activity data or observations that one or more models are fitted to and built upon. For instance, for a protein sequence-activity model, a training set comprises residue sequences for an initial or improved protein variant library. Typically, these data include complete or partial residue sequence information, together with an activity value for each protein in the library. In some cases, multiple types of activities (e.g., rate constant data and thermal stability data) are provided together in the training set. The activity is sometimes a beneficial property.

The term "observation" is information about protein or other biological entity that may be used in a training set for generating a model such as a sequence activity model. The term "observation" may refer to any sequenced and assayed biological molecules, including protein variants. In certain embodiments, each observation is an activity value and an associated sequence for a variant in a library. Generally, the more observations employed to create a sequence-activity model, the better the predictive power of that sequence-activity model.

As used herein, the term "beneficial property" is intended to refer to a phenotypic or other identifiable feature that confers some benefit to a protein or a composition of matter or process associated with the protein. Examples of beneficial properties include an increase or decrease, when compared to a parent protein, in a variant protein's catalytic properties, binding properties, stability when exposed to extremes of temperature, pH, etc., sensitivity to stimuli, inhibition, and the like. Other beneficial properties may include an altered profile in response to a particular stimulus. Further examples of beneficial properties are set forth below. Values of beneficial properties may be used as activity values in the observations used in a training set for a sequence activity model.

"Next-generation sequencing" or "high-throughput sequencing" are sequencing techniques that parallelize the sequencing process, producing thousands or millions of sequences at once. Examples of suitable next-generation sequencing methods include, but are not limited to, single molecule real-time sequencing (e.g., Pacific Biosciences, Menlo Park, Calif.), ion semiconductor sequencing (e.g., Ion Torrent, South San Francisco, Calif.), pyrosequencing (e.g., 454, Branford, Conn.), sequencing by ligation (e.g., SOLid sequencing of Life Technologies, Carlsbad, Calif.), sequencing by synthesis and reversible terminator (e.g., Illumina, San Diego, Calif.), nucleic acid imaging technologies such as transmission electron microscopy, and the like. Further descriptions of exemplary techniques are described in the detailed description of this disclosure.

"Predictive power" refers to the ability of a model to correctly predict the values of a dependent variable for data under various conditions. For example, the predictive power of a sequence activity model refers to the ability of the model to predict activity from sequence information.

"Cross validation" refers to a method for testing the generalizability of a model's ability to predict a value of interest (i.e. the value of the dependent variable). The method prepares a model using one set of data, and tests the model error using a different set of data. The first set of data is viewed as a training set, and the second set of data is a validation set.

"Systematic variance" refers to different descriptors of an item or set of items being changed in different combinations.

"Systematically varied data" refers to data produced, derived, or resulting from different descriptors of an item or set of items being changed in different combinations. Many different descriptors can be changed at the same time, but in different combinations. For example, activity data gathered from polypeptides in which combinations of amino acids have been changed is systematically varied data.

The term "systematically varied sequences" refers to a set of sequences in which each residue is seen in multiple contexts. In principle, the level of systematic variation can be quantified by the degree to which the sequences are orthogonal from one another (i.e., maximally different compared to the mean).

The term "toggling" refers to the introduction of multiple amino acid residue types into a specific position in the sequences of protein variants in the optimized library.

The terms "regression" and "regression analysis" refer to techniques used to understand which among the independent variables are related to the dependent variable, and to explore the forms of these relationships. In restricted circumstances, regression analysis can be used to infer causal relationships between the independent and dependent variables. It is a statistical technique for estimating the relationships among variables. It includes many techniques for modeling and analyzing several variables, when the focus is on the relationship between a dependent variable and one or more independent variables. More specifically, regression analysis helps one understand how the typical value of the dependent variable changes when any one of the independent variables is varied, while the other independent variables are held fixed. Regression techniques may be used to generate sequence activity models from training sets comprising multiple observations, which may contain sequence and activity information.

Partial Least Squares or PLS is a family of methods that finds a linear regression model by projecting predicted variables (e.g., activities) and the observable variables (e.g., sequences) to a new space. PLS is also known as projection to latent structures. Both the X (independent variables) and Y (dependent variables) data are projected to new spaces. PLS is used to find the fundamental relations between two matrices (X and Y). A latent variable approach is used to model the covariance structures in the X and Y spaces. A PLS model will try to find the multidimensional direction in the X space that explains the maximum multidimensional variance direction in the Y space. PLS regression is particularly suited when the matrix of predictors has more variables than observations, and when there is multicollinearity among X values.

A "descriptor" refers to something that serves to describe or identify an item. For example, characters in a character string can be descriptors of amino acids in a polypeptide being represented by the character string.

In a regression model, the dependent variable is related to independent variables by a sum of terms. Each term includes a product of an independent variable and an associated regression coefficient. In the case of a purely linear regression model, the regression coefficients are given by β in the following form of expression:

$$y_i = \beta_1 x_{i1} + \ldots + \beta_p x_{ip} + \epsilon_i = x_i^T \beta + \epsilon_i$$

where $y_i$ is the dependent variable, the $x_i$ are the independent variables, $\epsilon_i$ is the error variable, and T denotes the transpose, that is the inner product of the vectors $x_i$ and $\beta$.

"Principal component regression" (PCR) refers to a regression analysis that uses principal component analysis when estimating regression coefficients. In PCR instead of regressing the dependent variable on the independent variables directly, the principal components of the independent variables are used. PCR typically only uses a subset of the principal components in the regression.

"Principal component analysis" (PCA) refers to a mathematical procedure that uses an orthogonal transformation to convert a set of observations of possibly correlated variables into a set of values of linearly uncorrelated variables called principal components. The number of principal components is less than or equal to the number of original variables. This transformation is defined in such a way that the first principal component has the largest possible variance (that is, accounts for as much of the variability in the data as possible), and each succeeding component in turn has the highest variance possible under the constraint that it be orthogonal to (i.e., uncorrelated with) the preceding components.

"Neural network" is a model containing an interconnected group of processing elements or "neurons" that process information using a connectionist approach to computation. Neural networks are used to model complex relationships between inputs and outputs or to find patterns in data. Most neural networks process data in a non-linear, distributed, parallel fashion. In most cases a neural network is an adaptive system that changes its structure during a learning phase. Functions are performed collectively and in parallel by the processing elements, rather than there being a clear delineation of subtasks to which various units are assigned.

Generally, a neural network involves a network of simple processing elements that exhibit complex global behavior determined by the connections between the processing elements and element parameters. Neural networks are used with algorithms designed to alter the strength of the connections in the network to produce a desired signal flow. The strength is altered during training or learning.

"Random forest" refers to a combination of classification tree predictors such that each tree depends on the values of a random vector sampled independently and with the same distribution for all trees in the forest. A random forest is a learning ensemble consisting of a bagging of un-pruned decision tree learners with a randomized selection of features at each split of the decision tree. A random forest grows a large number of classification trees, each of which votes for the most popular class. The random forest then classifies a variable by taking the most popular voted class from all the tree predictors in the forest.

"Prior probability distribution", or "prior," of an uncertain quantity p is the probability distribution that expresses the uncertainty about p before data of interest (e.g., a training set of protein sequences) are taken into account. The unknown quantity may be a parameter, coefficient, variable, latent variable, or the like (e.g., a coefficient in a multiple regression model).

"Posterior probability distribution," or "posterior," of an uncertain quantity p is the probability distribution that expresses the uncertainty about p after the data of interest are taken into account.

The term "Bayesian linear regression" refers to an approach to linear regression in which the statistical analysis is undertaken within the context of Bayesian inference. The prior belief about the linear regression model, including the prior probability distribution function of the model's parameter, is combined with the data's likelihood function according to Bayes theorem to yield the posterior probability distribution about the parameters.

"Overfitting" refers to a condition that occurs when a statistical model describes random error or noise instead of the underlying relationship. Overfitting generally occurs when a model is excessively complex, such as having too many parameters relative to the number of observations. A model which has been overfit will generally have poor predictive performance, as it can exaggerate minor fluctuations in the data.

The term "base model" is used in reference to a sequence-activity model provided at the beginning of a process of improving a model.

The term "updated model" is used in reference to a sequence-activity model that is derived directly or indirectly from a base model, which has improved predictive power compared to the base model and/or another model from which it is derived from.

A "likelihood function" or "likelihood" of a model is a function of the parameters of a statistical model. The likelihood of a set of parameter values given some observed outcomes equals to the probability of those observed outcomes given those parameter values, i.e., $L(\theta|x)=P(x|\theta)$.

"Monte Carlo simulations" are simulations that rely on a large number of random sampling to obtain numerical results that simulate a real phenomenon. For instance, drawing a large number of pseudo-random uniform variables from the interval (0,1], and assigning values less than or equal to 0.50 as heads and greater than 0.50 as tails, is a Monte Carlo simulation of the behavior of repeatedly tossing a coin.

A "Metropolis algorithm" or "Metropolis-Hastings algorithm" is a Markov chain Monte Carlo (MCMC) method for obtaining a sequence of random samples from a probability distribution for which direct sampling is difficult. This sampling sequence can be used to approximate the distribution (i.e., to generate a histogram), or to compute an integral (such as an expected value). Metropolis-Hastings and other MCMC algorithms are generally used for sampling from multi-dimensional distributions, especially when the number of dimensions is high. The objective of the Metropolis-Hastings algorithm is to asymptotically generate states x according to a desired distribution P(x) and uses a stochastic process to fulfill it. The idea of the algorithm is to condition the stochastic process such that it asymptotically converges to the unique distribution P(x).

A "Markov chain" is a sequence of random variables $X_1$, $X_2$, $X_3$ . . . with the Markov property. In other words, given the present state, the future and past states are independent. Formally, $$Pr(X_{n+1}=x|X_1=x_1,X_2=x_2, \ldots ,X_n=x_n)= Pr(X_{n+1}=x|X_n=x_n).$$

The possible values of $X_i$ form a countable set S called the state space of the chain. A "Markov chain" system is a mathematical system that undergoes transitions from one state to another, between a finite or countable number of possible states. It is a random process usually characterized as memoryless: the next state depends only on the current state and not on the sequence of events that preceded it.

The "Akaike Information Criterion" (AIC) is a measure of the relative goodness of fit of a statistical model, and it is often used as a criterion for model selection among a finite set of models. The AIC is grounded in the concept of information entropy, in effect offering a relative measure of the information lost when a given model is used to describe reality. It can be said to describe the tradeoff between bias and variance in model construction, or loosely speaking between accuracy and complexity of the model. The AIC can be calculated as: $AIC=-2 \log_e L+2k$, wherein L is the maximum likelihood of the function and k is the number of free parameters of the model to be estimated.

"Bayesian Information Criterion" is a criterion for model selection among a finite set of models, and is closely related to AIC. The BIC can be calculated as: $BIC=-2 \log_e L+k \log_e(n)$, wherein n is the number of data observations. As the number of observations increased, BIC often penalizes extra number of free parameters more heavily than AIC.

A "genetic algorithm" is a process that mimics evolutionary processes. Genetic algorithms (GAs) are used in a wide variety of fields to solve problems which are not fully characterized or too complex to allow full characterization, but for which some analytical evaluation is available. That is, GAs are used to solve problems which can be evaluated by some quantifiable measure for the relative value of a solution (or at least the relative value of one potential solution in comparison to another). In the context of the present disclosure, a genetic algorithm is a process for selecting or manipulating character strings in a computer, typically where the character string corresponds to one or more biological molecules (e.g., nucleic acids, proteins, or the like).

The term "genetic operation" (or "GO") refer to biological and/or computational genetic operations, wherein all changes in any population of any type of character strings (and thus in any physical properties of physical objects encoded by such strings) can be described as a result of random and/or predetermined application of a finite set of logical algebraic functions. Examples of GO include but are not limited to multiplication, crossover, recombination, mutation, ligation, fragmentation, etc.

"Ensemble model" is a model whose terms include all the terms of a group of models, wherein the ensemble model's coefficients of the terms are based on the weighted coefficients of the corresponding terms of the individual models of the group. The weighting of coefficients is based on the predictive power and/or fitness of the individual models.

II. Overview of the Process to Search for Improved Protein Variants

In a guided evolution approach to exploring protein sequences, sequence-activity models are used to guide the generation of protein variants. One aspect of the disclosure provides various methods for preparing sequence-activity models that are based on protein libraries and can be used to search for new and improved protein libraries. This section first provides an overview of the process for searching for new and improved proteins, and then provides further details on issues related to selecting a starting library, building a sequence-activity model, and using the model to guide exploration of new proteins.

This disclosure provides illustrative examples involving amino acid residue sequences and protein activities, but it is understood that the approach described herein can also be implemented for other biological sequences and activities. For instance, in various embodiments, a sequence can be a whole genome, whole chromosome, chromosome segment, collection of gene sequences for interacting genes, gene, nucleic acid sequence, protein, polysaccharide, etc. In one or more embodiments, the sub-units of the sequences can be chromosomes, chromosome segments, haplotypes, genes, nucleotides, codons, mutations, amino acids, mono, di, tri, or oligomeric carbohydrates, etc.

Typically, at the beginning of a particular round of directed evolution of sequences, a training set of sequenced and assayed protein variants are obtained. A given round of directed evolution produces a number of variant proteins that vary by one or more mutations from the parent peptide or peptides used at the beginning of the round of directed evolution. The variant peptides produced during a round of directed evolution are assayed for activity. Those peptides having desired activity and/or improved activity compared to the parent peptide(s) are selected for use in at least one further round of directed evolution.

Sequenced and assayed protein variants may also be used to produce a sequence-activity model. Typically, they are used in a sequence-activity model if in fact they are sequenced. Each of the sequenced and assayed protein variants is referred to as an "observation." Generally, the more observations employed to create a sequence-activity model, the better the predictive power of that sequence-activity model.

Until the advent of next-generation massively parallel sequencing technology, it was difficult to economically sequence more than 10 to 30 variant peptides produced in any round of directed evolution. Now with the application of next-generation sequencing, many more variant proteins produced in a round of directed evolution can be sequenced. As a consequence, a much greater pool of training set data can be used to produce sequence-activity models. The sequence-activity models can now be generated using a training set that includes not only the top performing peptides from a round, but also some peptides which would not be of interest for further rounds of directed evolution, but whose sequence activity information could be applied to produce a more robust sequence-activity model.

In some embodiments, it is generally desirable to produce sequence-activity models having a good ability to predict the activity of an arbitrary sequence. The predictive power may be characterized by the accuracy of the prediction as well as the consistency with which the model accurately predicts activity. Further, a model may be characterized by its ability to accurately predict activity over a wide range of sequence space. For instance, the predictive power can be characterized in terms of residuals between the calculated and actual activities for a given test and/or validation set of peptides. A model with higher generalized predictive power tends to yield smaller and more consistent residuals across different sets of validation data. A model that is overfitted to a test set of data tends to yield larger and less consistent residuals for validation data, as shown by an example below. One aspect of the disclosure provides a method to efficiently find a model with high predictive power across different sets of data.

Sequence-activity models as described herein may be used to assist in identifying one or more parent "genes" in an initial variant library to undergo directed evolution. After a round of evolution is performed, a new variant library is identified, providing a new set of observations, which can then be fed back as data to prepare a new or refined sequence-activity model. This process of alternating between preparing a sequence-activity model based on new observations and conducting directed evolution based on the sequence-activity model may form an iterative loop of modeling-exploring, which may be repeated until desired proteins and libraries are obtained.

Because of the feedback loop between sequence-activity models and variant libraries, better models and better variant libraries depend on each other in exploration of proteins with improved activities. Therefore, bottle necks and improvements in either modeling and/or sequencing domains may affect both domains. In some embodiments of the invention, improvements of modeling efficiencies due to better modeling techniques provide better models to guide sequence exploration. In some embodiments, next generation sequencing technologies are used to improve sequencing speed in vitro, as well as to provide cross validation data to improve in silico computational models.

In some embodiments of the invention, useful sequence-activity models require robust mathematical modeling techniques and a large number of "observations." These observations are data provided in a training set for a model. Specifically, each observation is an activity value and an associated sequence for a variant in a library. Historically, sequencing has been a limiting step in the development of large training sets and consequently, increasingly robust sequence-activity models. In methods commonly used currently, variant libraries having perhaps hundreds of variants are generated. However, only a small fraction of these variants is actually sequenced. In a typical round of directed evolution, only about 10 to 30 variants with the highest activity are actually sequenced. Ideally, a much larger fraction of the variants in the library would be sequenced, including some variants with relatively low activities. Next generation sequencing tools have greatly improved sequencing speed, making it possible to include the low activity and high activity variants in a training set. In some embodiments, inclusion of variants having a range of activity levels results in production of models that perform better and/or are better at predicting activity over a wider range of sequence and activity space.

Some non-interaction sequence-activity models referred to herein include individual residues as independent variables to predict any activity of interest. The non-interaction sequence-activity models do not include terms to account for the interactions between two or more residuals. If an interaction between two of the residuals has a synergistic effect on activity, a non-interaction or linear model may provide an artificially inflated value of the coefficients associated with the two interacting residues. As a consequence, someone working with the model may erroneously conclude that by simply making a residue substitution as proposed by the relatively high value of the coefficient, the activity of a resulting peptide would be higher than expected. This is because the researcher does not understand from using a non-interaction or linear model that the increased activity associated with the residue substitution is primarily a result of that substitution's interaction with another substitution. If the researcher understood the importance of this interaction, then he or she could make both substitutions concurrently and achieve the increase in activity suggested by the interaction model.

If two residues interact to suppress activity in a nonlinear fashion, the non-interaction model ascribes lower values to the coefficients associate with these residues than would be appropriate if the residues were considered purely in isolation from one another. In other words, making one of the substitutions but not the other for the interacting residues will produce a result in activity that is greater than would be suggested by the non-interaction or linear model.

As a non-interaction model can be inadequate when residue-residue interactions have strong impact on activity, interaction models with interaction terms accounting for the interactions among residues are often necessary for accurate predictions of activity. However, models that utilize interaction terms pose computational and empirical challenges. Most notably, there are a great many potential interaction terms to take into consideration in developing/utilizing a model, which requires a considerable amount of computation. A much bigger limitation is the potential number of observations necessary to produce a model with a significant number of residue-residue interaction terms. Additionally, there may be a tendency for the model creation technique to over fit the data, given a particular number of available observations. To address this challenge, carefully selecting and limiting the interaction terms provided in the sequence-activity model is an important consideration in the development of many models.

Figure 1B:
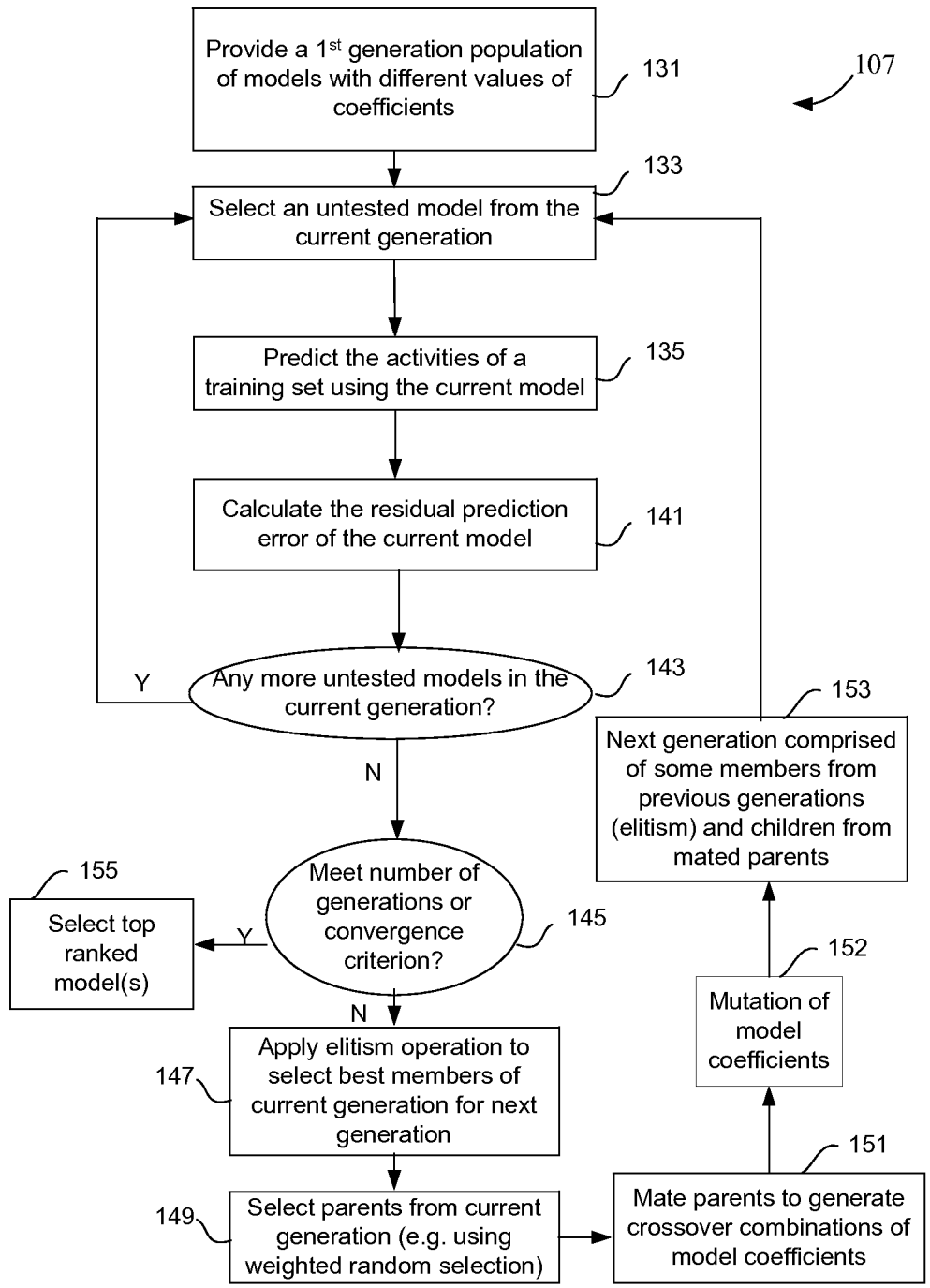
FIG. 1B is a flow chart depicting a genetic algorithm for fitting a multiplicative sequence-activity model to observed data in accordance with an embodiment of this invention.

FIG. 1 presents a flow chart showing one implementation of a process of preparing a sequence-activity model. As depicted, a process 100 begins at a block 103 to provide sequence and activity data for variant genes or proteins ("observations"). The sequence data can be taken from, for instance, a training set comprising residue sequences for an initial or improved protein variant library. Typically, these data include complete or partial residue sequence information, together with an activity value for each protein in the library. In some cases, multiple types of activities (e.g., rate constant data and thermal stability data) are provided together in the training set. Other data sources may be considered as well, as determined by the desired results. Some suitable data sources include, but are not limited to, literature references that describe information on particular peptides of relevance to the sequence activity model under construction. Additional information sources include, but are not limited to, earlier or different rounds of directed evolution in the same project. Indeed, it is intended that information derived from previous rounds of directed evolution (using any suitable method, including but not limited to those provided herein) will find use in the development of later produced libraries, variants, etc.

In many embodiments, the individual members of the protein variant library represent a wide range of sequences and activities. This facilitates the generation of a sequence-activity model that is applicable over a broad region of sequence space. Techniques for generating such diverse libraries include, but are not limited to, systematic variation of protein sequences and directed evolution techniques, as described herein. However, in some alternative embodiments, it is desirable to generate models from gene sequences in a particular gene family (e.g., a particular kinase found in multiple species or organisms). As many residues will be identical across all members of the family, the model describes only those residues that vary. Thus, in some embodiments, statistical models based on such relatively small training sets, compared to the set of all possible variants, are valid in a local sense. Namely, the models are valid only for the given observations of the given variants. In some embodiments, the goal is not to find a global fitness function, as it is recognized that in some models, this is beyond the capacity and/or need of the model system(s) under consideration.

Activity data may be obtained using any suitable means known in the art, including but not limited to assays and/or screens appropriately designed to measure magnitudes of the activity/activities of interest. Such techniques are well known and are not essential to the current invention. The principles for designing appropriate assays or screens are widely understood and known in the art. Techniques for obtaining protein sequences are also well known and are not key to the current invention. As mentioned, next-generating sequencing technologies may be used. In some embodiments, the activity of interest may be protein stability (e.g., thermal stability). However, many important embodiments consider other activities such as catalytic activity, resistance to pathogens and/or toxins, therapeutic activity, toxicity, and the like. Indeed, it is not intended that the present invention be limited to any particular assay/screening method(s) and/or sequencing method(s), as any suitable method known in the art finds use in the present invention.

After the training set data have been generated or acquired, the process uses it to generate a base sequence-activity model that predicts activity as a function of sequence information. See block 105. This model is an expression, algorithm or other tool that predicts the relative activity of a particular protein when provided with sequence information for that protein. In other words, protein sequence information is input and an activity prediction is output.

In some embodiments, each of the models includes a product of multiple multiplicative terms, each of the multiplicative terms reflecting the contribution to activity of a defined residue of a specific type at a specific sequence location. In other embodiments, each model includes the sum of multiple terms, each of the multiplicative terms reflecting the contribution to activity of a defined residue of a specific type at a specific sequence location.

In some embodiments, the base model does not include any interaction terms. In such cases, the base model may be described as a linear or non-interaction model. In other embodiments, the base model includes all available interaction terms, in which case the base model may be described as a non-linear or interaction model.

For many embodiments, the base model can rank the contribution of various residues to activity. Methods of generating such models, which all fall under the rubric of machine learning, (e.g., partial least squares regression (PLS), principal component regression (PCR), and multiple linear regression (MLR), Bayesian linear regression) are discussed below, along with the format of the independent variables (sequence information), the format of the dependent variable(s) (activity), and the form of the model itself (e.g., a linear first order expression, or a product of multiple terms, or a hybrid of both multiplicative and additive combination of terms).

After a base sequence activity model is generated, the process refines the model by adjusting the values of the coefficients in the terms of the models to minimize the residual error between the model prediction and the observed data. See block 107. This kind of adjustment is also referred to as model fitting. Various methods of model fitting known in the art can be used. For instance, a genetic algorithm can be used to adjust the values of the coefficients. For additive models, various regression techniques can be used to fit the model.

In some embodiments of the invention, the process also refines the model by selecting the appropriate terms to include in or exclude from the model, so as to minimize residual errors and/or to improve the model's predictive power. See block 107. Since the models considered have terms all selected from the same pool of terms, this refining process is also known as model selection among nested models. Some embodiments of the invention use a genetic algorithm to select the appropriate terms. Additionally or alternatively, some embodiments of the invention iteratively adds or subtracts interaction terms from a pool of available interaction terms to or from the base model and evaluates the resulting new models for improvement over the base model to produce a final model. When the base model includes all available interaction terms, the process subtracts such terms in a step-wise manner. When the base model includes no interaction terms, the process adds such terms in a step-wise manner. Adjusting model coefficient values and selecting model terms to improve the predictive power of the models are both known as model optimization techniques.

In the model selection process, some embodiments of the invention provide methods that not only take the variance that a model accounts for given a set of data into consideration, but also the ability of the model to predict new data. In some embodiments, this model selection approach penalizes models having more coefficients/parameters than equivalent models having fewer coefficients/parameters to avoid over fitting the model to the given data set. Examples of selection methods include, but are not limited to, Akaike Information Criterion (AIC) and Bayesian Information Criterion (BIC), and variations thereof.

In a series of nested models, as in regression models with progressively more interaction terms (and associated coefficients) than a base model, more complex models provide equally good or better fits than simpler ones even if the extra coefficients are spurious, because the more complex model enjoys extra degrees of freedom. Certain embodiments of the present disclosure employ model selection methods that penalize more complex models to the extent that the gain in goodness of fit is more than offset by the cost of spurious parameters.

Exemplary algorithms for generating sequence-activity models according to the operations in blocks 105 and 107 are presented below. Such techniques include, but are not limited to, genetic algorithm and step-wise techniques that bias against inclusion of additional interaction terms in a model. However, it is not intended that the present disclosure be limited to these specific examples.

In one aspect, the present disclosure provides methods of conducting directed evolution, the method comprising: (a) obtaining sequence and activity data for each of a plurality of protein variants; (b) generating a sequence-activity model from the sequence and activity data for each of the plurality of protein variants, wherein the sequence-activity model comprises: (1) a product of multiple terms, wherein each of at least some of the terms comprises a coefficient representing the contribution to activity of a defined amino acid or nucleotide at a defined position in a protein or nucleic acid sequence, and (2) a dependent variable representing the activity of the protein variants; and (c) using the model to guide a round of directed evolution.

In some embodiments, using the model to guide a round of directed evolution involve selecting one or more mutations for a round of directed evolution by evaluating the coefficients of the terms of the sequence-activity model to identify one or more of the defined amino acids or nucleotides at the defined positions that contribute to the activity. The methods also involve preparing a plurality of oligonucleotides containing or encoding the one or more mutations selected above; and performing a round of directed evolution using the oligonucleotides prepared above.

In other embodiments, the methods also involve identifying a new protein or a new nucleic acid sequence comprising the one or more mutations selected above, and preparing and assaying the new protein or a protein encoded by the new nucleic acid sequence. In some embodiments, the method further include using the new protein or protein encoded by the new nucleic acid sequence as a starting point for further directed evolution.

In alternative embodiments, using the model to guide a round of directed evolution involves identifying a complete protein sequence based on the model's prediction of a whole sequence's activity instead of individual defined subunit's contribution to the sequence activity. The methods include applying multiple protein sequences or multiple amino acid sequences to the sequence-activity model and determining activity values predicted by the sequence-activity model for each of the multiple protein sequences or nucleic acid sequences. The methods also involve selecting a new protein sequence or a new nucleic acid sequence from among the multiple protein sequences or multiple amino acid sequences applied above by evaluating the activity values predicted by the sequence-activity model for the multiple sequences. The methods also involve preparing and assaying a protein having the new protein sequence or a protein encoded by the new nucleic acid sequence.

In other embodiments, the methods apply saturation mutagenesis techniques. The methods involve selecting one or more positions in the protein sequence or nucleic acid sequences by evaluating the coefficients of the terms of the sequence-activity model to identify one or more of the defined amino acids or nucleotides of specific types at specific sequence positions that contribute to the activity. The methods then perform saturation mutagenesis at the one or more positions identified.

In another aspect, the present disclosure provides methods for preparing a sequence-activity model that can assist in identifying biological molecules to affect a desired activity. In some embodiments, the method comprises: (a) receiving sequence and activity data for a plurality of biological molecules; (b) preparing a base model from the sequence and activity data, wherein the base model predicts activity as a function of the presence or absence of sub-units of the sequence; (c) preparing at least one new model by adding/subtracting at least one new interaction term to/from the base model, wherein the new interaction term represents the interaction between two or more interacting sub-units; (d) determining the ability of the at least one new model to predict activity as a function of the presence or absence of the sub-units; and (e) determining whether to add/subtract the new interaction term to/from the base model based on the ability of the at least one new model to predict activity as determined in (d) and with a bias against adding the new interaction term. The model derived can then be used in various applications, such as in directed evolution of protein libraries to identify proteins with desired biological activities and properties.

In some embodiments, wherein the method determines that the new interaction term should be added to the base model to produce an updated model, the method also includes: (f) repeating (c) using the updated model in place of the base model and adding/subtracting a different interaction term than the one added/subtracted in (c); and (g) repeating (d) and (e) using the updated model in place of the base model. In some embodiments, the method further includes: (h) repeating (f) and (g) using a further updated model.

After the observations for a training set are selected and a mathematical technique for producing the sequence-activity model is chosen, the base model is created. The base model is typically generated without regard for its predictive ability. It is simply produced in accordance with a defined procedure for producing a base model from the available observations (i.e., the observation set), as described herein. As stated above, the sequence models may describe various sequences, while in some embodiments, the models describe proteins. In the latter case, the base model is simply a non-interaction/linear model with a single term for each of the mutations present in the collection of peptides used to create the training set. In these embodiments, the base model does not include any terms representing interactions between residues in the peptides. In some embodiments, the base model does not include a separate term for each and every mutation present in the observation set.

In alternative approaches, the base model includes not only the terms describing each of the mutations in isolation, but additionally includes terms for all the potential interacting residues. In the extreme case, every conceivable interaction between the noted mutations is used in the base model. This includes a term for each and every pairwise interaction between mutations, as well as terms for each and every possible three residue interaction, as well as every possible four residue interaction, etc. Some embodiments include only the pairwise interactions or the pairwise interactions and the three-way interactions. A three-way interaction is an activity-affecting interaction between three distinct sub-units.

In one or more embodiments of the disclosure that use a simple non-interaction or linear model as the base model, subsequent efforts to improve the model include adding new terms representing distinct interactions. In alternative embodiments where the base model includes all the non-interaction and interaction terms, subsequent efforts to improve the model involves selectively removing some of the interaction terms.

In one or more embodiments of the invention, the process of improving the base model involves iteratively adding or subtracting interaction terms from the base model in determining whether the resulting model sufficiently improves the quality of the model. At each iteration, the predictive power of the current model is determined and compared to another model, e.g., the base model or the updated model.

In embodiments in which a measure of predictive power already takes into account the ability of a model to be generalized to other sets of data, that measure alone can determine whether a candidate model should be selected. For instance, a measure such as AIC or BIC takes both the model likelihood (or residual error) and the number of parameters into consideration. A "likelihood function" or "likelihood" of a model is a function of the parameters of a statistical model. The likelihood of a set of parameter values given some observed outcomes equals to the probability of those observed outcomes given those parameter values, i.e. $L(\theta|x)=P(x|\theta)$. An exemplary calculation of model likelihood is described in a section below. Measures such as AIC and BIC are biased against a model having more parameters if the model having more parameters captures the same amount of data variance as does a model having fewer parameters.

If a measure of predictive power only considers residual error, the magnitude of the improvement in residual error must be considered in order to determine whether or not to incorporate the change associated with the current iteration into the current best updated model. This may be accomplished by comparing the magnitude of the improvement against a threshold. If the magnitude is less than the threshold, the change under consideration in the current iteration is not accepted. If, alternatively, the magnitude of the improvement exceeds the threshold, then the change under consideration is incorporated into the updated model and the updated model serves as the new best model going forward for the remaining iterations.

In certain embodiments, each iteration considers the addition or subtraction of a single interaction term from the current best model under consideration. In the case when the base model contains only non-interaction terms, a pool of all available interaction terms can be considered. Each of these interaction terms is considered in succession until the process is completed and a final best model is obtained.

In some cases, upon determining that the process has effectively converged and further improvement is unlikely, the model generation process is terminated before all of the available interaction terms in the pool have been considered.

Figure 2:
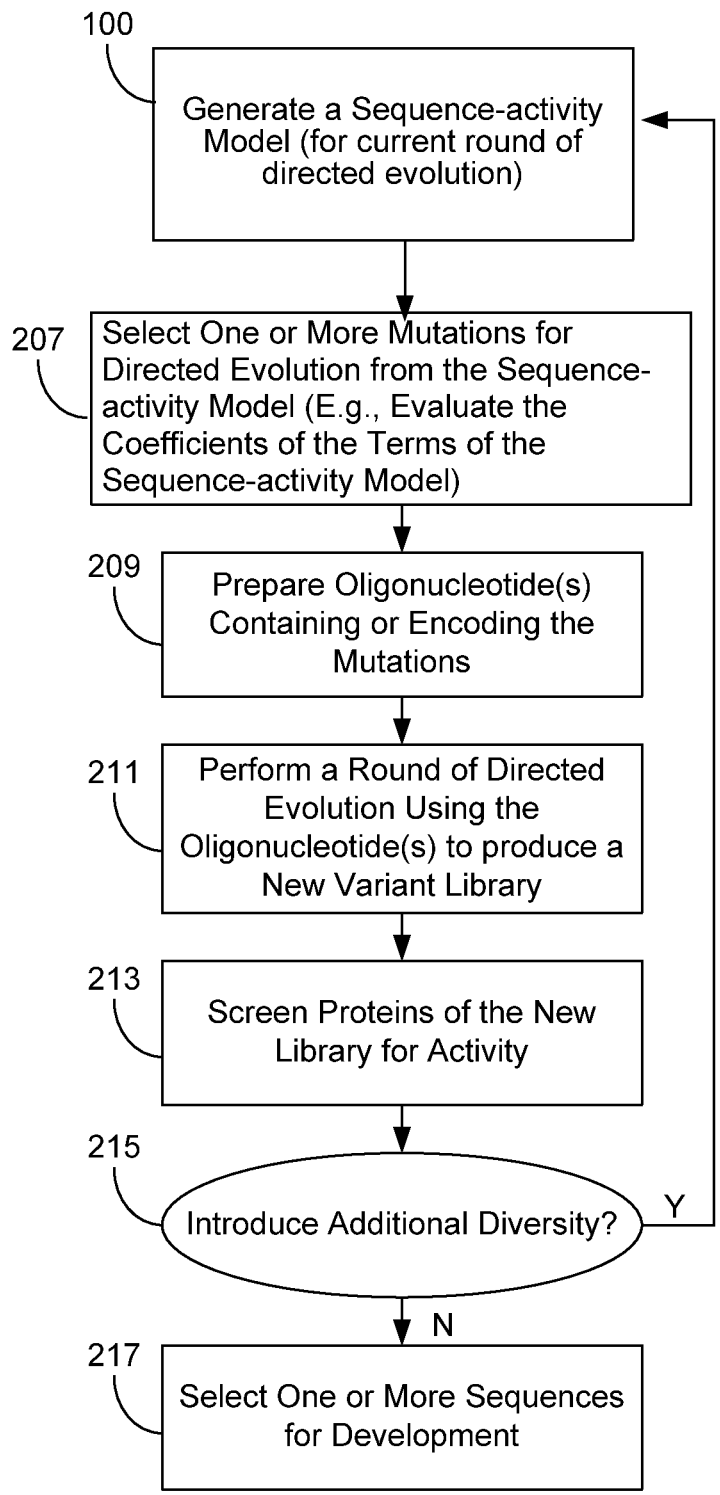
FIG. 2 is a flow chart depicting a process of directed evolution to generate one or more generations of protein variant libraries, wherein the operations use a multiplicative sequence-activity model such as one of those obtained in FIG. 1 to guide the generation of protein variant libraries. The generated variant libraries can provide sequence and activity data to prepare one or more new sequence-activity models.

FIG. 2 illustrates how a model can be used to iteratively guide the creation of new protein variant libraries for the purpose of exploring protein sequence and activity space, in a process (See, 200). In one example, after a final model is generated, the final model is employed to select mutations of multiple residue positions (e.g., position 35) or specific residue types (e.g. glutamine at position 35) that are predicted to impact activity. In some embodiments, the determination is based on the coefficients of the terms. See block 207. In addition to identifying such positions, the model may be used to "rank" the residue positions or residue types based on their contributions to activity, e.g. their coefficient values. This function is desired. For example, the model may predict that glutamine at position 35 has the most pronounced, positive effect on activity; phenylalanine at position 208 has the second most pronounced, positive effect on activity; and so on. In one specific approach described below, PLS or PCR regression coefficients are employed to rank the importance of specific residues. In another specific approach, a PLS load matrix is employed to rank the importance of specific residue positions.

Residues are selected using any of a number of different selection protocols, some of which are described below. In one illustrative example, specific residues predicted to have the most beneficial impact on activity are preserved (i.e., not varied). A certain number of other residues predicted to have a lesser impact are, however, selected for variation. In another illustrative example, the residue positions found to have the biggest impact on activity are selected for variation, but only if they are found to vary in high performing members of the training set. For example, if the model predicts that residue position 197 has the biggest impact on activity, but all or most of the proteins with high activity have leucine at this position, position 197 would not be selected for variation in this approach. In other words, all or most proteins in a next generation library would have leucine at position 197. However, if some "good" proteins had valine at this position and others had leucine, then the process would choose to vary the amino acid at this position. In some cases, it will be found that a combination of two or more interacting residues have the biggest impact on activity. Hence, in some strategies, these residues are co-varied. An example of covariation is to apply saturated mutagenesis at these residues simultaneously.

After the process has identified mutations, the process prepares oligonucleotides containing or encoding the mutations identified, as indicated at a block 209 (FIG. 2). Various methods may be employed to prepare the oligonucleotides. In some embodiments, the oligonucleotides are prepared by a sequence synthesizer.

After the residues for variation have been identified, the method next generates a new variant library having the specified residue variation. See block 211 (FIG. 2). Various methodologies are available for this purpose. In one example, an in vitro or in vivo recombination-based diversity generation mechanism is performed to generate the new variant library. Such procedures may employ oligonucleotides containing sequences or subsequences for encoding the proteins of the parental variant library. Some of the oligonucleotides will be closely related, differing only in the choice of codons for alternate amino acids selected for variation at 209. The recombination-based diversity generation mechanism may be performed for one or multiple cycles. If multiple cycles are used, each involves a screening step to identify which variants have acceptable performance to be used in a subsequent recombination cycle. This is a form of directed evolution. However, it is not intended that the present invention be limited to any specific method of recombination-based diversity generation method, as any suitable method/technique finds use in the present invention. In some embodiments, for example, the present invention performs saturation mutagenesis at individual sequence locations or combinations of sequence locations that interact, as indicated by the coefficient values of the non-interactive or interactive terms of the sequence-activity models.

In an additional illustrative example, a "reference" protein sequence is chosen and the residues selected at 207 of FIG. 2 are "toggled" to identify individual members of the variant library. The new proteins so identified are synthesized by an appropriate technique to generate the new library. In one example, the reference sequence may be a top-performing member of the training set or a "best" sequence predicted by a PLS or PCR model.

In another approach, the sequence activity model is used as a "fitness function" in a genetic algorithm for exploring sequence space. After one or more rounds of the genetic algorithm (with each round using the fitness function to select one or more possible sequences for a genetic operation), a next generation library is identified for use as described in this flow chart. In a very real sense this strategy can be viewed as in silico directed evolution. In an ideal case, if one had in hand an accurate, precise global or local fitness function one could perform all the evolution in silico and synthesize a single best variant for use in the final commercial or research application. Though this is likely to be impossible to achieve in most cases such a view of the process lends clarity to the goals and approach of using machine learning techniques for directed evolution.

In another illustrative example, residues for variation in a round of directed evolution are selected in a single parent sequence. The parent may be identified using model results from a prior round of directed evolution or by using data that identify the library member having the best assay performance. Oligonucleotides for the next round of directed evolution may be defined to include portions of the selected parent's backbone with one or more mutations predicted algorithmically from a sequence activity model for the current round. These oligonucleotides may be produced using any suitable means, including but not limited to synthetic methods.

After the new library has been produced, it is screened for activity, as indicated in a block 213 (FIG. 2). Ideally, the new library provides one or more members with better activity than was observed in the previous library. However, even without such an advantage, the new library can provide beneficial information. Its members may be employed for generating improved models that account for the effects of new variants, and thereby more accurately predict activity across wider regions of sequence space. Further, the library may represent a passage in sequence space from a local maximum toward a global maximum (e.g., in activity).

Depending on the goal of process 200 (FIG. 2), in some embodiments, it is desirable to generate a series of new protein variant libraries, with each one providing new members of a training set. The updated training set is then used to generate an improved model. To achieve the improved model, process 200 is shown with a decision operation as shown in block 215, which determines whether yet another protein variant library should be produced. Various criteria can be used to make this decision. Examples of decision criteria include but are not limited to the number of protein variant libraries generated so far, the activity of top proteins from the current library, the magnitude of activity desired, and the level of improvement observed in recent new libraries.

Assuming that the process is used to continue with a new library, the process returns to operation of block 100 (FIG. 2) where a new sequence-activity model is generated from sequence and activity data obtained for the current protein variant library. In other words, the sequence and activity data for the current protein variant library serves as part of the training set for the new model (or it may serve as the entire training set). Thereafter, operations shown in blocks 207, 209, 211, 213, and 215 (FIG. 2) are performed as described above, but with the new model.

When it is determined that the end-point of the method has been reached, the cycle illustrated in FIG. 2 is ended and no new library is generated. At that point, the process is either simply terminated or in some embodiments, one or more sequences from one or more of the libraries is/are selected for development and/or manufacture. See block 217.

III. Generating Observations

Protein variant libraries are groups of multiple proteins having one or more residues that vary from member to member in a library. These libraries may be generated using the methods described herein and/or any suitable means known in the art. These libraries find use in providing data for training sets used to generate sequence-activity models in accordance with various embodiments of the present invention. The number of proteins included in a protein variant library often depends on the application and the cost associated with their generation. It is not intended that the present invention be limited to any particular number of proteins in the protein libraries used in the methods of the present invention. It is further not intended that the present invention be limited to any particular protein variant library or libraries.

In one example, the protein variant library is generated from one or more naturally occurring proteins, which may be encoded by a single gene family. Other starting points including but not limited to recombinants of known proteins or novel synthetic proteins may be used. From these seed or starting proteins, the library may be generated by various techniques. In one case, the library is generated by DNA fragmentation-mediated recombination as described in Stemmer (1994) Proceedings of the National Academy of Sciences, USA, 10747-10751 and WO 95/22625 (both of which are incorporated herein by reference), synthetic oligonucleotide-mediated recombination as described in Ness et al. (2002) Nature Biotechnology 20:1251-1255 and WO 00/42561 (both of which are incorporated herein by reference), or nucleic acids encoding part or all of one or more parent proteins. Combinations of these methods may be used as well (e.g., recombination of DNA fragments and synthetic oligonucleotides) as well as other recombination-based methods described in, for example, WO97/20078 and WO98/27230, both of which are incorporated herein by reference. Any suitable methods used to generate protein variant libraries find use in the present invention. Indeed, it is not intended that the present invention be limited to any particular method for producing variant libraries.

In some embodiments, a single "starting" sequence (which may be an "ancestor" sequence) may be employed for purposes of defining a group of mutations used in the modeling process. In some embodiments, at least one of the starting sequence is a wild-type sequence.

In certain embodiments, the mutations are (a) identified in the literature as affecting substrate specificity, selectivity, stability, or other beneficial property and/or (b) computationally predicted to improve protein folding patterns (e.g., packing the interior residues of a protein), ligand binding, subunit interactions, family shuffling between multiple diverse homologs, etc. Alternatively, the mutations may be physically introduced into the starting sequence and the expression products screened for beneficial properties. Site directed mutagenesis is one example of a useful technique for introducing mutations, although any suitable method finds use. Thus, alternatively or in addition, the mutants may be provided by gene synthesis, saturating random mutagenesis, semi-synthetic combinatorial libraries of residues, directed evolution, recursive sequence recombination ("RSR") (See e.g., US Patent Application No. 2006/0223143, incorporated by reference herein in its entirety), gene shuffling, error-prone PCR, and/or any other suitable method. One example of a suitable saturation mutagenesis procedure is described in US Published Patent Application No. 20100093560, which is incorporated herein by reference in its entirety.

The starting sequence need not be identical to the amino acid sequence of the wild type protein. However, in some embodiments, the starting sequence is the sequence of the wild type protein. In some embodiments, the starting sequence includes mutations not present in the wild type protein. In some embodiments, the starting sequence is a consensus sequence derived from a group of proteins having a common property, e.g., a family of proteins.

A non-limiting representative list of families or classes of enzymes which may serve as sources of parent sequences includes, but is not limited to the following: oxidoreducatses (E.C.1); transferases (E.C.2); hydrolyases (E.C.3); lyases (E.C.4); isomerases (E.C. 5) and ligases (E.C. 6). More specific but non-limiting subgroups of oxidoreducatses include dehydrogenases (e.g., alcohol dehydrogenases (carbonyl reductases), xylulose reductases, aldehyde reductases, farnesol dehydrogenase, lactate dehydrogenases, arabinose dehydrogenases, glucose dehydrodgenase, fructose dehydrogenases, xylose reductases and succinate dehyrogenases), oxidases (e.g., glucose oxidases, hexose oxidases, galactose oxidases and laccases), monoamine oxidases, lipoxygenases, peroxidases, aldehyde dehydrogenases, reductases, long-chain acyl-[acyl-carrier-protein] reductases, acyl-CoA dehydrogenases, ene-reductases, synthases (e.g., glutamate synthases), nitrate reductases, mono and di-oxygenases, and catalases. More specific but non-limiting subgroups of transferases include methyl, amidino, and carboxyl transferases, transketolases, transaldolases, acyltransferases, glycosyltransferases, transaminases, transglutaminases and polymerases. More specific but non-limiting subgroups of hydrolases include ester hydrolases, peptidases, glycosylases, amylases, cellulases, hemicellulases, xylanases, chitinases, glucosidases, glucanases, glucoamylases, acylases, galactosidases, pullulanases, phytases, lactases, arabinosidases, nucleosidases, nitrilases, phosphatases, lipases, phospholipases, proteases, ATPases, and dehalogenases. More specific but non-limiting subgroups of lyases include decarboxylases, aldolases, hydratases, dehydratases (e.g., carbonic anhydrases), synthases (e.g., isoprene, pinene and farnesene synthases), pectinases (e.g., pectin lyases) and halohydrin dehydrogenases. More specific, but non-limiting subgroups of isomerases include racemases, epimerases, isomerases (e.g., xylose, arabinose, ribose, glucose, galactose and mannose isomerases), tautomerases, and mutases (e.g. acyl transferring mutases, phosphomutases, and aminomutases. More specific but non-limiting subgroups of ligases include ester synthases. Other families or classes of enzymes which may be used as sources of parent sequences include transaminases, proteases, kinases, and synthases. This list, while illustrating certain specific aspects of the possible enzymes of the disclosure, is not considered exhaustive and does not portray the limitations or circumscribe the scope of the disclosure.

In some cases, the candidate enzymes useful in the methods described herein are capable of catalyzing an enantioselective reaction such as an enantioselective reduction reaction, for example. Such enzymes can be used to make intermediates useful in the synthesis of pharmaceutical compounds for example.

In some embodiments, the candidate enzymes are selected from endoxylanases (EC 3.2.1.8); β-xylosidases (EC 3.2.1.37); alpha-L-arabinofuranosidases (EC 3.2.1.55); alpha-glucuronidases (EC 3.2.1.139); acetylxylanesterases (EC 3.1.1.72); feruloyl esterases (EC 3.1.1.73); coumaroyl esterases (EC 3.1.1.73); alpha-galactosidases (EC 3.2.1.22); beta-galactosidases (EC 3.2.1.23); beta-mannanases (EC 3.2.1.78); beta-mannosidases (EC 3.2.1.25); endo-polygalacturonases (EC 3.2.1.15); pectin methyl esterases (EC 3.1.1.11); endo-galactanases (EC 3.2.1.89); pectin acetyl esterases (EC 3.1.1.6); endo-pectin lyases (EC 4.2.2.10); pectate lyases (EC 4.2.2.2); alpha rhamnosidases (EC 3.2.1.40); exo-poly-alpha-galacturonosidase (EC 3.2.1.82); 1,4-alpha-galacturonidase (EC 3.2.1.67); exopolygalacturonate lyases (EC 4.2.2.9); rhamnogalacturonan endolyases EC (4.2.2.B3); rhamnogalacturonan acetylesterases (EC 3.2.1.B11); rhamnogalacturonan galacturonohydrolases (EC 3.2.1.B11); endo-arabinanases (EC 3.2.1.99); laccases (EC 1.10.3.2); manganese-dependent peroxidases (EC 1.10.3.2); amylases (EC 3.2.1.1), glucoamylases (EC 3.2.1.3), proteases, lipases, and lignin peroxidases (EC 1.11.1.14). Any combination of one, two, three, four, five, or more than five enzymes find use in the compositions of the present invention.

In one or more embodiments of the invention, a single starting sequence is modified in various ways to generate the library. In some embodiments, the library is generated by systematically varying the individual residues of the starting sequence. In one illustrative example, a design of experiment (DOE) methodology is employed to identify the systematically varied sequences. In another example, a "wet lab" procedure such as oligonucleotide-mediated recombination is used to introduce some level of systematic variation. It is not intended that the present invention be limited to any particular method for generating systematically varied sequences, as any suitable method finds use.

As used herein, the term "systematically varied sequences" refers to a set of sequences in which each residue is seen in multiple contexts. In principle, the level of systematic variation can be quantified by the degree to which the sequences are orthogonal from one another (i.e., maximally different compared to the mean). In some embodiments, the process does not depend on having maximally orthogonal sequences. However, the quality of the model will be improved in direct relation to the orthogonality of the sequence space tested. In a simple illustrative example, a peptide sequence is systematically varied by identifying two residue positions, each of which can have one of two different amino acids. A maximally diverse library includes all four possible sequences. Such maximal systematic variation increases exponentially with the number of variable positions; e.g., by $2^N$, when there are 2 options at each of N residue positions. Those having ordinary skill in the art will readily recognize that maximal systematic variation, however, is not required. Systematic variation provides a mechanism for identifying a relatively small set of sequences for testing that provides a good sampling of sequence space.

Protein variants having systematically varied sequences can be obtained in a number of ways using techniques that are well known to those of ordinary skill in the art. As indicated, suitable methods include, but are not limited to recombination-based methods that generate variants based on one or more "parental" polynucleotide sequences. Polynucleotide sequences can be recombined using a variety of techniques, including, for example, DNAse digestion of polynucleotides to be recombined followed by ligation and/or PCR reassembly of the nucleic acids. These methods include, but are not limited to those described in, for example, Stemmer (1994) Proceedings of the National Academy of Sciences USA, 91:10747-10751, U.S. Pat. No. 5,605,793, "Methods for In Vitro Recombination," U.S. Pat. No. 5,811,238, "Methods for Generating Polynucleotides having Desired Characteristics by Iterative Selection and Recombination," U.S. Pat. No. 5,830,721, "DNA Mutagenesis by Random Fragmentation and Reassembly," U.S. Pat. No. 5,834,252, "End Complementary Polymerase Reaction," U.S. Pat. No. 5,837,458, "Methods and Compositions for Cellular and Metabolic Engineering," WO98/42832, "Recombination of Polynucleotide Sequences Using Random or Defined Primers," WO 98/27230, "Methods and Compositions for Polypeptide Engineering," WO 99/29902, "Method for Creating Polynucleotide and Polypeptide Sequences," and the like, all of which are incorporated herein by reference.

Synthetic recombination methods are also particularly well suited for generating protein variant libraries with systematic variation. In synthetic recombination methods, a plurality of oligonucleotides are synthesized which collectively encode a plurality of the genes to be recombined. In some embodiments, the oligonucleotides collectively encode sequences derived from homologous parental genes. For example, homologous genes of interest are aligned using a sequence alignment program such as BLAST (See e.g., Atschul, et al., Journal of Molecular Biology, 215:403-410 (1990). Nucleotides corresponding to amino acid variations between the homologues are noted. These variations are optionally further restricted to a subset of the total possible variations based on covariation analysis of the parental sequences, functional information for the parental sequences, selection of conservative or non-conservative changes between the parental sequences, or other suitable criteria. Variations are optionally further increased to encode additional amino acid diversity at positions identified by, for example, covariation analysis of the parental sequences, functional information for the parental sequences, selection of conservative or non-conservative changes between the parental sequences, or apparent tolerance of a position for variation. The result is a degenerate gene sequence encoding a consensus amino acid sequence derived from the parental gene sequences, with degenerate nucleotides at positions encoding amino acid variations. Oligonucleotides are designed which contain the nucleotides required to assemble the diversity present in the degenerate gene. Details regarding such approaches can be found in, for example, Ness et al. (2002), Nature Biotechnology, 20:1251-1255, WO 00/42561, "Oligonucleotide Mediated Nucleic Acid Recombination," WO 00/42560, "Methods for Making Character Strings, Polynucleotides and Polypeptides having Desired Characteristics," WO 01/75767, "In Silico Cross-Over Site Selection," and WO 01/64864, "Single-Stranded Nucleic Acid Template-Mediated Recombination and Nucleic Acid Fragment Isolation," each of which is incorporated herein by reference. The identified polynucleotide variant sequences may be transcribed and translated, either in vitro or in vivo, to create a set or library of protein variant sequences.

The set of systematically varied sequences can also be designed a priori using design of experiment (DOE) methods to define the sequences in the data set. A description of DOE methods can be found in Diamond, W. J. (2001) Practical Experiment Designs: for Engineers and Scientists, John Wiley & Sons and in "Practical Experimental Design for Engineers and Scientists" by William J Drummond (1981) Van Nostrand Reinhold Co New York, "Statistics for experimenters" George E. P. Box, William G Hunter and J. Stuart Hunter (1978) John Wiley and Sons, New York, or, e.g., on the world wide web at itl.nist.gov/div898/handbook/. There are several computational packages available to perform the relevant mathematics, including Statistics Toolbox (MATLAB®), JMP®, STATISTICA®, and STAT-EASE® DESIGN EXPERT®. The result is a systematically varied and orthogonal dispersed data set of sequences that is suitable for building the sequence-activity model of the present invention. DOE-based data sets can also be readily generated using either Plackett-Burman or Fractional Factorial Designs, as known in the art. Diamond, W. J. (2001).

In engineering and chemical sciences, fractional factorial designs are used to define fewer experiments as compared to full factorial designs. In these methods, a factor is varied (i.e., "toggled") between two or more levels. Optimization techniques are used to ensure that the experiments chosen are maximally informative in accounting for factor space variance. The same design approaches (e.g., fractional factorial, D-optimal design) can be applied in protein engineering to construct fewer sequences where a given number of positions are toggled between two or more residues. In some embodiments, this set of sequences provides an optimal description of systematic variance present in the protein sequence space in question.

An illustrative example of the DOE approach applied to protein engineering includes the following operations:

1) Identify positions to toggle based on the principles described herein (e.g., present in parental sequences, level of conservation, etc.)
2) Create a DOE experiment using one of the commonly available statistical software packages by defining the number of factors (i.e., variable positions), the number of levels (i.e., choices at each position), and the number of experiments to run to provide an output matrix. The information content of the output matrix (typically consisting of 1s and 0s that represent residue choices at each position) depends directly on the number of experiments to run (typically, the more the better).
3) Use the output matrix to construct a protein alignment that codes the 1s and 0s back to specific residue choices at each position.
4) Synthesize the genes encoding the proteins represented in the protein alignment.
5) Test the proteins encoded by the synthesized genes in relevant assay(s).
6) Build a model based on the tested genes/proteins.
7) Follow the steps described herein to identify positions of importance and to build one or more subsequent libraries with improved fitness.

In an illustrative example, a protein in which the functionally best amino acid residues at 20 positions are to be determined (e.g., where there are 2 possible amino acids available at each position) is investigated. In this example, a resolution IV factorial design would be appropriate. A resolution IV design is defined as a design that is capable of elucidating the effects of all single variables, with no two-factor effects overlapping them. The design would then specify a set of 40 specific amino acid sequences covering the total diversity of $2^{20}$ (~1 million) possible sequences. These sequences are then generated using any standard gene synthesis protocol and the function and fitness of these clones is determined.

An alternative to the above approaches is to employ some or all available sequences (e.g., the GENBANK® database and other public sources) to provide the protein variant library. This approach provides an indication of sequence space regions of interest.

IV. Sequencing Methods

Historically, sequencing has been a limiting step in the development of large training sets and consequently, increasingly robust sequence-activity models. The high cost and long time required to sequence variants limited the number of observations to a few tens of variants. Next generation sequencing tools have greatly reduced cost and increased sequencing speed and volume, making it possible to include both low and high activity variants in a training set.

Next-generation sequencing tools can inexpensively sequence large numbers of base pairs (e.g., at least about 1,000,000,000 base pairs) in one run. This capacity can be utilized when sequencing variant proteins, which are typically only a few kilobase pairs in length, in a single run. Often next-generation sequencing tools are optimized for sequencing single large genomes (e.g., the human genome) rather than many smaller sequences in a single run. To realize the potential of next-generation sequencing tools for sequencing many observations in parallel, the origin of each of the observations being sequenced in a single run should be uniquely identified. In some embodiments, bar-coded sequences are used on each and every fragment fed to a next-generation sequencer for a single run. In one example, barcodes uniquely identify a particular well on a particular plate (e.g., 96 well plates). In some of these embodiments, each well of each plate contains a single unique variant. By barcoding each variant, or more specifically each fragment of each variant, the gene sequences of multiple different variants can be sequenced and identified in a single run. In the process, all fragment reads having the same barcode are identified and processed together by the algorithm identifying length sequences for the variants.

In some embodiments, the DNA from the cells of a variant in a given well is extracted and then fragmented. The fragments are then bar-coded to identify at least the well, and sometimes the well and plate associated with that variant. The resulting fragments are then size selected to produce sequences of appropriate length for the next-generation sequencer. In one illustrative example, the read lengths are about 200 base pairs. In some embodiments, the plate barcode is not applied until after the DNA fragments from the various wells of a plate are first pooled. The pooled DNA is then bar-coded to identify the plate. In some embodiments, each fragment, regardless of which well it is derived from, will have the same plate barcode. However, in some alternative embodiments, the fragments have different barcodes. In addition, the well and plate barcodes may be applied to identify the DNA extracted from a given well.

In one or more embodiments, sequence data can be obtained using bulk sequencing methods including, for example, Sanger sequencing or Maxam-Gilbert sequencing, which are considered the first generation sequencing methods. Sanger sequencing, which involves using labeled dideoxy chain terminators, is well known in the art; see, e.g., Sanger et al., Proceedings of the National Academy of Sciences of the United States of America 74, 5463-5467 (1997). Maxam-Gilbert sequencing, which involves performing multiple partial chemical degradation reactions on fractions of the nucleic acid sample followed by detection and analysis of the fragments to infer the sequence, is also well known in the art; see, e.g., Maxam et al., Proceedings of the National Academy of Sciences of the United States of America 74, 560-564 (1977). Another bulk sequencing method is sequencing by hybridization, in which the sequence of a sample is deduced based on its hybridization properties to a plurality of sequences, e.g., on a microarray or gene chip; see, e.g., Drmanac, et al., Nature Biotechnology 16, 54-58 (1998).

In one or more embodiments, sequence data is obtained using next-generation sequencing methods. Next-generation sequencing is also referred to as "high-throughput sequencing". The techniques parallelize the sequencing process, producing thousands or millions of sequences at once. Examples of suitable next-generation sequencing methods include, but are not limited to, single molecule real-time sequencing (e.g., Pacific Biosciences, Menlo Park, Calif.), ion semiconductor sequencing (e.g., Ion Torrent, South San Francisco, Calif.), pyrosequencing (e.g., 454, Branford, Conn.), sequencing by ligation (e.g., SOLid sequencing of Life Technologies, Carlsbad, Calif.), sequencing by synthesis and reversible terminator (e.g., lumina, San Diego, Calif.), nucleic acid imaging technologies such as transmission electron microscopy, and the like.

In general, next-generation sequencing methods typically use an in vitro cloning step to amplify individual DNA molecules. Emulsion PCR (emPCR) isolates individual DNA molecules along with primer-coated beads in aqueous droplets within an oil phase. PCR produces copies of the DNA molecule, which bind to primers on the bead, followed by immobilization for later sequencing. emPCR is used in the methods by Marguilis et al. (commercialized by 454 Life Sciences, Branford, Conn.), Shendure and Porreca et al. (also known as "polony sequencing") and SOLiD sequencing, (Applied Biosystems Inc., Foster City, Calif.). See M. Margulies, et al. (2005) "Genome sequencing in microfabricated high-density picoliter reactors" Nature 437: 376-380; J. Shendure, et al. (2005) "Accurate Multiplex Polony Sequencing of an Evolved Bacterial Genome" Science 309 (5741): 1728-1732. In vitro clonal amplification can also be carried out by "bridge PCR," where fragments are amplified upon primers attached to a solid surface. Braslaysky et al. developed a single-molecule method (commercialized by Helicos Biosciences Corp., Cambridge, Mass.) that omits this amplification step, directly fixing DNA molecules to a surface. I. Braslaysky, et al. (2003) "Sequence information can be obtained from single DNA molecules" Proceedings of the National Academy of Sciences of the United States of America 100: 3960-3964.

DNA molecules that are physically bound to a surface can be sequenced in parallel. In "sequencing by synthesis," a complementary strand is built based on the sequence of a template strand using a DNA polymerase like dye-termination electrophoretic sequencing, Reversible terminator methods (commercialized by Illumina, Inc., San Diego, Calif. and Helicos Biosciences Corp., Cambridge, Mass.) use reversible versions of dye-terminators, adding one nucleotide at a time, and detect fluorescence at each position in real time, by repeated removal of the blocking group to allow polymerization of another nucleotide. "Pyrosequencing" also uses DNA polymerization, adding one nucleotide at a time and detecting and quantifying the number of nucleotides added to a given location through the light emitted by the release of attached pyrophosphates (commercialized by 454 Life Sciences, Branford, Conn.). See M. Ronaghi, et al. (1996). "Real-time DNA sequencing using detection of pyrophosphate release" Analytical Biochemistry 242: 84-89.

Specific examples of next-generation sequencing methods are described in further details below. One or more implementations of the current invention may use one or more of the following sequencing methods without deviating from the principles of the invention.

Single molecule real time sequencing (also known as SMRT) is a parallelized single molecule DNA sequencing by synthesis technology developed by Pacific Biosciences. Single molecule real time sequencing utilizes the zero-mode waveguide (ZMW). A single DNA polymerase enzyme is affixed at the bottom of a ZMW with a single molecule of DNA as a template. The ZMW is a structure that creates an illuminated observation volume that is small enough to observe only a single nucleotide of DNA (also known as a base) being incorporated by DNA polymerase. Each of the four DNA bases is attached to one of four different fluorescent dyes. When a nucleotide is incorporated by the DNA polymerase, the fluorescent tag is cleaved off and diffuses out of the observation area of the ZMW where its fluorescence is no longer observable. A detector detects the fluorescent signal of the nucleotide incorporation, and the base call is made according to the corresponding fluorescence of the dye.

Another single molecule sequencing technology applicable is the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

Ion Semiconductor Sequencing is a method of DNA sequencing based on the detection of hydrogen ions that are released during the polymerization of DNA. This is a method of "sequencing by synthesis," during which a complementary strand is built based on the sequence of a template strand. A microwell containing a template DNA strand to be sequenced is flooded with a single species of deoxyribonucleotide triphosphate (dNTP). If the introduced dNTP is complementary to the leading template nucleotide, it is incorporated into the growing complementary strand. This causes the release of a hydrogen ion that triggers an ISFET ion sensor, which indicates that a reaction has occurred. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. Ion semiconductor sequencing may also be referred to as ion torrent sequencing, pH-mediated sequencing, silicon sequencing, or semiconductor sequencing.

In pyrosequencing, the pyrophosphate ion released by the polymerization reaction is reacted with adenosine 5' phosphosulfate by ATP sulfurylase to produce ATP; the ATP then drives the conversion of luciferin to oxyluciferin plus light by luciferase. As the fluorescence is transient, no separate step to eliminate fluorescence is necessary in this method. One type of deoxyribonucleotide triphosphate (dNTP) is added at a time, and sequence information is discerned according to which dNTP generates significant signal at a reaction site. The commercially available Roche GS FLX instrument acquires sequence using this method. This technique and applications thereof are discussed in detail, for example, in Ronaghi et al., Analytical Biochemistry 242, 84-89 (1996) and Margulies et al. Nature 437, 376-380 (2005) (corrigendum at Nature 441, 120 (2006)). A commercially available pyrosequencing technology is 454 sequencing (Roche) (e.g. as described in Margulies, M. et al. Nature 437:376-380 [2005]).

In ligation sequencing, a ligase enzyme is used to join a partially double-stranded oligonucleotide with an overhang to the nucleic acid being sequenced, which has an overhang; in order for ligation to occur, the overhangs must be complementary. The bases in the overhang of the partially double-stranded oligonucleotide can be identified according to a fluorophore conjugated to the partially double-stranded oligonucleotide and/or to a secondary oligonucleotide that hybridizes to another part of the partially double-stranded oligonucleotide. After acquisition of fluorescence data, the ligated complex is cleaved upstream of the ligation site, such as by a type its restriction enzyme, for example, Bbvl, which cuts at a site a fixed distance from its recognition site (which was included in the partially double stranded oligonucleotide). This cleavage reaction exposes a new overhang just upstream of the previous overhang, and the process is repeated. This technique and applications thereof are discussed in detail, for example, in Brenner et al., Nature Biotechnology 18, 630-634 (2000). In some embodiments, ligation sequencing is adapted to the methods of the invention by obtaining a rolling circle amplification product of a circular nucleic acid molecule, and using the rolling circle amplification product as the template for ligation sequencing.

A commercially available example of ligation sequencing technology is the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In reversible terminator sequencing, a fluorescent dye-labeled nucleotide analog that is a reversible chain terminator due to the presence of a blocking group is incorporated in a single-base extension reaction. The identity of the base is determined according to the fluorophore; in other words, each base is paired with a different fluorophore. After fluorescence/sequence data is acquired, the fluorophore and the blocking group are chemically removed, and the cycle is repeated to acquire the next base of sequence information. The lumina GA instrument operates by this method. This technique and applications thereof are discussed in detail, for example, in Ruparel et al., Proceedings of the National Academy of Sciences of the United States of America 102, 5932-5937 (2005), and Harris et al., Science 320, 106-109 (2008).

A commercially available example of reversible terminator sequencing method is Illumina's sequencing-by-synthesis and reversible terminator-based sequencing (e.g. as described in Bentley et al., Nature 6:53-59 [2009]). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about 20-40 bp e.g. 36 bp, are aligned against a repeat-masked reference genome and unique mapping of the short sequence reads to the reference genome are identified using specially developed data analysis pipeline software. Non-repeat-masked reference genomes can also be used. Whether repeat-masked or non-repeat-masked reference genomes are used, only reads that map uniquely to the reference genome are counted. After completion of the first read, the templates can be regenerated in situ to enable a second read from the opposite end of the fragments. Thus, either single-end or paired end sequencing of the DNA fragments can be used. Partial sequencing of DNA fragments present in the sample is performed, and sequence tags comprising reads of predetermined length e.g. 36 bp, are mapped to a known reference genome are counted.

In nanopore sequencing, a single stranded nucleic acid molecule is threaded through a pore, e.g., using an electrophoretic driving force, and sequence is deduced by analyzing data obtained as the single stranded nucleic acid molecule passes through the pore. The data can be ion current data, wherein each base alters the current, e.g., by partially blocking the current passing through the pore to a different, distinguishable degree.

In another illustrative, but non-limiting, embodiment, the methods described herein comprises obtaining sequence information using transmission electron microscopy (TEM). The method comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445.

In another illustrative, but non-limiting, embodiment, the methods described herein comprises obtaining sequence information using third-generation sequencing. In third-generation sequencing, a slide with an aluminum coating with many small (~50 nm) holes is used as a zero mode waveguide (see, e.g., Levene et al., Science 299, 682-686 (2003)). The aluminum surface is protected from attachment of DNA polymerase by polyphosphonate chemistry, e.g., polyvinylphosphonate chemistry (see, e.g., Korlach et al., Proceedings of the National Academy of Sciences of the United States of America 105, 1176-1181 (2008)). This results in preferential attachment of the DNA polymerase molecules to the exposed silica in the holes of the aluminum coating. This setup allows evanescent wave phenomena to be used to reduce fluorescence background, allowing the use of higher concentrations of fluorescently labeled dNTPs. The fluorophore is attached to the terminal phosphate of the dNTPs, such that fluorescence is released upon incorporation of the dNTP, but the fluorophore does not remain attached to the newly incorporated nucleotide, meaning that the complex is immediately ready for another round of incorporation. By this method, incorporation of dNTPs into an individual primer-template complexes present in the holes of the aluminum coating can be detected. See, e.g., Eid et al., Science 323, 133-138 (2009).

V. Generating a Sequence-Activity Model

As indicated above, a sequence-activity model used with the embodiments herein relates protein sequence information to protein activity. The protein sequence information used by the model may take many forms. In some embodiments, it is a complete sequence of the amino acid residues in a protein. However, in some embodiments, the complete amino acid sequence is unnecessary. For example, in some embodiments, it is sufficient to provide only those residues that are to be varied in a particular research effort. In some embodiments involving later research stages, many residues are fixed and only limited regions of sequence space remain to be explored. In some of such situations, it is convenient to provide sequence-activity models that require, as inputs, only the identification of those residues in the regions of the protein where the exploration continues. In some additional embodiments, the models do not require that the exact identities of residues at the residue positions be known. In some such embodiments, one or more physical or chemical properties that characterize the amino acid at a particular residue position is/are identified. In one illustrative example, the model requires specification of residue positions by bulk, hydrophobicity, acidity, etc. Furthermore, in some models, combinations of such properties are employed. Indeed, it is not intended that the present invention be limited to any particular approach, as the models find use in various configurations of sequence information, activity information and/or other physical properties (e.g., hydrophobicity, etc.).

Thus, the form of the sequence-activity model can vary widely, so long as it provides a vehicle for correctly approximating the relative activity of proteins based on sequence information, as desired. In some embodiments, the models generally treat activity as a dependent variable and sequence/residue values as independent variables. Examples of the mathematical/logical form of models include additive, multiplicative, linear, and non-linear mathematical expressions of various orders, neural networks, classification and regression trees/graphs, clustering approaches, recursive partitioning, support vector machines, and the like.

Some embodiments of the models include a product of a plurality of multiplicative terms. At least some of the multiplicative terms are non-interaction multiplicative terms, each of which comprises a coefficient representing a defined amino acid or nucleotide's contribution to activity of interest. The defined amino acid or nucleotide is of a specific residue type at a specific position in a protein or nucleic acid sequence. Each of the non-interactive multiplicative terms also includes a single independent variable, or dummy variable, that represents the presence or absence of the defined amino acid or nucleotide. In addition, each of the sequence-activity models in some embodiments of the invention comprises a dependent variable representing the activity of a protein variant.

In some embodiments of the invention, the sequence-activity models also include interaction terms, each of which comprises an interaction coefficient representing the contribution to activity of a defined combination of (i) a first amino acid or nucleotide at a first position in the protein sequence, and (ii) a second amino acid or nucleotide at a second position in the protein sequence.

In some embodiments of the invention, the models combine the interaction terms by multiplication or addition. In some embodiments, the models combine the interaction terms with the non-interaction multiplicative terms by multiplication or addition. In some embodiments, the models are purely multiplicative, combining the non-interaction and interaction terms into a single product. In other embodiments, the models include at least one product of multiple terms combined with one or more other terms by addition.

In some alternative embodiments of the invention, the sequence-activity models have an additive form comprising a sum of one or more non-interaction terms and at least one interaction term. The at least one interaction term is a cross-product term containing a product of one variable representing the presence of one interacting residue and another variable representing the presence of another interacting residue.

In some embodiments, models are developed from a training set of activity versus sequence information to provide the mathematical/logical relationship between activity and sequence. This relationship is typically validated prior to use for predicting the activity of new sequences or the impacts of residues on the activity of interest.

Various techniques for generating models are available and find use in the present invention. In some embodiments, the techniques involve optimization of models or minimization of model errors. Specific examples include partial least squares, ensemble regression, random forest, various other regression techniques, as well as neural network techniques, recursive partitioning, support vector machine techniques, CART (classification and regression trees), and/or the like. Generally, the technique should produce a model that can distinguish residues that have a significant impact on activity from those that do not. In some embodiments, the models also rank individual residues or residue positions based on their impact on activity. It is not intended that the present invention be limited to any specific technique for generating models, as any suitable method known in the art finds use in the present invention.

In some embodiments involving additive models, the models are generated by a regression technique that identifies covariation of independent and dependent variables in a training set. Various regression techniques are known and widely used. Examples include multiple linear regression (MLR), principal component regression (PCR) and partial least squares regression (PLS). In some embodiments, models are generated using techniques that involve multiple constituents, including but not limited to ensemble regression and random forest. These and any other suitable methods find use in the present invention. It is not intended that the present invention be limited to any particular technique.

MLR is the most basic of these techniques. It is used to simply solve a set of coefficient equations for members of a training set. Each equation relates to the activity of a training set member (i.e., dependent variables) with the presence or absence of a particular residue at a particular position (i.e., independent variables). Depending upon the number of residue options in the training set, the number of these equations can be quite large.

Like MLR, PLS and PCR generate models from equations relating sequence activity to residue values. However, these techniques do so in a different manner. They first perform a coordinate transformation to reduce the number of independent variables. They then perform the regression on the transformed variables. In MLR, there is a potentially very large number of independent variables: two or more for each residue position that varies within the training set. Given that proteins and peptides of interest are often quite large and the training set may provide many different sequences, the number of independent variables can quickly become very large. By reducing the number of variables to focus on those that provide the most variation in the data set, PLS and PCR generally require fewer samples and simplify the steps involved in generating models.

PCR is similar to PLS regression in that the actual regression is done on a relatively small number of latent variables obtained by coordinate transformation of the raw independent variables (i.e., residue values). The difference between PLS and PCR is that the latent variables in PCR are constructed by maximizing covariation between the independent variables (i.e., residue values). In PLS regression, the latent variables are constructed in such a way as to maximize the covariation between the independent variables and the dependent variables (i.e., activity values). Partial Least Squares regression is described in Hand, D. J., et al. (2001) Principles of Data Mining (Adaptive Computation and Machine Learning), Boston, Mass., MIT Press, and in Geladi, et al. (1986) "Partial Least-Squares Regression: a Tutorial," Analytica Chimica Acta, 198:1-17. Both of these references are incorporated herein by reference for all purposes.

In PCR and PLS, the direct result of the regression analysis is an expression for activity that is a function of the weighted latent variables. This expression can be transformed to an expression for activity as a function of the original independent variables by performing a coordinate transformation that converts the latent variables back to the original independent variables.

In essence, both PCR and PLS first reduce the dimensionality of the information contained in the training set and then perform a regression analysis on a transformed data set, which has been transformed to produce new independent variables, but preserves the original dependent variable values. The transformed versions of the data sets may result in only a relatively few expressions for performing the regression analysis. In protocols in which no dimension reduction has been performed, each separate residue for which there can be a variation must be considered. This can be a very large set of coefficients (e.g., $2^N$ coefficients for two-way interactions, where N is the number of residue positions that may vary in the training set). In a typical principal component analysis, only 3, 4, 5, 6 principal components are employed.

The ability of machine learning techniques to fit the training data is often referred to as the "model fit" and in regression techniques such as MLR, PCR and PLS, the model fit is typically measured by the sum squared difference between measured and predicted values. For a given training set, the optimal model fit will be achieved using MLR, with PCR and PLS often having a worse model fit (higher sum squared error between measurements and predictions). However, the chief advantage of using latent variable regression techniques such as PCR and PLS lies in the predictive ability of such models. Obtaining a model fit with very small sum squared error in no way guarantees the model will be able to accurately predicted new samples not seen in the training set—in fact, it is often the opposite case, particularly when there are many variables and only a few observations (i.e., samples). Thus latent variable regression techniques (e.g., PCR, PLS), while often having worse model fits on the training data are usually more robust and are able to predict new samples outside the training set more accurately.

Another class of tools that can be used to generate models in accordance with this disclosure is the support vector machines (SVMs). These mathematical tools take training sets of sequences that have been classified into two or more groups based on activity as inputs. Support vector machines operate by weighting different members of a training set differently depending upon how close they are to a hyperplane interface separating "active" and "inactive" members of the training set. This technique requires that the scientist first decide which training set members to place in the "active" group and which training set members to place in the "inactive" group. In some embodiments, this is accomplished by choosing an appropriate numerical value for the activity level that serves as the boundary between "active" and "inactive" members of the training set. From this classification, the support vector machine generates a vector, W, that can provide coefficient values for the individual independent variables defining the sequences of the active and inactive group members in the training set. These coefficients can be used to "rank" individual residues as described elsewhere herein. The technique is used to identify a hyperplane that maximizes the distance between the closest training set members on opposite sides of that plane. In another embodiment, support vector regression modeling is carried out. In this case, the dependent variable is a vector of continuous activity values. The support vector regression model generates a coefficient vector, W, which can be used to rank individual residues.

SVMs have been used to look at large data sets in many studies and have found wide use with DNA microarrays. Their potential strengths include the ability to finely discriminate (by weighting) the factors that separate samples from each other. To the extent that an SVM can tease out precisely which residues contribute to function, it can be a particularly useful tool for ranking residues. SVMs are described in S. Gunn (1998) "Support Vector Machines for Classification and Regressions," Technical Report, Faculty of Engineering and Applied Science, Department of Electronics and Computer Science, University of Southampton, which is incorporated herein by reference for all purposes.

In some embodiments of the invention, another class of tools that can be used to generate models is classification and regression based on an ensemble of classification trees using random inputs, an example of which is random forest. See Breiman (2001). Random Forests. Machine Learning 45 (1): 5-32. Random forests are a combination of tree predictors such that each tree depends on the values of a random vector sampled independently and with the same distribution for all trees in the forest. A random forest is a learning ensemble consisting of a bagging of un-pruned decision tree learners with a randomized selection of features at each split of the decision tree. The generalization error for forests converges to a limit as the number of trees in the forest becomes large.

Random forests may be constructed in the following manner:

1) If the number of cases in the training set is N, sample N cases at random—but with replacement, from the original data. This sample will be the training set for growing the tree.

2) If there are M input independent variables, a number m<<M is specified such that at each node in the tree, m variables are selected at random out of the M and the best split on these m is used to split the node. The value of m is held constant during the forest growing.

3) In some implementations, each tree is grown to the largest extent possible. There is no pruning.

4) A large number of trees are then generated, k=1, . . . , K (usually K>=100).

5) After a large number of trees have been generated, they all vote for the classification of variables of interest. For example, they may each contribute the final prediction of activity or the contribution of particular mutations.

6) The random forest then classifies x (e.g., a sequence of mutations or other independent variable) by taking the most popular voted class from all the tree predictors in the forest.

The forest error rate depends on the correlation between any two trees in the forest. Increasing the correlation increases the forest error rate. The forest error rate depends on the strength of each individual tree in the forest. A tree with a low error rate is a strong classifier. Increasing the strength of the individual trees decreases the forest error rate. Reducing m reduces both the correlation and the strength. Increasing it increases both. Somewhere in between is an "optimal" range of m—usually quite wide.

Random forest techniques can be used for categorical variables as well as continuous variables in regression models. In some embodiments of the invention, random forest models have predictive power comparable to SVM and neural net models, but tend to have higher computational efficiency because, among other reasons, cross validation is built into the modeling process and a separate process for cross validation is not necessary.

A. Multiplicative Models

Some embodiments of the present invention provide methods for building sequence-activity models that include a product of a plurality of multiplicative terms and using the models to guide directed evolution. In some embodiments, a sequence-activity model predicts a protein variant's activity as a function of the presence or absence of two or more subunits of a sequence. In some embodiments, the subunits are amino acids constituting the protein variant. In some embodiments, the subunits are nucleic acids or codons that encode the protein variants.

In some embodiments, at least some of the multiplicative terms of the model are non-interaction multiplicative terms, each of which comprises a coefficient representing a defined amino acid or nucleotide's contribution to activity of interest. The defined amino acid or nucleotide is of a specific residue type at a specific position in a protein or nucleic acid sequence. Each of the non-interactive multiplicative terms also includes a single independent variable, or dummy variable, that represents the presence or absence of the defined amino acid or nucleotide, of a specific type at a specific sequence location. In various embodiments, the dummy variable may be implemented as bit values, such as 1 for presence and 1/coefficient for absence of the defined residue. In some embodiments, codons instead of amino acids or nucleic acids are modeled.

In some embodiments of the invention, the sequence-activity models also include interaction terms, each of which comprises an interaction coefficient representing the contribution to activity of a defined combination of (i) a first amino acid or nucleotide at a first position in the protein sequence, and (ii) a second amino acid or nucleotide at a second position in the protein sequence.

As explained above, the pool of interaction terms usually are large. Including a large number of interaction terms negatively affect efficiency of directed evolution. Additional terms also tend to cause over fitting of data, therefore reducing predictive power of the models. Multiplicative models may be able to reduce the number of interaction terms and improved predictive power of the model, because multiple non-interaction terms of the model form a product, allowing independent variables of multiple non-interaction terms to contribute to the dependent variable in a multiplicative manner. Without being bound to any of the theories postulated herein, multiplicative models may improve models' predictive power and/or the efficiency of directed evolution.

Codon degeneracy exists when two or more codons encode the same amino acid. In some embodiments, codon degeneracy may optionally be factored out by representing the two or more degenerate codons using the same independent variable. However, codon degeneracy may also be retained in the model in some embodiments. For instance, a model may relate two different nucleic acids of synonymous mutations to the same protein activity. The reasons that a multiplicative model may adequately capture the relationship between activity and protein sequence information may be demonstrated by using the Arrhenius Equations to describe protein activity as a function of the various mutations in a variant protein. The original Arrhenius Equation $$k = Ae^{-\frac{\Delta G}{RT}}$$

describes chemical reaction rate constant k as a function of activation energy $\Delta G$ and reaction temperature T (in Kelvin), wherein A is the pre-exponential factor (an empirical constant) and R is the Universal gas constant of 8.314 J/mol·K. The Arrhenius Equation can be re-written as:

$$\ln(k) = -\frac{\Delta G}{RT} + \ln(A)$$

showing that reaction rate constant positively correlates with temperature T and negatively correlates with activation energy. In other words, higher reaction temperature leads to faster reaction, and higher activation energy leads to slower reaction.

It is conceptually sensible to parallel the reaction rate of a chemical reaction to a protein's activity, and the activation energy to a mutation's contribution to the protein's activity. Drawing on the parallelism, the Arrhenius Equation can be used to describe protein activity k as a function of mutations' effect $\Delta G$. If the back bone residue of a protein has an effect of $\Delta G_0$, mutation 1 has an effect of $\Delta G_1$, and mutation 2 has an effect of $\Delta G_2$, the combined effect of mutation 1 and 2 can be expressed as:

$$k = Ae^{-\frac{(\Delta G_0 + \Delta G_1 + \Delta G_2)}{RT}} = A\left(e^{-\frac{\Delta G_0}{RT}} \times e^{-\frac{\Delta G_1}{RT}} \times e^{-\frac{\Delta G_2}{RT}}\right)$$

As seen in this equation, the effects of the two mutations can be combined into a product in a multiplicative form. In some embodiments of the invention, multiplicative models can be represented as a product of various terms. Each term represents the contribution to activity of a particular combination of a position in the sequence and a particular residue or nucleotide/codon at that position. Each of these terms includes a coefficient and an independent variable. The independent variable may take one of two values: one value when the mutation question is present and a different value when the mutation in question is absent.

In some embodiments, each term in the sequence activity model may be a simple product of its coefficient and the associated independent variable. In some embodiments of the invention, when the nucleotide or residue associated with the term is present, the value of the independent variable is set to 1. When the independent variable is not present, the value of the variable is one over the coefficient value for that term, or $1/C_n$. For interaction terms, a coefficient is provided for the contribution to activity of the interaction. An associated coefficient has a value of 1 when all interacting members (m and n) are present and a value of $1/C_{m,n}$ when they are not present.

In another form of the model, in each term the independent variable is given by a value of one when the residue or nucleotide in question is present at the position and zero when it is not present at the position. In this form of the model, the term is given by the value of one plus the coefficient times the independent variable: $(1+C_n x_n)$. Interaction terms are treated similarly to the first case: $(1+C_{m,n}, x_m x_n)$. In one embodiment, a model can take on this form:

$$y = (1+C_1 x_1) \times (1+C_2 x_2) \times (1+C_3 x_3) \times \ldots \times (1+C_n x_n)$$

Interaction terms may or may not be present in the model. It is possible that by its very nature, the product accounts for the interactions between interacting residues. In the event that the multiplicative model does not inherently account for the full contribution of such interactions, interaction terms may be included as terms in the multiplicative model. In such case, one or more interaction terms can be incorporated by including coefficients representing the presence of two or more mutations, and the dummy variables representing the two mutations:

$$(1+C_{1,2} x_1 x_2) \times (1+C_{2,3} x_2 x_3) \times \ldots \times (1+C_{m,n} x_m x_n)$$

In some embodiments, the interaction terms are multiplied with the non-interaction terms. In other embodiments, the interaction terms may be combined by summation with the non-interaction terms. In the above embodiments, the interaction terms are combined among themselves by multiplication. In alternative embodiments, the interaction terms can be combined among themselves by addition.

Table I provides an example that includes a protein backbone and variants having 4 positions of interests: 10, 166, 175, and 340. The backbone residues are Ala at 10, Phe at 166, Gly at 175, and Phe at 340. The activities of the proteins are measured as y for the backbone and $y_n$ for the variants.

TABLE I

Illustrative Sequence Activity Data for Interaction Models*

| | Positions | | | | |
|---|---|---|---|---|---|
| | 10 | 166 | 175 | 340 | y(activity) |
| Backbone | Ala | Phe | Gly | Phe | y |
| Variant1 | Ala | Ser | Gly | Phe | $y_1$ |
| Variant2 | Asp | Phe | Val | Ala | $y_2$ |
| Variant3 | Lys | Leu | Gly | Ala | $y_3$ |
| Variant4 | Asp | Ile | Val | Phe | $y_4$ |
| Variant5 | Ala | Ile | Val | Ala | $y_5$ |

*All possible amino acids at each varying position could be considered. In this example, only mutations within the variants (relative to backbone) are considered.

Applying a multiplicative model in the following form to the example, $$y_n = (1+C_{10Asp} X_{10Asp}) * (1+C_{10Lys} X_{10Lys}) *$$
$$(1+C_{166Ser} X_{166Ser}) * (1+C_{166Leu} X_{166Leu}) *$$
$$(1+C_{166Ile} X_{166Ile}) * (1+C_{175Val} X_{175Val}) * (1+C_{340Ala} X_{340Ala})$$

one can obtain the predicted activity of variant 2 by the model as following:

$$y_2 = (1+C_{10Asp} * 1) * (1+C_{10Lys} * 0) * (1+C_{166Ser} * 0) * (1+C_{16Leu} * 0) *$$
$$(1+C_{166Ile} * 0) * (1+C_{175Val} * 1) * (1+C_{340Ala} * 1) =$$
$$(1+C_{10Asp} * 1) * (1+C_{175Val} * 1) * (1+C_{340Ala} * 1)$$

Although the model equation could contain all amino acids at variable position, such that:

$$y_n = (1+C_{10Ala} X_{10Ala}) * (1+C_{10Asp} X_{10Asp}) *$$
$$(1+C_{10Lys} X_{10Lys}) * (1+C_{166Ser} X_{166Ser}) * (1+C_{166Phe} X_{166Phe}) *$$
$$(1+C_{166Leu} X_{166Leu}) * (1+C_{166Ile} X_{166Ile}) * (1+C_{175Gly} X_{175Gly}) *$$
$$(1+C_{175Val} X_{175Val}) * (1+C_{340Phe} X_{340Phe}) * (1+C_{340Ala} X_{340Ala})$$

Terms in the backbones are often dropped from the equation. This approach is acceptable because often the methods fit the model using fold improvement of variants (FIOP), thus the backbone amino acid coefficients are 0 (such that y of backbone=1).

In some alternative embodiments, another approach is to use a lookup table in which the coefficient values are provided for each and every combination of a position and associated mutation. To predict activity for a variant sequence (collection of mutations), the algorithm simply identifies those mutations that are present in the variant and picks the associated coefficient values for those mutations from a lookup table. The selected coefficients are then multiplied by one another to produce the predicted activity value, which is the dependent variable.

Figure 3A:
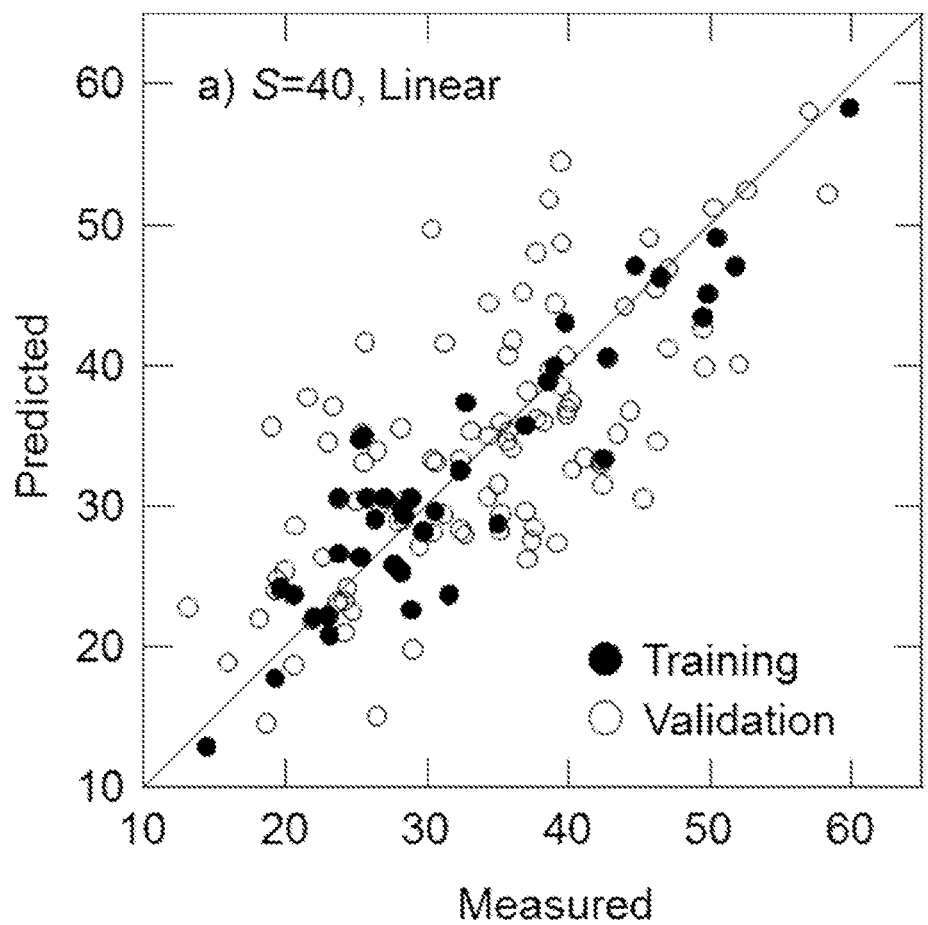
FIGS. 3A-H are graphs showing examples in which the predictive capabilities of linear vs. non-linear additive models are compared.
Figure 3B:
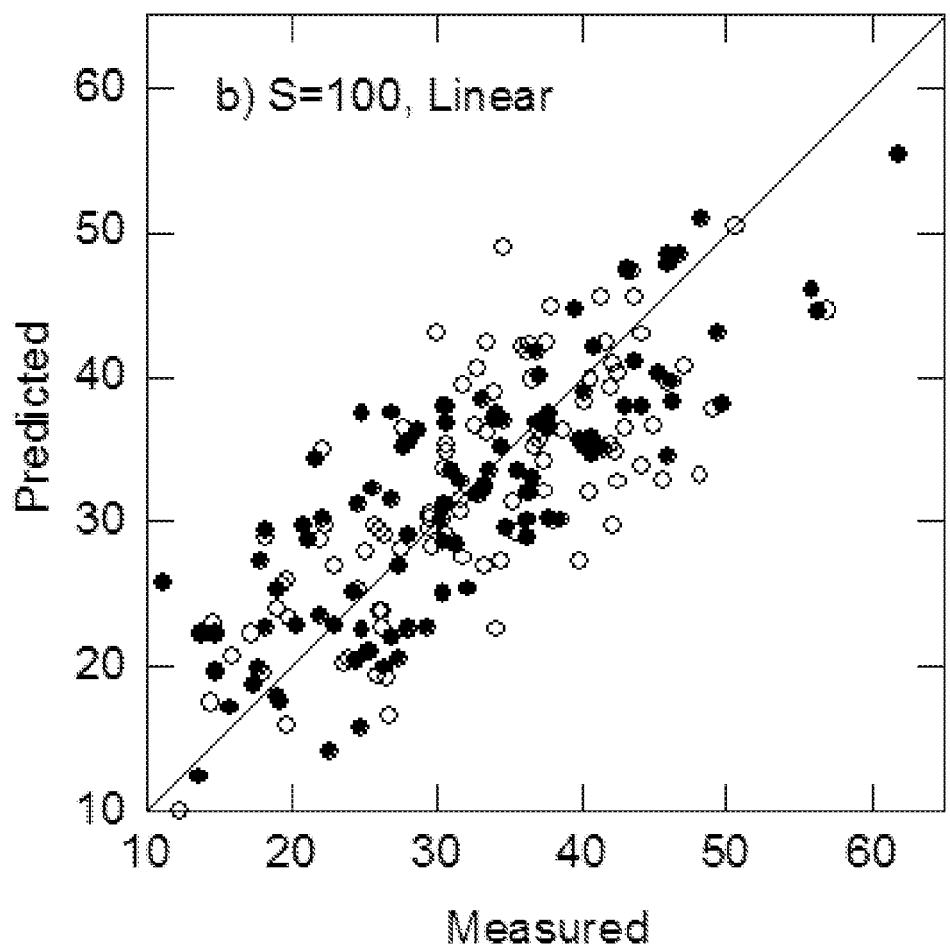
Figure 3C:
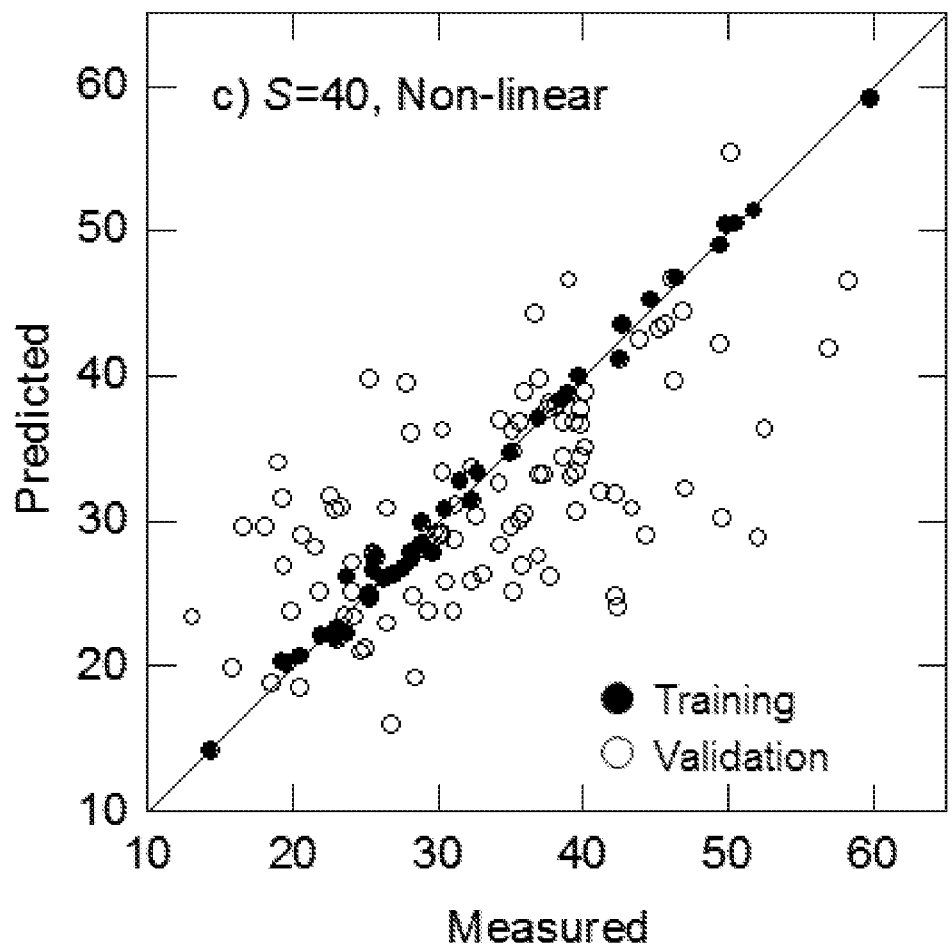
Figure 3D:
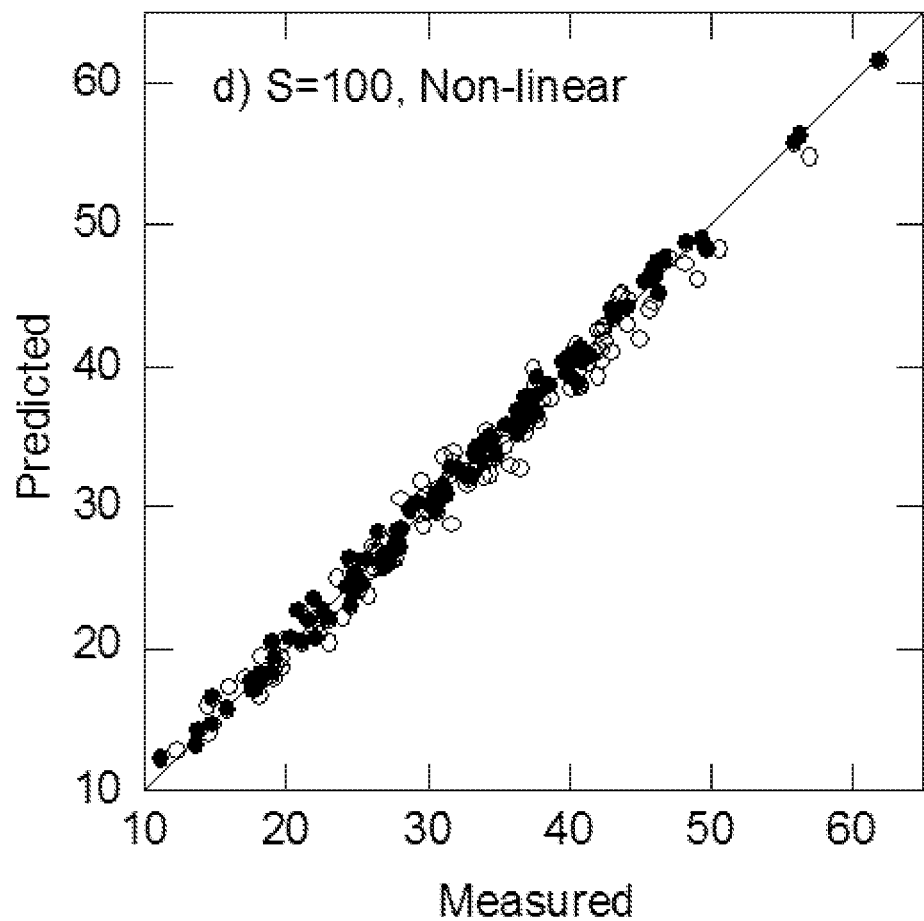
Figure 3E:
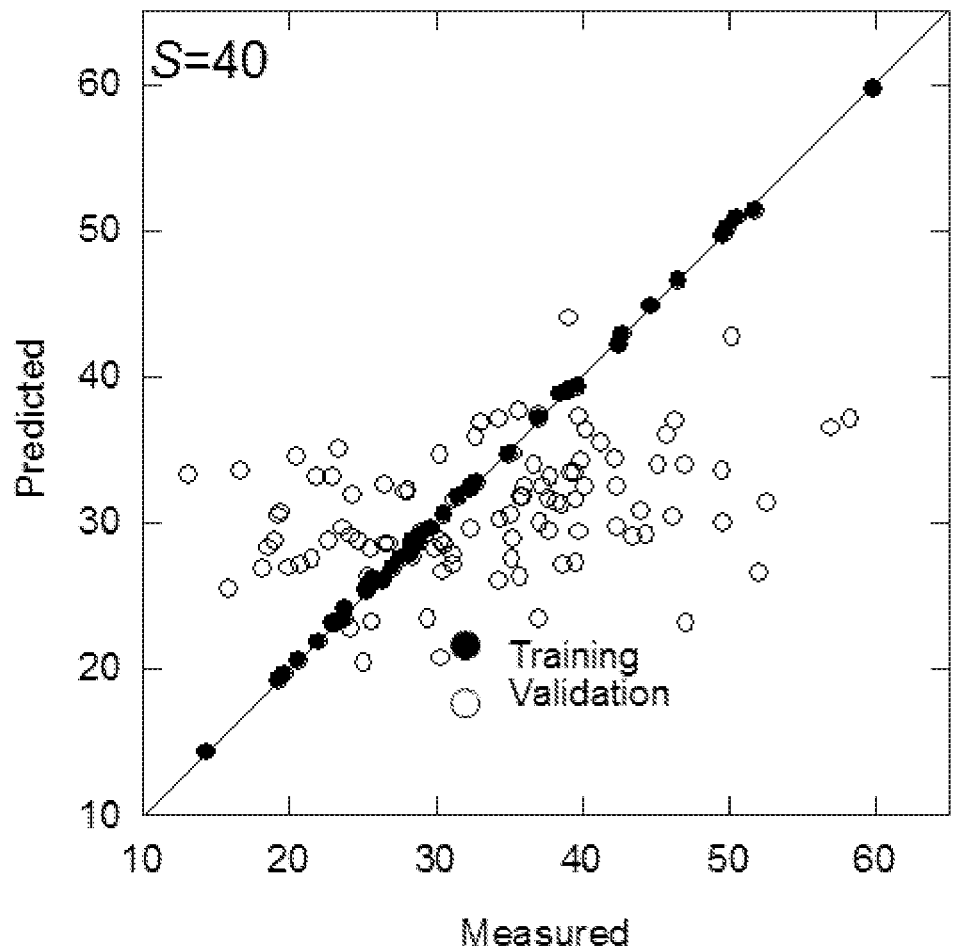
Figure 3F:
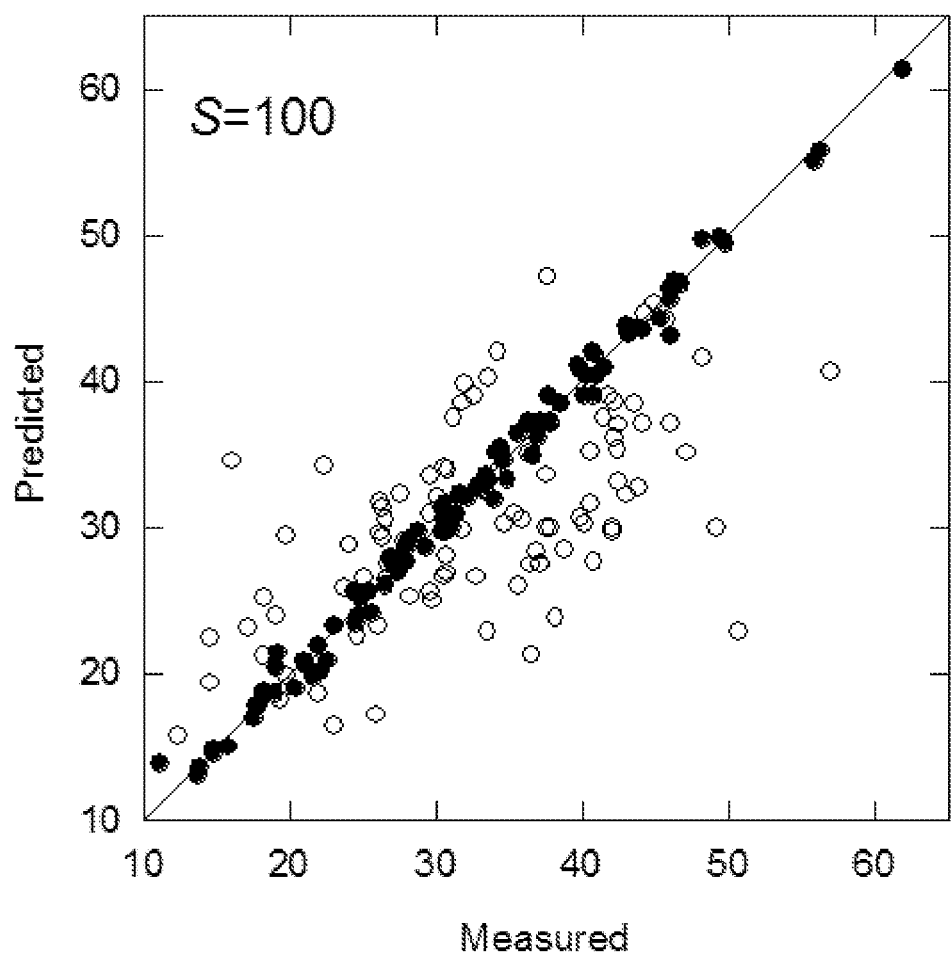
Figure 3G:
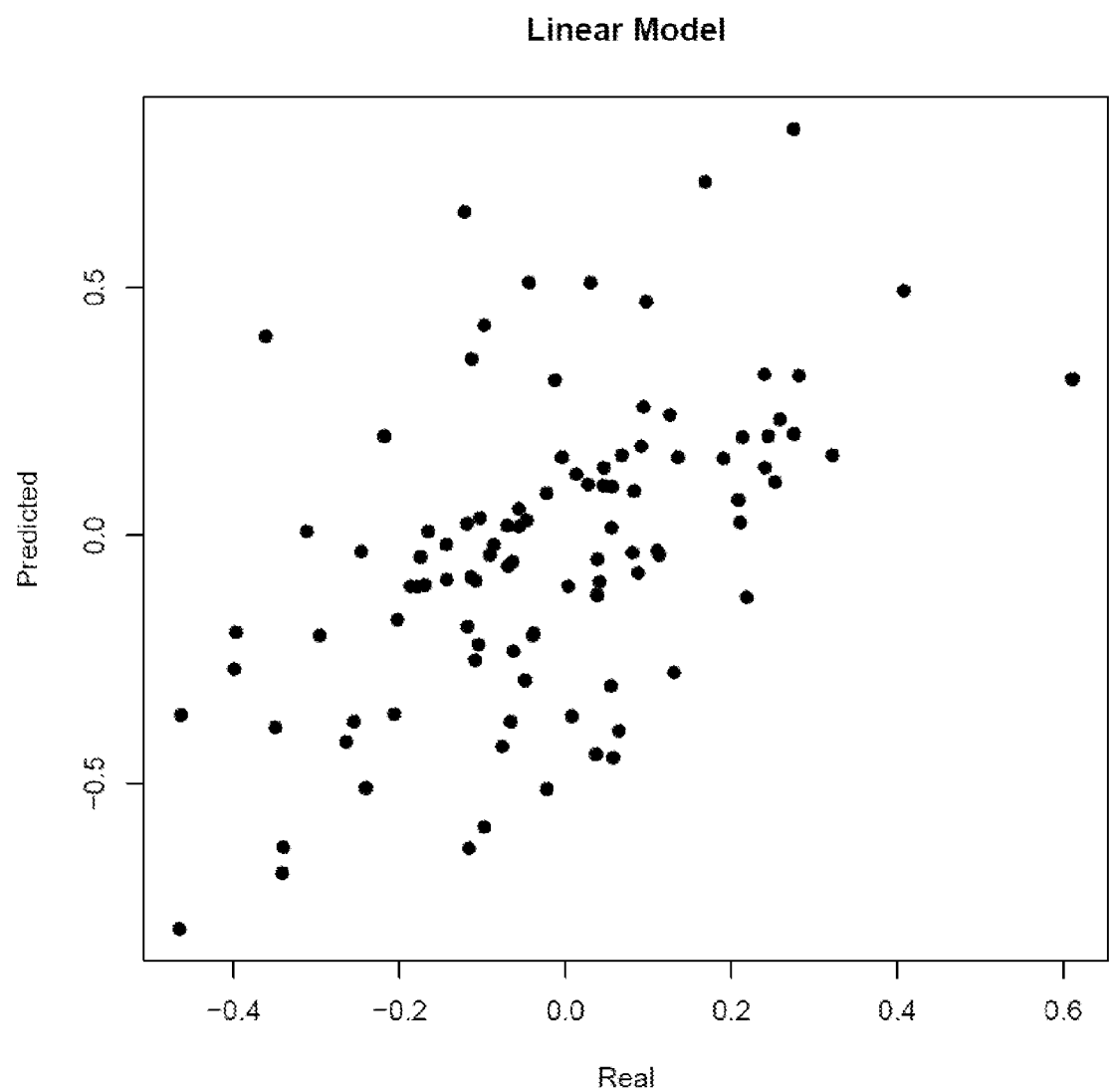
Figure 3H:
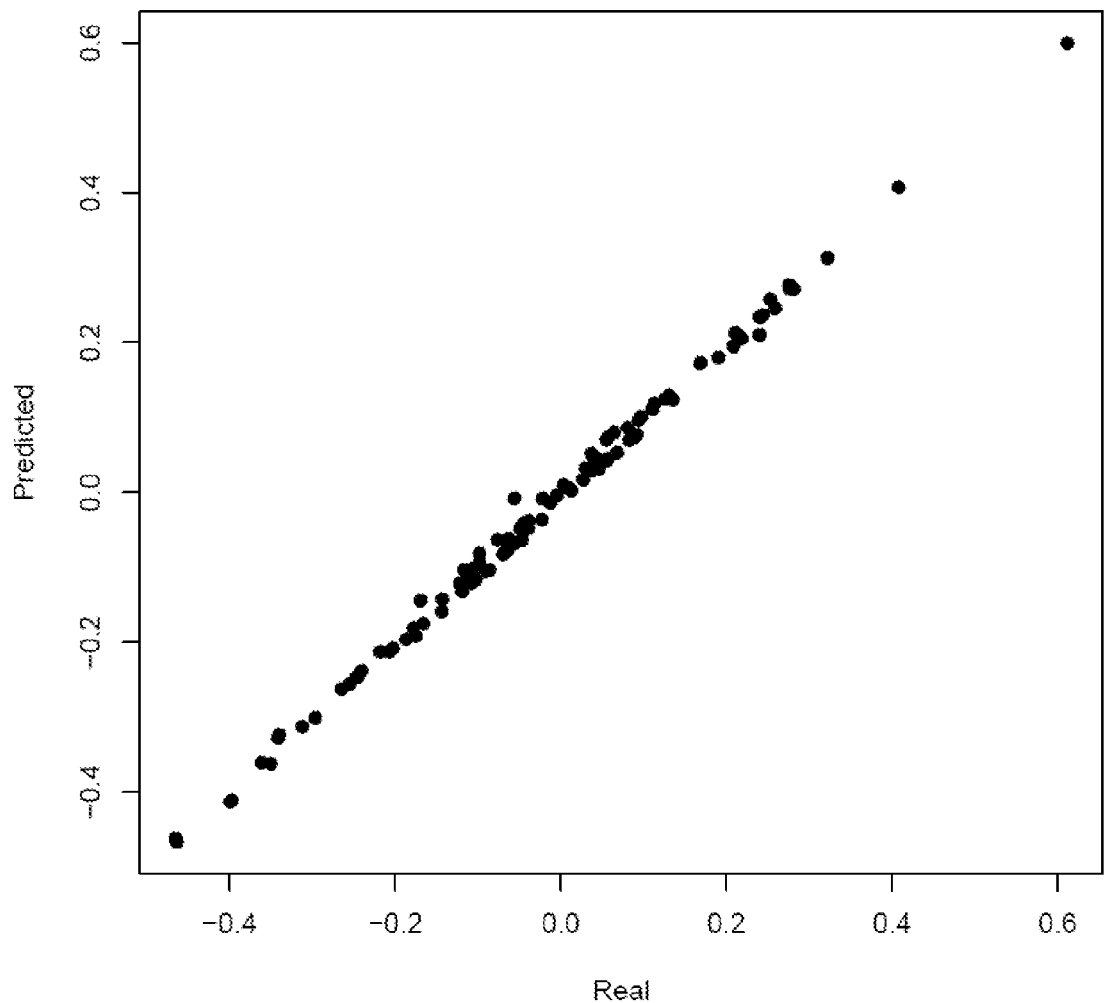
Figure 3I:
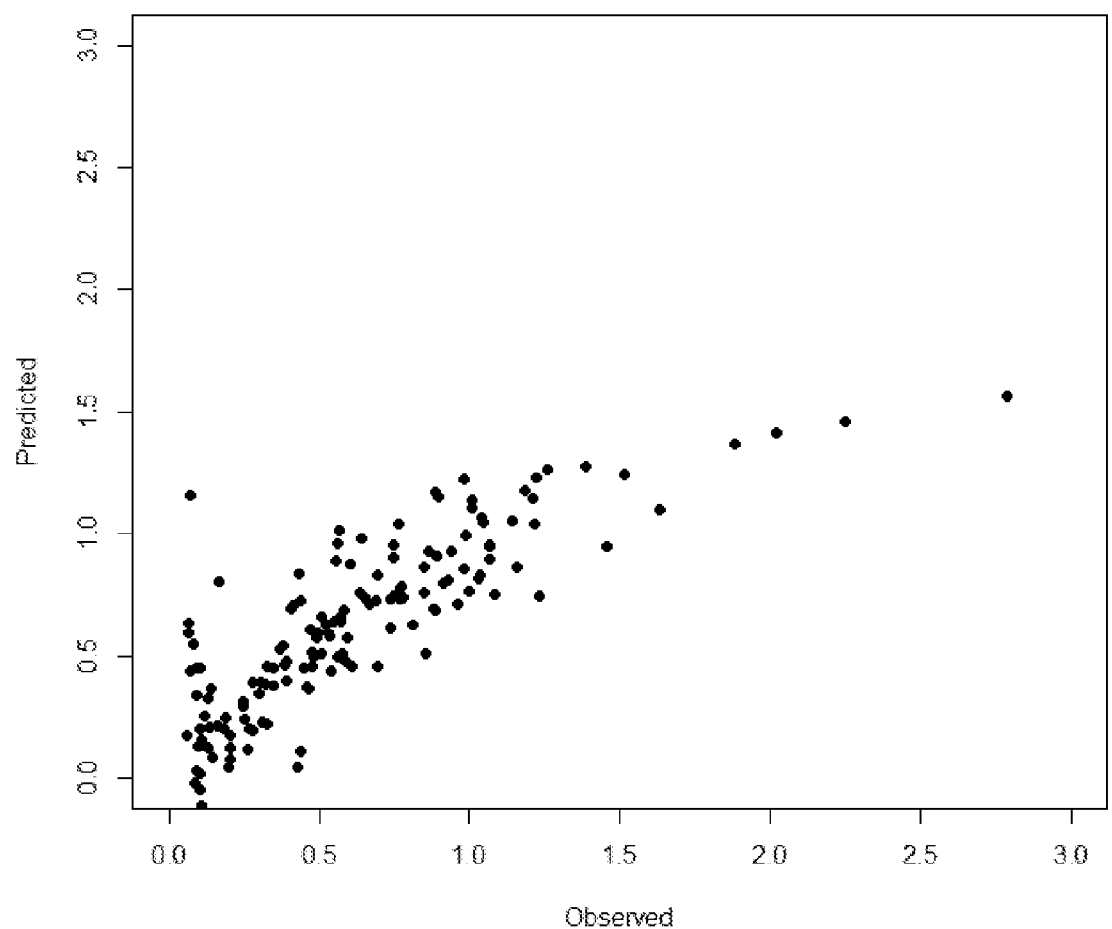
FIGS. 3I-J are graphs showing examples in which the predictive capabilities of certain multiplicative and additive models are compared.
Figure 3J:
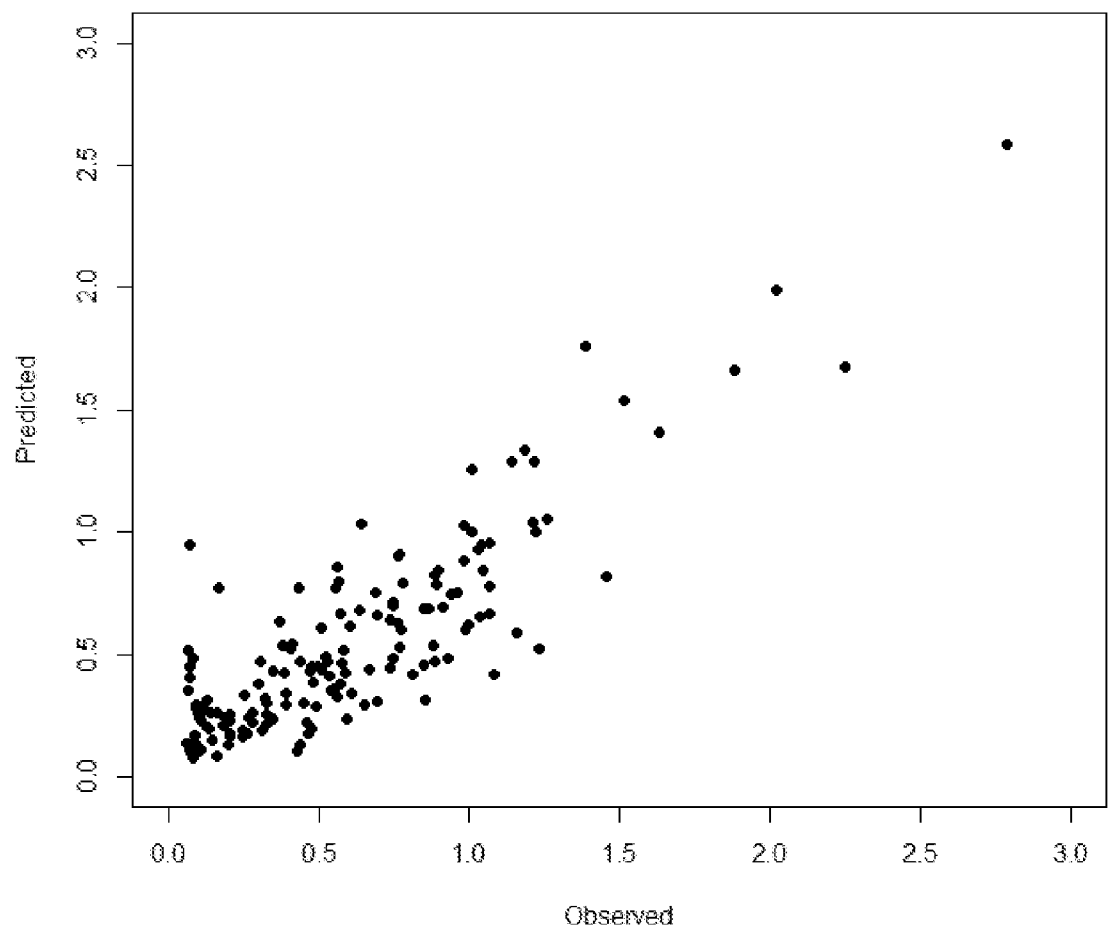

FIG. 3I-J show an example where a multiplicative model fits observed data better than an additive model, providing higher predictive power under certain circumstances. The observed data comprise protein variants harboring mutations that tend to cause severe deleterious effects on protein activity. FIG. 3I plots the predicted activity values of a non-interaction additive model against the observed activity values of the training set of protein variants. It is apparent that the additive model's predictions suffer significant under-estimation for observations that have high activity values. In contrast, the predicted activity values of a multiplicative model better match the observed activity values as shown in FIG. 3J, having significantly smaller errors than the additive model.

B. Linear Additive Models

In some embodiments, a linear model is used as a "base" model in a step-wise process for generating a non-linear model. In general, a linear regression model of activity versus sequence has the following form:

$$y = c_0 + \sum_{i=1}^{N} \sum_{j=1}^{M} c_{ij} x_{ij} \qquad (1)$$

In this linear expression, y is predicted response, while $c_{ij}$ and $x_{ij}$ are the regression coefficient and bit value or dummy variable used to represent residue choice, respectively at position i in the sequence. There are N residue positions in the sequences of the protein variant library and each of these may be occupied by one or more residues. At any given position, there may be j=1 through M separate residue types. This model assumes a linear (additive) relationship between the residues at every position. An expanded version of equation 1 follows:

$$y = c_0 + c_{11} x_{11} + c_{12} x_{12} + \ldots c_{1M} x_{1M} + c_{21} x_{21} + c_{22} x_{22} + \ldots c_{2M} x_{2M} + \ldots + c_{NM} x_{NM}$$

As indicated, data in the form of activity and sequence information is derived from the initial protein variant library and used to determine the regression coefficients of the model. The dummy variables are first identified from an alignment of the protein variant sequences. Amino acid residue positions are identified from among the protein variant sequences in which the amino acid residues in those positions differ between sequences. Amino acid residue information in some or all of these variable residue positions may be incorporated in the sequence-activity model.

Table II contains sequence information in the form of variable residue positions and residue types for 10 illustrative variant proteins, along with activity values corresponding to each variant protein. These are representative members of a larger set that is required to generate enough equations to solve for all of the coefficients. Thus, for example, for the illustrative protein variant sequences in Table II, positions 10, 166, 175, and 340 are variable residue positions and all other positions, i.e., those not indicated in the Table, contain residues that are identical between Variants 1-10.

In this example, the 10 variants may or may not include the wild-type backbone sequence. In some embodiments, a model developed to account for data of all variants including the wild-type backbone sequence may introduce a problem of perfect multi-collinearity, or a dummy variable trap. This problem may be addressed by various techniques. Some embodiments may exclude the wild-type backbone data from developing the model. Some embodiments may drop out those coefficients representing the wild-type backbone. Some embodiments may use techniques such as PLS regression to address multi-collinearity.

TABLE II

Illustrative Sequence and Activity Data

| Variable Residue Position | 10 | 166 | 175 | 340 | y (activity) |
|---|---|---|---|---|---|
| Variant 1 | Ala | Ser | Gly | Phe | $y_1$ |
| Variant 2 | Asp | Phe | Val | Ala | $y_2$ |
| Variant 3 | Lys | Leu | Gly | Ala | $y_3$ |
| Variant 4 | Asp | Ile | Val | Phe | $y_4$ |
| Variant 5 | Ala | Ile | Val | Ala | $y_5$ |
| Variant 6 | Asp | Ser | Gly | Phe | $y_6$ |
| Variant 7 | Lys | Phe | Gly | Phe | $y_7$ |
| Variant 8 | Ala | Phe | Val | Ala | $y_8$ |
| Variant 9 | Lys | Ser | Gly | Phe | $y_9$ |
| Variant 10 | Asp | Leu | Val | Ala | $y_{10}$ |

Thus, based on equation 1, a regression model can be derived from the systematically varied library in Table II, i.e.:

$$y = c_0 + c_{10Ala} x_{10Ala} + c_{10Asp} x_{10Asp} + c_{10Lys} x_{10Lys} + c_{166Ser} x_{166Ser} + c_{166Phe} x_{166Phe} + c_{166Leu} x_{166Leu} + c_{166Ile} x_{166Ile} + c_{175Gly} x_{175Gly} + c_{175Val} x_{175Val} + c_{340Phe} x_{340Phe} + c_{340Ala} x_{340Ala} \quad \text{(Eq. 2)}$$

The bit values (x dummy variables) can be represented as either 1 or 0 reflecting the presence or absence of the designated amino acid residue or alternatively, 1 or −1, or some other surrogate representation. For example, using the 1 or 0 designation, $x_{10Ala}$ would be "1" for Variant 1 and "0" for Variant 2. Using the 1 or −1 designation, $x_{10Ala}$ would be "1" for Variant 1 and "−1" for Variant 2. The regression coefficients can thus be derived from regression equations based on the sequence activity information for all variants in library. Examples of such equations for Variants 1-10 (using the 1 or 0 designation for x) follow:

$$y_1 = c_0 + c_{10Ala}(1) + c_{10Asp}(0) + c_{10Lys}(0) + c_{166Ser}(1) + c_{166Phe}(0) + c_{166Leu}(0) + c_{166Ile}(0) + c_{175Gly}(1) + c_{175Val}(0) + c_{340Phe}(1) + c_{340Ala}(0)$$

$$y_2 = c_0 + c_{10Ala}(0) + c_{10Asp}(1) + c_{10Lys}(0) + c_{166Ser}(0) + c_{166Phe}(1) + c_{166Leu}(0) + c_{166Ile}(0) + c_{175Gly}(0) + c_{175Val}(1) + c_{340Phe}(0) + c_{340Ala}(1)$$

$$y_3 = c_0 + c_{10Ala}(0) + c_{10Asp}(0) + c_{10Lys}(1) + c_{166Ser}(0) + c_{166Phe}(0) + c_{166Leu}(1) + c_{166Ile}(0) + c_{175Gly}(1) + c_{175Val}(0) + c_{340Phe}(0) + c_{340Ala}(1)$$

$$y_4 = c_0 + c_{10Ala}(0) + c_{10Asp}(1) + c_{10Lys}(0) + c_{166Ser}(0) + c_{166Phe}(0) + c_{166Leu}(0) + c_{166Ile}(1) + c_{175Gly}(0) + c_{175Val}(1) + c_{340Phe}(1) + c_{340Ala}(0)$$

$$y_5 = c_0 + c_{10Ala}(1) + c_{10Asp}(0) + c_{10Lys}(0) + c_{166Ser}(0) + c_{166Phe}(0) + c_{166Leu}(0) + c_{166Ile}(1) + c_{175Gly}(0) + c_{175Val}(1) + c_{340Phe}(0) + c_{340Ala}(0)$$

$$y_6 = c_0 + c_{10Ala}(0) + c_{10Asp}(1) + c_{10Lys}(0) + c_{166Ser}(1) + c_{166Phe}(0) + c_{166Leu}(0) + c_{166Ile}(0) + c_{175Gly}(1) + c_{175Val}(0) + c_{340Phe}(1) + c_{340Ala}(0)$$

$$y_7 = c_0 + c_{10Ala}(1) + c_{10Asp}(0) + c_{10Lys}(1) + c_{166Ser}(0) + c_{166Phe}(1) + c_{166Leu}(0) + c_{166Ile}(0) + c_{175Gly}(1) + c_{175Val}(0) + c_{340Phe}(1) + c_{340Ala}(0)$$

$$y_8 = c_0 + c_{10Ala}(1) + c_{10Asp}(0) + c_{10Lys}(0) + c_{166Ser}(0) + c_{166Phe}(1) + c_{166Leu}(0) + c_{166Ile}(0) + c_{175Gly}(0) + c_{175Val}(1) + c_{340Phe}(0) + c_{340Ala}(1)$$

$$y_9 = c_0 + c_{10Ala}(0) + c_{10Asp}(0) + c_{10Lys}(1) + c_{166Ser}(1) + c_{166Phe}(0) + c_{166Leu}(0) + c_{166Ile}(0) + c_{175Gly}(1) + c_{175Val}(0) + c_{340Phe}(1) + c_{340Ala}(0)$$

$$y_{10} = c_0 + c_{10Ala}(0) + c_{10Asp}(1) + c_{10Lys}(0) + c_{166Ser}(0) + c_{166Phe}(0) + c_{166Leu}(1) + c_{166Ile}(0) + c_{175Gly}(0) + c_{175Val}(1) + c_{340Phe}(0) + c_{340Ala}(1)$$

The complete set of equations can be readily solved using any suitable regression technique (e.g., PCR, PLS, or MLR) to determine the value for regression coefficients corresponding to each residue and position of interest. In this example, the relative magnitude of the regression coefficient correlates to the relative magnitude of contribution of that particular residue at the particular position to activity. The regression coefficients may then be ranked or otherwise categorized to determine which residues are more likely to favorably contribute to the desired activity. Table III provides illustrative regression coefficient values corresponding to the systematically varied library exemplified in Table II:

TABLE III

Illustrative Rank Ordering of Regression Coefficients

| REGRESSION COEFFICIENT | VALUE |
|---|---|
| $c_{166Ile}$ | 62.15 |
| $c_{175Gly}$ | 61.89 |
| $c_{10Asp}$ | 60.23 |
| $c_{340\,Ala}$ | 57.45 |
| $c_{10\,Ala}$ | 50.12 |
| $c_{166\,Phe}$ | 49.65 |
| $c_{166Leu}$ | 49.42 |
| $c_{340\,Phe}$ | 47.16 |
| $c_{166Ser}$ | 45.34 |
| $c_{175\,Val}$ | 43.65 |
| $c_{10\,Lys}$ | 40.15 |

The rank ordered list of regression coefficients can be used to construct a new library of protein variants that is optimized with respect to a desired activity (i.e., improved fitness). This can be done in various ways. In one embodiment, it is accomplished by retaining the amino acid residues having coefficients with the highest observed values. These are the residues indicated by the regression model to contribute the most to desired activity. If negative descriptors are employed to identify residues (e.g., 1 for leucine and −1 for glycine), it becomes necessary to rank residue positions based on the absolute value of the coefficient. Note that in such situations, there is typically only a single coefficient for each residue. The absolute value of the coefficient magnitude gives the ranking of the corresponding residue position. Then, it becomes necessary to consider the signs of the individual residues to determine whether each of them is detrimental or beneficial in terms of the desired activity.

C. Non-Linear Additive Models

Non-linear modeling is employed to account for residue-residue interactions that contribute to activity in proteins. An N-K landscape describes this problem. The parameter N refers to the number of variable residues in a collection of related polypeptides sequences. The parameter K represents the interaction between individual residues within anyone of these polypeptides. Interaction is usually a result of close physical proximity between various residues whether in the primary, secondary, or tertiary structure of the polypeptide. The interaction may be due to direct interactions, indirect interactions, physicochemical interactions, interactions due to folding intermediates, translational effects, and the like. See Kauffman, S. and Levin, S. (1987), "Towards a general theory of adaptive walks on rugged landscapes", Journal of Theoretical Biology 128 (1) 11-45.

The parameter K is defined such that for value K=1, each variable residue (e.g., there are 20 of them) interacts with exactly one other residue in its sequence. In the case where all residues are physically and chemically separate from the effects of all other residues, the value of K is zero. Obviously, depending upon the structure of the polypeptide, K can have a wide range of different values. With a rigorously solved structure of the polypeptide in question, a value for K may be estimated. Often, however, this is not the case.

A purely linear, additive model of polypeptide activity (as described above) can be improved by including one or more non-linear interaction terms representing specific interactions between 2 or more residues. In the context of the model form presented above, these terms are depicted as "cross-products" containing two or more dummy variables representing the two or more particular residues (each associated with a particular position in the sequence) that interact to have a significant positive or negative impact on activity. For example, a cross-product term may have the form $c_{ab}x_ax_b$, where $x_a$ is a dummy variable representing the presence of a particular residue at a particular position on the sequence and the variable $x_b$ represents the presence of a particular residue at a different position (that interacts with the first position) in the polypeptide sequence. A detailed example form of the model is shown below.

The presence of all residues represented in the cross-product term (i.e., each of two or more specific types of residue at specifically identified positions) impacts the overall activity of the polypeptide. The impact can be manifested in many ways. For example, each of the individual interacting residues when present alone in a polypeptide may have a negative impact on activity, but when they are present in the polypeptide, the overall effect is positive. The opposite may be true in other cases. In addition, there may be a synergistic effect produced, in which each of the individual residues alone has a relatively limited impact on activity, but when all of them are present, the effect on activity is greater than the cumulative effects of all the individual residues.

In some embodiments, non-linear models include a cross-product term for every possible combination of interacting variable residues in the sequence. However, this does not represent physical reality, as only a subset of the variable residues actually interact with one another. In addition, it would result in "overfitting" to produce a model that provides spurious results that are manifestations of the particular polypeptides used to create the model and do not represent real interactions within the polypeptide. The correct number of cross-product terms for a model that represents physical reality, and avoids overfitting, is dictated by the value of K. For example, if K=1, the number of cross-product interaction terms equals N.

In constructing a non-linear model, in some embodiments, it is important to identify those cross-product interaction terms representing true structural interactions that have a significant impact on activity. This can be accomplished in various ways, including but not limited to forward addition in which candidate cross-product terms are added to the initial linear only model one at a time until the addition of terms is no longer statistically significant, and reverse subtraction, in which all possible cross product terms are provided in an initial model and removed one at a time. The illustrative examples presented below involve the use of stepwise addition and subtraction techniques to identify the useful non-linear terms.

In some embodiments, the approach to generating a non-linear model containing such interaction terms is the same as the approach described above for generating a linear model. In other words, a training set is employed to "fit" the data to a model. However, one or more non-linear terms, preferably the cross-product terms discussed above, are added to the model. Further, the resulting non-linear model, like the linear models described above, can be employed to rank the importance of various residues on the overall activity of a polypeptide. Various techniques can be used to identify the best combination of variable residues as predicted by the non-linear equation. Approaches to ranking the residues are described below. In some embodiments, very large numbers of possible cross-product terms for variable residues are used, even when limited to interactions caused by only two residues. As more interactions occur, the number of potential interactions to consider for a non-linear model grows in an exponential manner. If the model includes the possibility of interactions that include three or more residues, the number of potential terms grows even more rapidly.

In a simple illustrative example, in which there are 20 variable residues and K=1 (this assumes that each variable residue interacts with one other variable residue), there should be 20 interaction terms (cross-products) in the model. If there are any fewer interaction terms, the model will not fully describe the interactions (although some of the interactions may not have a significant impact on activity). In contrast, if there are any more interaction terms the model may overfit the data set. In this example, there are $N*(N-1)/2$ or 190 possible pairs of interactions. Finding the combination of 20 unique pairs that describe the 20 interactions in the sequence is a significant computational problem, as there are approximately $5.48 \times 10^{26}$ possible combinations.

Numerous techniques can be employed to identify the relevant cross-product terms. Depending upon the size of the problem and the computational power available, it is possible to explore all possible combinations and thereby identify the one model that best fits the data. However, often the problem is computationally demanding. Thus, in some embodiments, an efficient search algorithm or an approximation it utilized. As indicated herein, one suitable search technique is a stepwise technique. However, it is not intended that the present invention be limited to any particular method for identification of the relevant cross-product terms.

An illustrative example is presented below in Table IV to show the value of incorporating non-linear cross-product terms in a model predicting activity from sequence information. This example is a non-linear model in which it is assumed there are only two residue options at each variable position in the sequence. In this example, the protein sequence is cast into a coded sequence by using dummy variables that correspond to choice A or choice B, using +1 and −1 respectively. The model is immune to the arbitrary choice of which numerical value is used to assign each residue choice. The variable positions shown in the first row of Table IV do not indicate the actual sequence positions of a protein sequence. Instead, they are arbitrary labels representing any 10 hypothetical positions in a protein sequence that can be varied with one of two options shown in the second and third rows of Table IV for Residue Choice A and Residual Choice B.

TABLE IV

Example of coding residues at positions each having two options

| Variable Position Label | 1 | 2 | 3 | 4 | 5 | 6 | 7 | 8 | 9 | 10 |
|---|---|---|---|---|---|---|---|---|---|---|
| Residue Choice A | I | L | L | M | G | W | K | C | S | F |
| Residue Choice B | V | A | I | P | H | N | R | T | A | Y |
| Protein Residue Choice | V | A | L | P | G | W | K | T | S | F |
| Model Code Value | −1 | −1 | 1 | −1 | 1 | 1 | 1 | −1 | 1 | 1 |

With this coding scheme, the linear model used to associate protein sequences with activity can be written as follows:

$$y = c_1 x_1 + c_2 x_2 + c_2 x_2 \ldots + c_n x_n + \ldots + c_N x_N + c_0 \quad \text{(Eq. 3)}$$

where y is the response (activity), $c_n$ the regression coefficient for the residue choice at position n, x the dummy variable coding for the residue choice (+1/−1) at position n, and $c_0$ the mean value of the response. This form of the model assumes there are no interactions between the variable residues (i.e., each residue choice contributes independently to the overall fitness of the protein).

The non-linear model includes a certain number of (as yet undetermined) cross-product terms to account for interactions between residues:

$$y = c_1 x_1 + c_2 x_2 + c_3 x_3 + \ldots + c_n x_n + c_{1,2} x_1 x_2 + c_{1,3} x_1 x_3 + c_{2,3} x_2 x_3 + \ldots + c_0 \quad \text{(Eq. 4)}$$

where the variables are the same as those in Eq. (3) but now there are non-linear terms, e.g., $c_{1,2}$ is the regression coefficient for the interaction between variable positions 1 and 2.

In order to assess the performance of the linear and non-linear models, a synthetic data source known as the NK landscape was used (Kauffman and Levin, 1987). As mentioned above, N is the number of variable positions in a simulated protein and K is the epistatic coupling between residues. In addition, the synthetic data set was generated in silico.

This data set was used to generate an initial training set with S=40 synthetic samples, with N=20 variable positions and K=1 (to reiterate, for K=1 each variable position is functionally coupled to one other variable position). In generating the randomized proteins, each variable position had an equal probability of containing the dummy variable +1 or −1. The residue-residue interactions (represented by cross-products) and actual activities were known for each member of the synthetic training set. Another V=100 samples were generated for use in validation. Again, the residue-residue interactions and activities were known for each member of the validation set.

The training sets were used to construct both linear and non-linear models. Some non-linear models were generated with selection of the cross-product terms and other non-linear models were generated without selection of such terms. The models for FIGS. 3A-F were generated using a genetic algorithm modeling method, while the models for FIGS. G-H were generated using stepwise modeling method. Although the quantitative advantage of models having both linear and non-linear terms relative to models having only linear terms differ between genetic algorithm and stepwise modeling methods, the results indicate the generalizable advantage of models with non-linear terms, regardless of the modeling methods. Indeed, it is not intended that the present invention be limited to any particular methods, as any suitable modeling methods find use in the present invention.

For the training set size of S=40 described above, the linear model was capable of correlating the measured and predicted values reasonably well, but demonstrated weaker correlation when validated against data not seen in the training set (see FIG. 3A). As shown, the dark data points represent the observed activity of 40 training data points vs. the predictions made by a linear model. The light data points represent the predictions made by the same model constructed from the 40 training samples and used to predict the validation samples V, none of which were seen in the original training set. The validation set provides a good measure of the true predictive capacity of the model, as opposed to the training set, which can suffer from the model overfit problem especially for the non-linear cases described below.

This result for the S=40 training set described above is notable, considering that a linear model was used to model a non-linear fitness landscape. In this case, the linear model could, at best, capture the average contribution to fitness for the choice of a given residue. Given a sufficient number of average contributions taken into consideration in combination, the linear model roughly predicts the actual measured response. The validation results for the linear model were marginally better when the training size was increased to S=100 (see FIG. 3B). The tendency of relatively simple models to underfit data is known as "bias."

When the non-linear model was trained using only S=40 samples, the correlation with the training set members was excellent (see FIG. 3C). Unfortunately, in this illustrative example, the model provided limited predictive power outside the training set, as evidenced by its limited correlation with measured values in the validation set. This non-linear model, with many potential variables (210 possible), and limited training data to facilitate identification of the proper cross-product terms, was able to essentially just memorize the data set it was trained on.

This tendency of high complexity models to overfit the data is known as "variance." The bias-variance tradeoff represents a fundamental problem in machine learning and some form of validation is almost always required to address it when dealing with new or uncharacterized machine learning problems.

However, when the non-linear model was trained using a larger training set (S=100) as shown in FIG. 3D, the non-linear model performed exceedingly well for both the training prediction and, more importantly, the validation prediction. The validation predictions were sufficiently accurate that most of the data points are obscured by the dark circles used to plot the training set.

For comparison, FIGS. 3E and 3F show the performance of non-linear models prepared without careful selection of the cross-product terms. Unlike the models in FIGS. 3C and 3D, every possible cross-product term was chosen (i.e., 190 cross-product terms for N=20). As shown in these Figures, the ability to predict validation set activity is relatively poor compared to that of the non-linear models generated with careful selection of cross-product terms. This poor ability to predict validation data is a manifestation of overfitting.

FIGS. 3G and 3H respectively show the predictive power indicated by residuals of a linear model and a stepwise, non-linear model for data simulated in silico. The stepwise non-linear model was implemented as generally described above and more specifically below.

To test these models, simulated data were created. A random number generator R was created based upon a normal distribution with a mean MN and standard deviation SD. Then a set of 10 mutations were defined. The naming of these were M1, M2 . . . M10 (this naming scheme is arbitrary). This step simulates the creation of diversity Each mutation represented an amino acid change at a given position within a protein sequence, and each position is independent of the other positions. Each mutation above had a random activity value A assigned based upon R (MN=0, SD=0.2). Six mutations above were chosen and paired together into three pairs P. These pairs represented epistatic interactions between mutations.

An activity value AP was assigned to each pair P based upon R (MN=0, SD=0.2). A library L of 50 variants was constructed in which each variant contained a random number of mutations M defined above—the random number of mutations was defined by the rounded absolute value of R (MN=4, S=0.25). This step simulates library construction and sequencing.

The activity of each variant in L was calculated by first adding to 1.0 (a defined activity of the wild-type, no mutation sequence) the value of the activity from each pair-wise mutation PA (if both mutations were present) followed by adding the values of the remaining single mutations (A). Assay noise was simulated by adding to the final value for each variant a random value from R (MN=0, SD=0.005). This step simulates screening of variants.

A linear model LM was constructed based upon the data from the last step. This model contained ten independent variables/coefficients, each representing one mutation of M. The linear model was then fit using ordinary least squares regression and data obtained above.

A stepwise addition method was used to select a model MM based upon the data obtained above, with the base model being LM, using AIC as the selection criterion, and selecting models which only contain coefficients representing single mutations and pair-wise interactions. See Model Selection description below for further details of the model selection method. The best model selected by AIC was fit using ordinary least squares regression.

To assess the predictive capability of the linear model and nonlinear model, the procedures described above were repeated 20 times. The prediction of the models were plotted against the simulated data, wherein FIG. 3G shows the linear model and FIG. 3H shows the step-wise non-linear model. The models were used to predict the values of single mutations described above. This prediction was performed by using the models to predict a variant containing only one mutation of interest and subtracting 1.0 (wild-type). As apparent from FIGS. 3G and 3H, the non-linear model more accurately predicts values, having a more linear trend and smaller residuals.

D. Model Selection

After a base sequence activity model is generated, the process refines the model by adjusting the values of the coefficients in the terms of the models to minimize the residual error between the model prediction and the observed data. See block 107. This kind of adjustment is also referred to as model fitting. Various methods of model fitting known in the art can be used. For instance, a genetic algorithm can be used to adjust the values of the coefficients. For additive models, various regression techniques can be used to fit the model.

In some embodiments of the invention, the process also refines the model by selecting the appropriate terms to include in or exclude from the model, so as to minimize residual errors and/or to improve the model's predictive power. See block 107. Since the models considered have terms all selected from the same pool of terms, this refining process is also known as model selection among nested models. Some embodiments of the invention use a genetic algorithm to select the appropriate terms. Additionally or alternatively, some embodiments of the invention iteratively adds or subtracts interaction terms from a pool of available interaction terms to or from the base model and evaluates the resulting new models for improvement over the base model to produce a final model.

Adjusting model coefficient values and selecting model terms to improve the predictive power of the models are both known as model optimization techniques. Exemplary algorithms for generating sequence-activity models according to the operations in blocks 105 and 107 are presented below. Such techniques include, but are not limited to, genetic algorithm and step-wise techniques that bias against inclusion of additional interaction terms in a model. However, it is not intended that the present disclosure be limited to these specific examples.

Genetic Algorithm

Some embodiments of the invention provide methods of using a genetic algorithm to select one or more terms of the sequence-activity models. Other embodiments provide methods of using a genetic algorithm to adjust the values of the coefficients to fit the models to the obtained data.

In a genetic algorithm, an appropriate fitness function and an appropriate mating procedure are defined. The fitness function provides a criterion for determining which models (combinations of cross-product terms) are "most fit" or having the highest predictive power (i.e., likely to provide the best results). In some embodiments, the algorithm provides a mechanism to search through parameter spaces to find the optimal values for parameters (i.e. coefficients for the sequence-activity models). In these embodiments, each of the individuals or chromosomes of a population includes genes representing all the coefficients being tested, and the gene having chosen values in defined ranges for the coefficients. For instance, a chromosome can have a gene representing a coefficient for Gly at position 131, having the value of 0.4.

In some embodiments, genetic algorithm may also be used to select appropriate terms for the models. One example of such an algorithm can be similar to the previous example, except that all individuals/chromosomes include all the genes representing all eligible parameters (coefficients), and the values of the genes are allowed to assume the value of 0. If a coefficient converges to 0 for a term among the fittest individuals at the end of the algorithm, that term is dropped from the model. Conversely, that term is preserved.

In other embodiments, the mating procedure provides a mechanism for introducing new combinations of interaction terms from successful "parental" models in a previous generation.

One example of a genetic algorithm for fitting a model to the data by adjusting the values of the coefficients, and optionally, selecting suitable terms to maximize the predictive power of the model. This example is described with reference to FIG. 1B. This algorithm begins with a first generation comprising multiple possible models, all having variable values of the coefficients, where some models do a better job of representing physical reality than others. See block 131. The first and each successive generation is represented as a number of models (also referred to as individuals or chromosomes) in a "population". Each model/chromosome includes genes representing the coefficient values of all the terms being tested in this generation. The genetic algorithm proceeds towards convergence by marching through successive generations of models, each characterized by a different set of values for the coefficients of the terms of the sequence-activity model.

The fitness of each model in a generation is calculated for a training set of polypeptides (having known sequences and associated activities). See block 133, 135, 141, and 143 of FIG. 2. In some embodiments, the fitness is measured by the mean squared error. In other embodiments, the fitness is measured by likelihood. In additional embodiments, the fitness is measured by AIC or BIC.

After each combination of terms in a particular generation is evaluated for its predictive power (i.e., decision 143 is answered in the negative), the genetic algorithm is checked for convergence or other criteria (such as a fixed number of generations) to determine if the process should continue for a further generation. See block 145. Assuming that the genetic algorithm has not yet met the criterion to stop, the models of the current generation are ranked. Those that do the best job of predicting activity may be preserved and used in the next generation. See block 147. For example, an elitism rate of 10% may be employed. In other words, the top 10% of models (as determined using the fitting function and measured by, e.g., mean squared error or AIC) are set aside to become members of the next generation. The remaining 90% of the members in the next generation are obtained by mating "parents" from the previous generation. See blocks 149, 151, and 153.

As indicated, the "parents" are models selected from the previous generation. See block 149. Generally, the selection is weighted toward more fit members of the previous generation, although there may be a random component in their selection. For example, the parent models may be selected using a linear weighting (e.g., a model that performs 1.2 times better than another model is 20% more likely to be selected) or a geometric weighting (i.e., the predictive differences in models are raised to a power in order to obtain a probability of selection). In some embodiments, the parents are selected by simply choosing the best performing two or more models from the ranking of models in the previous generation and no other models are selected. In these embodiments, all selected models from the prior generation are mated. In other embodiments, some models from the prior generation are selected for inclusion in the next generation model without mating, and other poorer performing models from the prior generation are randomly selected as parents. These parents may be mated with each other and/or with the better performing models selected for inclusion as such in the next generation.

After a set of parent models has been selected, pairs of such models are mated (block 151) to produce children models by providing some genes (coefficient values) from one parent and other coefficient values from the other parent. In one approach, the coefficients of the two parents are aligned and each value is considered in succession to determine whether the child should take the term from parent A or from parent B. In one implementation, the mating process begins with parent A and randomly determines whether a "cross over" event should occur at the first term encountered. If so, the term is taken from parent B. If not, the term is taken from parent A. The next term in succession is considered for cross over, etc. The terms continue to come from the parent donating the previous term under consideration until a cross over event occurs. At that point, the next term is donated from the other parent and all successive terms are donated from that parent until another cross over event occurs. To ensure that the same term is not selected at two different locations in the child model, various techniques may be employed, e.g., a partially matched cross over technique. In some embodiments, instead of using the coefficient values of the genes from either parents, the average of the values of the gene may be adopted for a child chromosome.

In some embodiments of the invention, a genetic algorithm also employs one or more mutation mechanisms to generate further diversity of the models (block 152), which helps to explore regions of a parameter space that are not covered by any existing genes in the parent generation. On the flip side, mutation mechanisms affect convergence, such that the higher the mutation rate or the larger the mutation range, the longer it will take to converge (if ever). In some embodiments, mutation is implemented by random selection of a chromosome/model, and a random selection of a coefficient of said chromosome, which is then randomly changed. In some embodiments, the randomly changed values of coefficients are drawn from a random uniform distribution with a defined range. In other embodiments, the randomly changed values of coefficients are drawn from a random normal distribution with a defined range.

After each interaction term has been considered, a child "model" is defined for the next generation. Then another two parents are chosen to produce another child model, and so on. Eventually, after a complete generation has been selected in this manner (block 153), the next generation is ready for evaluation, and process control then returns to block 133, where the members of the next generation are evaluated as described above.

The process continues generation-by-generation until meeting the stop criterion, (i.e., decision block 145 is answered in the positive. At that point, at least one of the top ranked models is selected from the current generation as the overall best model. See block 155. Convergence can be tested by many conventional techniques. Generally, it involves determining that the performance of the best model from a number of successive generations does not change appreciably. Examples of decision criteria or convergence include but are not limited to the number of generations generated so far, the activity of top proteins from the current library, the magnitude of activity desired, and the level of improvement observed in last generation of models.

An example is next presented to show the use of a genetic algorithm to refine a model by adjusting the values of the model's coefficient. For each model, coefficients are selected for each possible mutation (i.e., for each term in the model).

The coefficient values in the seed population are randomly selected within certain maximum and minimum bounds. Each model is then used to predict activity from each variant sequence in a training set of variants. For a given model, all calculated values of activity are compared against the observed values of activity and a residual of mean squared error is generated. This procedure is conducted for each of the randomly generated models in the first generation. Those models having the smallest residual error are selected for inclusion in the next generation.

TABLE V

Chromosomes of a Genetic Algorithm for Sequence of TABLE I

| | $C_{10Asp}$ | $C_{10Lys}$ | $C_{166Ser}$ | $C_{166Leu}$ | $C_{166Ile}$ | $C_{175Val}$ | $C_{340Ala}$ |
|---|---|---|---|---|---|---|---|
| $Ch_1$ | 1.15 | 0.21 | −0.1 | 1.1 | 2.3 | −0.001 | 1.0 |
| $Ch_2$ | 1.2 | −0.8 | 0.5 | 0.1 | 1.9 | 0.1 | 1.8 |
| $Ch_3$ | 0.1 | 1.1 | 0.05 | 0.65 | 3 | 1.2 | 1.4 |
| ... | | | | | | | |
| $Ch_{n-1}$ | 0.17 | 2.01 | 2 | −0.1 | 0.2 | 0.76 | 0.37 |
| $Ch_n$ | 3.1 | 1.6 | 0.55 | 1.2 | 2.6 | 2.0 | −0.3 |

For this example, the genetic algorithm evaluates the fitness of each chromosome using model equation to calculate the expected activity for an individual chromosome.

$$y_n = (1 + C_{10Asp}X_{10Asp}) * (1 + C_{10Lys}X_{10Lys}) *$$
$$(1 + C_{166Ser}X_{166Ser}) * (1 + C_{166Leu}X_{166Leu}) *$$
$$(1 + C_{166Ile}X_{166Ile}) * (1 + C_{175Val}X_{175Val}) * (1 + C_{340Ala}X_{340Ala})$$

For chromosome/model 2, expected activity y=(1+1.15)*(1−0.001)*(1+1.0). This expected activity of the model is compared against the observed sequence activity, and the fitness of the individual is calculated from the Mean Squared Error (MSE).

Genetic algorithm then chooses the top 20% models that have the lowest MSE of the current generation. Typically, the next generation involves mating the selected models from the previous generation. Mating may simply involve selecting some coefficients from one "parent" model and the remaining coefficients from a different "parent". The selection of terms may be conducted as a "crossover" or other genetic operation.

The next-generation models (produced by mating) are then each used to predict activity in the training set of variants. The predicted activities are compared against observed values of activity and residual errors generated. The second generation models having the best activity are selected for a further generation of mating and selection. The process continues until the model performance converges. For example, the genetic algorithm runs for 50 to 100 generations. At that point, at least one of the top ranked models is selected from the current generation as the overall best model. The fittest model determines the values of the coefficients for the sequence-activity model.

Stepwise Selection

In some embodiments, stepwise addition or subtraction methods are used to prepare models with interaction terms. By implementing operation shown in block 107 of FIG. 1, a final model with high predictive power including interaction terms is provided by stepwise addition or subtraction of interaction terms from a base model.

Figure 4A:
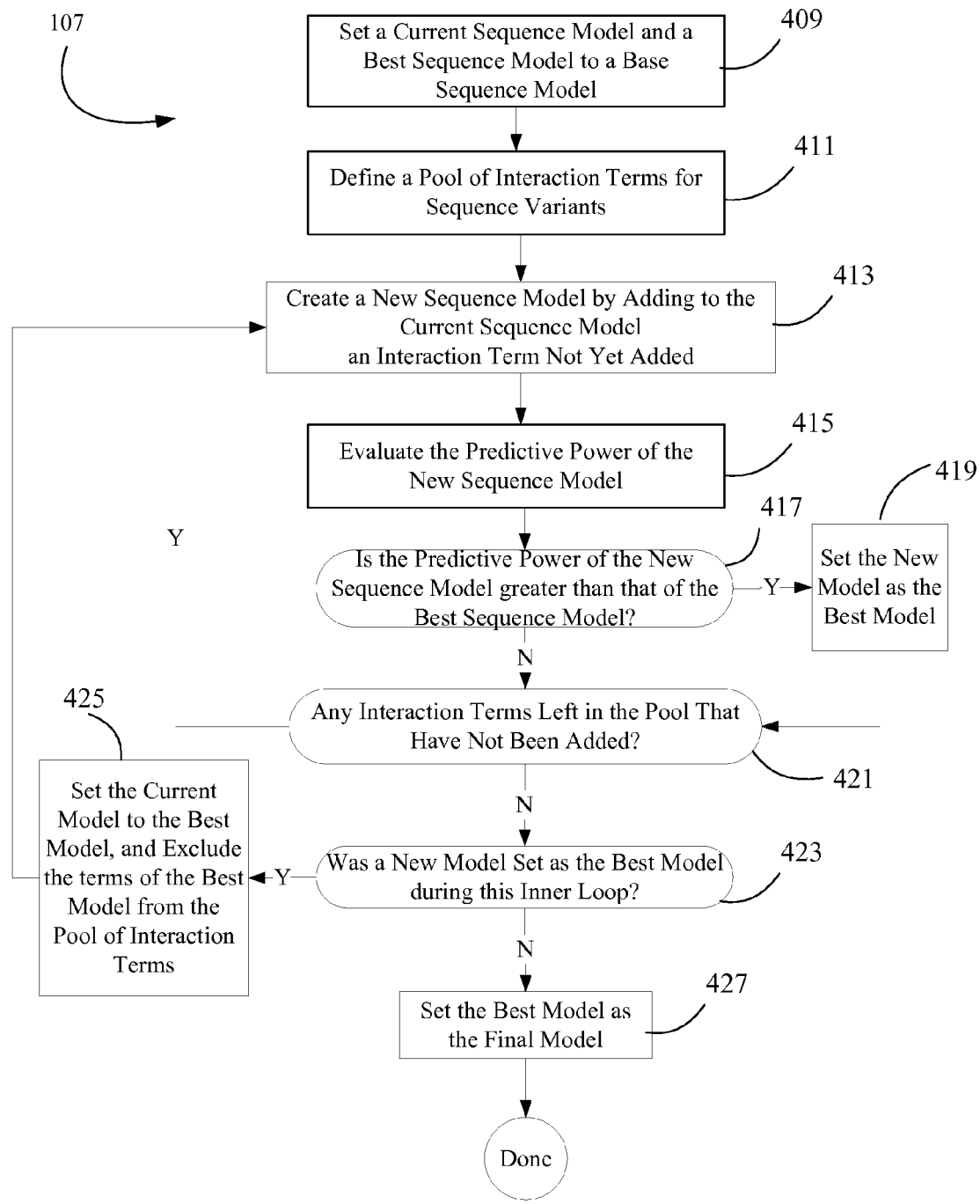
FIG. 4A-4B illustrates flow charts of processes implementing stepwise addition and subtraction methods for preparing a sequence-activity model.

FIG. 4A provides a flow chart of an implementation of operation of block 107 of FIG. 1 by adding interaction terms to a base model and evaluating the new models to create a final best model.

In this example, the base sequence model includes no interaction terms. The method first sets a current sequence model and a best sequence model to the base sequence model, block 409. The method defines a pool of interaction terms for sequence variants. These interaction terms may include any number of pairwise or higher order interactions of two or more amino acid residues. See block 411. Although block 409 is illustrated as occurring before block 411, the order of the two steps is not important. In some embodiments, the pool of interaction terms includes factorial combinations of all amino acid residues of interest. In some additional embodiments, at least all pairwise interaction terms are included. In some further embodiments, pairwise and three-way interaction terms are included.

After creating a base model, the method selects an interaction term that has not yet been tested from the pool. The method then creates a new sequence model by adding the selected interaction term to the current sequence model. See block 413. The method then evaluates the predictive power of the new sequence model using a model selection method having a bias against including additional interaction terms. See block 415. The method determines whether or not the predictive power of the new sequence model is greater than that of the best sequence model. See decision block 417. As an example, the method may use a technique employing "likelihood" determination (e.g., AIC) as a model selection criterion. In such cases, only a model having an AIC value smaller than the previously tested model is considered to have higher predictive power.

In some embodiments, the selection method biases against models with more parameters. Examples of such selection methods include, but are not limited to Akaike Information Criterion (AIC) and Bayesian Information Criterion (BIC), and variations thereof. For instance, AIC can be calculated as:

$$AIC = -2 \log_e L + 2k$$

where L is the likelihood of a model given a data set, and k is the number of free parameters in a model.

In some embodiments, the likelihood of a model given a dataset may be calculated by various methods, including but not limited to the maximum likelihood method. For instance, for a binary dependent variable where an activity either is present or is absent for one observation, the likelihood of the model can be calculated as:

$$L(\text{model} | \text{data}) = \prod_{i=1}^{n} \frac{(a_i + b_i)!}{a_i! b_i!} p_i^{a_i} (1 - p_i)^{b_i}$$

where n is the total number of data points in a data set; $a_i$ and $b_i$ are the number of observed trials comprising the $i^{th}$ condition; p is the probability of a dependent variable being observed as predicted by the model.

In some embodiments involving a series of nested models, as in regression models with progressively more interaction terms (and associated coefficients) than a base model, more complex models provide equally good or better fits than simpler ones even if the extra coefficients are spurious, because the more complex model enjoys extra degrees of freedom. In some embodiments, AIC penalizes the more complex model to the extent that the gain in goodness of fit is more than offset by the cost of spurious parameters. In model selection, a smaller value of AIC indicates a better model.

In the example shown in FIG. 4A, if the predictive power of the new sequence model is greater than that of the best sequence model, then the method sets the new model as the best model. See block 419. Then, the method checks whether any additional interaction terms are left in the pool that have not been tested. See decision block 421. If so, the process reverts back to block 413, thereby forming an inner loop to test all of the available interaction terms available in the interaction pool. Through iterations of the inner loop, a single best interaction term can be found and added to the model.

After all interaction terms have been tested, and the inner loop ends, a best model having one additional interaction term is identified, given that a model having greater predictive power than the previous best model does exist. See decision block 423. In such embodiments, the method sets the current model to the best model, and excludes the interaction terms of the best model from the available pool of interaction terms. See block 425. Then, the method loops back to block 413. This outer loop searches for the next best interaction term that can improve the model's predictive power. If such an interaction term is found, the search for the next best interaction term continues in the outer loop, until no new model having a predictive power greater than that of the previous best sequence model is identified.

When no more interaction terms can be found to improve the model, the method sets the best model as the final model. See block 427. The search for a best model given the sequence and activity data is finished. The model is then used to predict the activities of new sequences. Such predictions can guide the selection of sequences for further variation and testing.

In certain embodiments, each of the available interaction terms in the pool of interaction terms is treated as having potentially equal impact on the quality or predictive power of the model. In other words, in implementation, each of the available interaction terms in the pool is equally likely to be selected for consideration during a particular iteration. In some embodiments, the available interaction terms are selected randomly or in some arbitrary orders. In some other embodiments, the interaction terms are biased or weighted in such a manner that some terms are more likely to be selected for consideration than others during a given iteration. The bias or weighting can, in certain embodiments, be applied on the basis of physical or theoretical information about the interactions. For example, it may be known that mutations in two particular areas of a protein are likely to be physically proximate to one another and thereby interact. Interaction terms pertaining to residues in these two general areas could be biased for selection during the iterative process of refining the model.

Pseudo code illustrating processes similar to that for FIG. 4A follows:

```
SET Coeff = Interaction Terms to Test
Best = Baseline Model
count = 1
WHILE count >0
    count = 0
    BestFromRound = Best
    BestCoefficient = NULL
    FOR each Interaction Term in Coeff
        TestModel = (best + Interaction Term)¹
        IF TestModel BETTER THAN BestFromRound THEN²
            BestFromRound = TestModel
            Count++
            BestCoefficient = Interaction Term
        ENDIF
    ENDFOR
    IF count >0 THEN
        Best = BestFromRound
        Remove BestCoefficient FROM Coeff³
    ENDIF
ENDWHILE
```

Figure 4B:
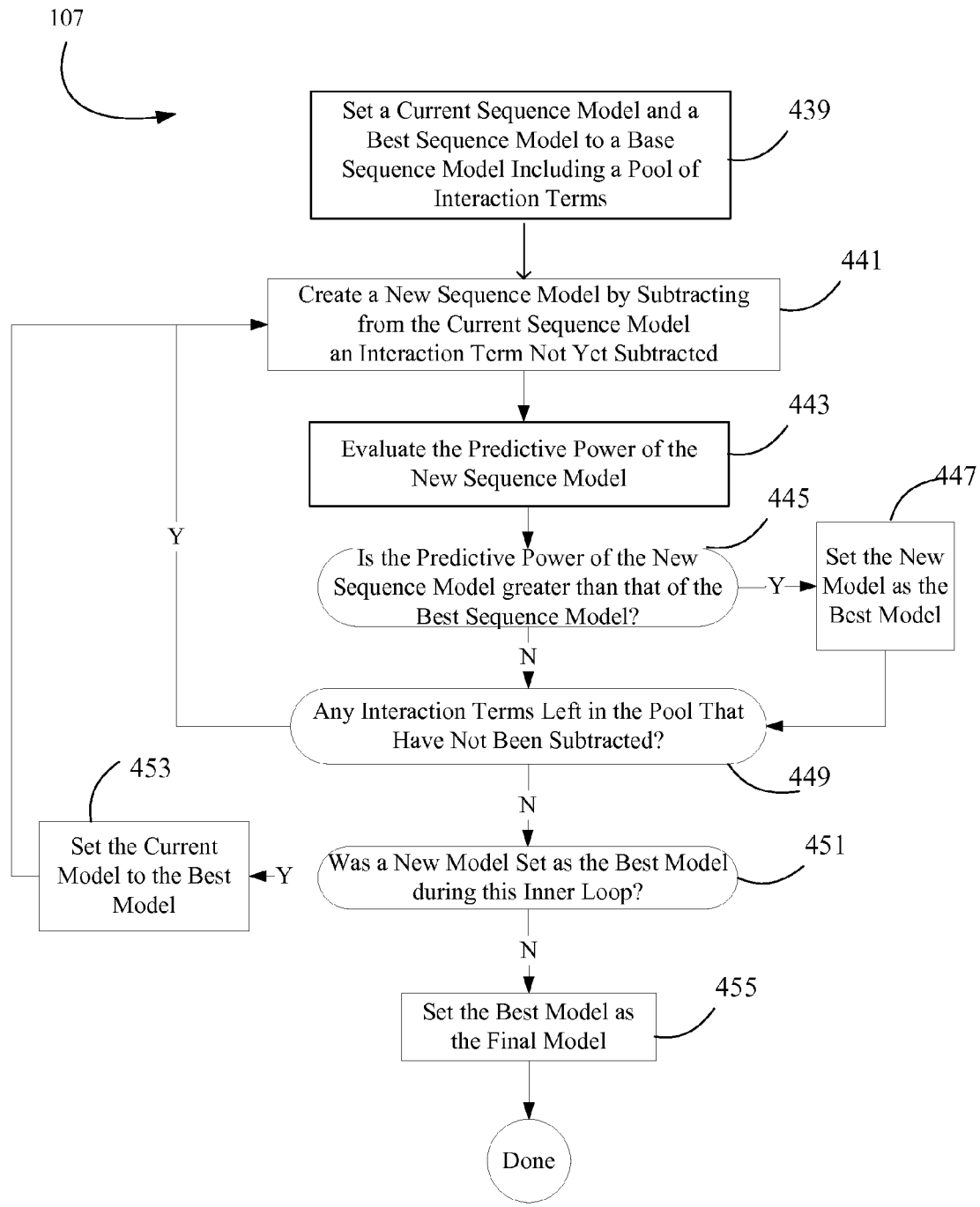

Item 1 adds the test interaction term to the regression model
Item 2 represents Model Comparison, one or more of Akaike Information Criteria (AIC), Bayesian Information Criteria (BIC), Crossvalidation (mean error), ANOVA, or coefficient contribution.
Item 3 is provided to avoid duplicate Interaction Term tests FIG. 4B provides a flow chart showing an embodiment of operation shown in block 107 of FIG. 1. In this process, interaction terms are subtracted from a base model that includes all possible interaction terms from a pool of such terms to create a final best model.

In this embodiment, the base sequence model includes all interaction terms within a defined pool. The method first sets a current sequence model and a best sequence model to be equal to the base sequence model at the beginning of the process, block 439. This embodiment is similar to the last model described above in that the whole pool of interaction terms may include any number of pairwise or higher order interactions of two or more amino acid residues. In some embodiments, the pool of interaction terms includes factorial combinations of all amino acid residues that are of interest.

After creating a base model, the method selects an interaction term that has not yet been tested from the pool of terms already included in the base model. The method then creates a new sequence model by subtracting the selected interaction term from the current sequence model. See block 441. The method then evaluates the predictive power of the new sequence model using a model selection method having a bias against additional interaction terms. See block 443. The method evaluates whether or not the predictive power of the new sequence model is greater than that of the best sequence model. See decision operation shown in block 445. In some embodiments, AIC is used as the model selection criterion, such that a model having an AIC value smaller than the previously tested model is considered to have higher predictive power.

In this illustrative example, if the predictive power of the new sequence model is greater than that of the best sequence model, then the method sets the new model as the best model. See block 447. Next, the method checks whether any additional interaction terms are left in the pool that have not been tested (i.e., subtracted from the current sequence model). See decision block 449. If there are any untested terms, the method reverts to block 441, thereby forming an inner loop to test all of the available interaction terms available in the interaction pool. Through iterations of the inner loop, a single interaction term is identified. Dropping it from the model improves the model to the greatest extent (and lowering AIC by the largest margin, if AIC is used to measure the predictive power of the model).

After all interaction terms have been tested, and the inner loop ends, a best model having one fewer interaction term is identified, given that a model having greater predictive power than the previous best model does exist. See decision block 451. In this case, the method sets the current model to the best model. See block 453. Then, the method loops back to block 441. This outer loop searches for the next interaction term that can improve the model's predictive power by the largest margin. If such an interaction term is found, the search for the next interaction term to be subtracted continues in the outer loop, until no more new models having predictive powers greater than that of the previous best sequence model is identified.

When an inner loop is completed and no more interaction terms can be found to be subtracted to improve the model (i.e., decision operation shown in block 451 is answered in the negative), the method sets the last best model as the final model. See block 455. The search for a best model given the sequence and activity data is finished.

E. Alternative Modeling Options

Multiple additional variations on the above approach are within the scope of the disclosure. Indeed, it is not intended that the present invention be limited to any particular model, as any suitable model finds use in the present invention. As one illustrative example, the $x_{ij}$ variables are representations of the physical or chemical properties of amino acids—rather than the exact identities of the amino acids themselves (leucine versus valine versus proline . . . ). Examples of such properties include lipophilicity, bulk, and electronic properties (e.g., formal charge, van der Waals surface area associated a partial charge, etc.). To implement this approach, the $x_{ij}$ values representing amino acid residues can be presented in terms of their properties or principal components constructed from these properties. It is not intended that the present invention be limited to any particular property of amino acids, peptides, and/or polypeptides, as any suitable property finds use in the methods of the present invention.

In some additional embodiments, the $x_{ij}$ variables represent nucleotides, rather than amino acid residues. In these embodiments, the goal is to identify nucleic acid sequences that encode proteins for a protein variant library. By using nucleotides rather than amino acids, parameters other than activity (e.g., specific activity) can be optimized, as desired. For example, protein expression in a particular host or vector may be a function of nucleotide sequence. Two different nucleotide sequences may encode a protein having the same amino acid sequence, but one of the nucleotide sequences may lead to production of greater quantities of protein and/or the protein is more active. By using nucleotide sequences rather than amino acid sequences, the methods described herein can be used to optimize strains of microorganisms that exhibit improved gene expression properties and/or improved properties (e.g., specific activity, stability, etc.).

In some embodiments, the nucleotide sequence is represented as a sequence of codons. In some embodiments, models utilize codons as the atomic unit of a nucleotide sequence such that the predicted activities are a function of the various codons present in the nucleotide sequence. Each codon, together with its position in the overall nucleotide sequence serves as an independent variable for generating sequence-activity models. It is noted that in some cases, different codons for a given amino acid are expressed differently in a given organism. In some embodiments, each organism has a preferred codon, or distribution of codon frequencies, for a given amino acid. By using codons as the independent variables, the embodiment accounts for these preferences. Thus, the embodiment can be used to generate a library of expression variants (e.g., where "activity" includes gene expression level of a particular host organism).

In some embodiments, the methods include the following operations: (a) receiving data characterizing a training set of a protein variant library; (b) developing an interaction sequence-activity model that predicts activity as a function of nucleotide types and corresponding positions in the nucleotide sequence, based on the data obtained in (a); (c) using the sequence-activity model to rank the positions in a nucleotide sequence and/or nucleotide types at specific positions in the nucleotide sequence in order of impact on the desired activity; and (d) using the ranking to identify one or more nucleotides, in the nucleotide sequence, that are to be varied or fixed, in order to improve the desired activity. As indicated, in some embodiments, the nucleotides to be varied encode specific amino acids.

In some other embodiments, the methods involve use of different techniques for ranking or otherwise characterizing residues in terms of their importance related to a certain property. As described above for linear or non-interaction models, the magnitudes of regression coefficients were used to rank residues. Residues having coefficients with large magnitudes (e.g., 166 Ile) were viewed as high-ranking residues. This characterization was used to decide whether or not to vary a particular residue in the generation of a new, optimized library of protein variants. For interaction models, the sensitivity analysis was more complex, as described herein.

PLS and other techniques provide additional information, beyond regression coefficient magnitude, that can be used to rank specific residues or residue positions. Techniques such as PLS and Principal Component Analysis (PCA) or PCR provide information in the form of principal components or latent vectors. These represent directions or vectors of maximum variation through multi-dimensional data sets such as the protein sequence-activity space employed with the embodiments of the present invention disclosed herein. These latent vectors are functions of the various sequence dimensions; i.e., the individual residues or residue positions that comprise the protein sequences comprising the variant library used to construct the training set. Latent vectors therefore comprise a sum of contributions from each of the residue positions in the training set. Some positions contribute more strongly to the direction of the vector. These are manifested by relatively large "loads," i.e., the coefficients used to describe the vector. As a simple illustrative example, a training set may be comprised of tripeptides. In this example, the first latent vector comprises contributions from all three residues.

Vector 1=$a$1(residue position 1)+$a$2(residue position 2)+$a$3(residue position 3)

The coefficients, a1, a2, and a3, are the loads. Because these reflect the importance of the corresponding residue positions to variation in the dataset, they can be used to rank the importance of individual residue positions for purposes of "toggling" decisions, as described above. Loads, like regression coefficients, may be used to rank residues at each toggled position. Various parameters describe the importance of these loads. Some embodiments utilize methods such as Variable Importance in Projection (VIP) to make use of a load matrix. This load matrix is comprised of the loads for multiple latent vectors taken from a training set. In Variable Importance for PLS Projection methods, the importance of a variable (e.g., residue position) is computed by calculating VIP. For a given PLS dimension, a, $(VIN)_{ak}^2$ is equal to the squared PLS weight $(w_{ak})^2$ of a variable multiplied by the percent explained variability in y (dependent variable, e.g., certain function) by that PLS dimension. $(VIN)_{ak}^2$ is summed over all PLS dimensions (components). VIP is then calculated by dividing the sum by the total percent variability in y explained by the PLS model and multiplying by the number of variables in the model. Variables with a VIP larger than 1 are the most relevant for correlating with a certain function (y) and hence, are highest ranked for purposes of making toggling decisions.

In many embodiments, the present invention utilizes general linear regression methods to identify the effects of mutations in a combinatorial library on a sequence-activity of interest. Alternative modeling options and techniques, e.g., Bayesian regression, ensemble regression, bootstrapping, can be used in combination with or instead of the methods noted above. Indeed, it is not intended that the present invention be limited to any specific modeling options and/or techniques, as any suitable method(s) find use in the present invention.

Bayesian Linear Regression

In some embodiments of the present invention, Bayesian linear regression finds use. This method is an approach to linear regression in which the statistical analysis is undertaken within the context of Bayesian inference. When the regression model has errors that have a normal distribution, and if a particular form of prior distribution is assumed, the posterior probability distributions of the model's parameters can be determined using Bayesian inference techniques.

An ordinary least squares solution of a linear regression model estimates the coefficient vector and model error based on the likelihood function of the data using an analytical calculation method such as the Moore-Penrose pseudo inverse. This is a frequentist approach that assumes that there are sufficient observations of the data to represent the sequence-activity relation for all sequences. However, actual observations of a sample are almost never sufficient to represent all of the members of a population. This is especially problematic when the sample (or training set) size is limited. In the Bayesian approach, the sample data are supplemented with additional information in the form of a prior probability distribution. The prior belief about the parameters is combined with the data's likelihood function according to Bayes theorem to yield the posterior belief about the parameters. The prior belief can take different functional forms depending on the domain and the information that is available a priori.

For instance in some embodiments, Bayesian regression can use prior information to weight coefficients before model fit. In some embodiments, sequence/activity data taken from a previous round of directed evolution, e.g., a round performed using the parental or reference backbone and at least some of the mutations used in the previous rounds, can be used to weight linear coefficients. Further, predictions of the epistatic relationship between two or more mutations can be used to weight interaction coefficients. One of the main advantages to this approach is the inclusion of prior information to direct model predictions.

One illustrative example of a source of prior information is a model with independent and interaction terms for each of multiple mutations to a reference backbone. In some embodiments, the data are obtained from a collection of variants that contains one mutation per variant.

Additional examples of prior information that find use in the present invention include, but are not limited to intuitive or physical information about the role of certain mutations or types of mutations. Regardless of the source, the prior information serves as a preconceived notion of the relationship between sequence and activity.

In some embodiments for estimating the parameters of a model, Bayesian linear regression uses Monte Carlo simulations such as Gibbs Sampling or Metropolis algorithms to fit the model given the data. Gibbs Sampling is a Markov chain Monte Carlo algorithm for obtaining a sequence of observations which are approximately from a specified multivariate probability distribution (i.e. from the joint probability distribution of two or more random variables), when direct sampling is difficult.

Figure 5:
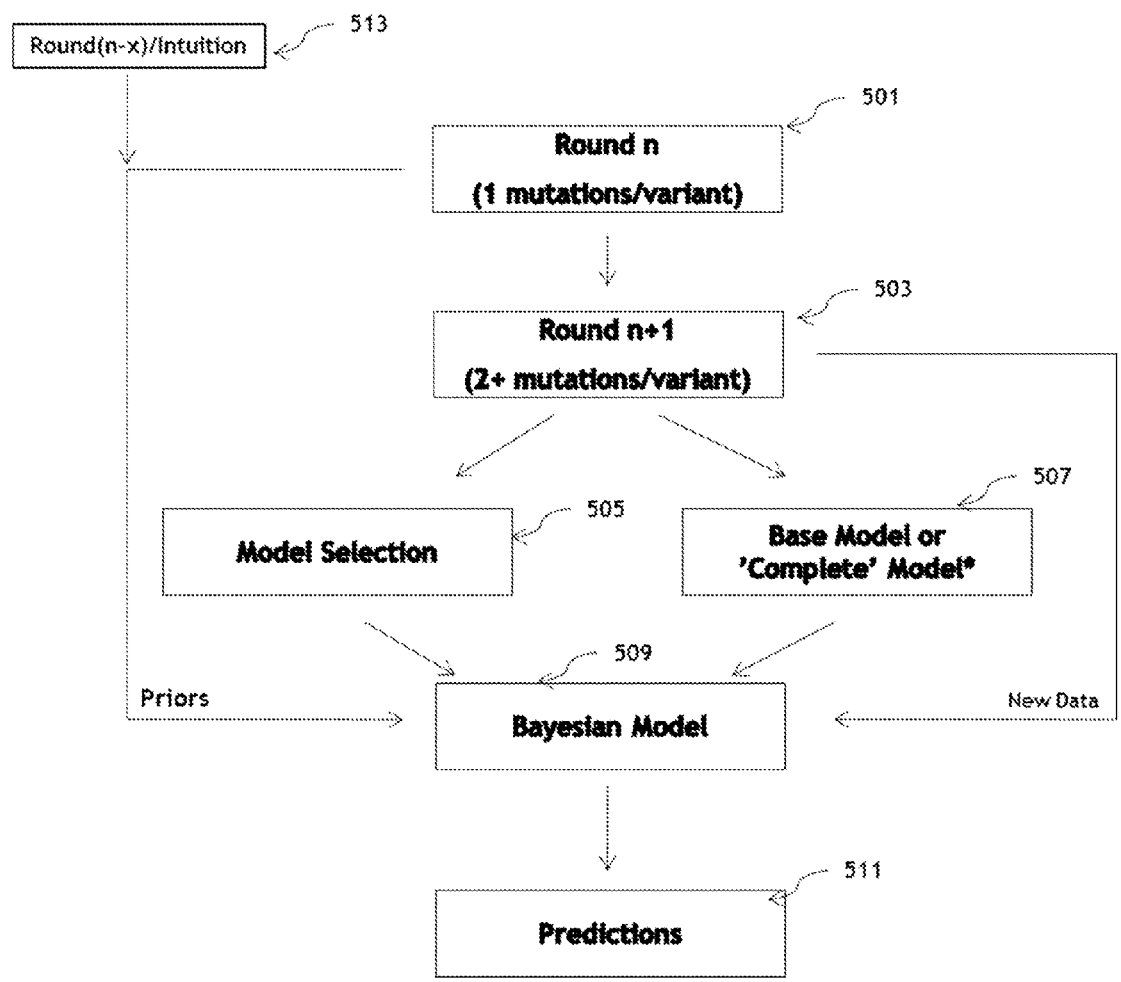
FIG. 5 illustrates a flow chart of a process implementing Bayesian regression in directed evolution of sequence variants in accordance with an embodiment.

FIG. 5 is a flow chart illustrating the use of Bayesian regression in guided evolution of variant libraries. Each round of sequence evolution includes mutations based on the sequences from a previous round, which may be guided by knowledge such as a sequence-activity model. At round n of the evolution as in block 501, for instance, there is one mutation per variant. The next or n+1 round of evolution is the current round, as shown in block 503. There is at least one new mutation for each variant, amounting to two or more mutations per variant. Bayesian regression is implemented at this round in this illustrative example.

The sequence variants of round n+1 provides a training set of data for new models. The new models can comprise a base model that includes only non-interaction terms for individual residues, or a complete model that contains all possible interaction terms/coefficients, as indicated in block 507. The new models may also comprise a model selected by various techniques, including the stepwise addition or subtraction techniques explained above, see block 505. The model may alternatively be selected using a genetic algorithm or bootstrap techniques as discussed below. These models are all based on the current/new data from the training set data of round n+1. Bayesian inference technique can be applied to these models, such that a model is based on both the probability function of current data and distribution of prior information. The prior information can come from data of the previous round of sequence variants, as in round n indicated by block 501. Information can also come from sequence-activity data from any previous round of evolution, or other prior intuition on knowledge, as indicated by block 513. The Bayesian regression model indicated by block 509 predicts activity based on information provided by current data and prior information, see block 511. Although FIG. 5 only illustrates application of the Bayesian regression technique to round n+1, it can be applied at various stages. It is also not intended that the present invention be limited to the specific steps provided in FIG. 5, as any suitable methods find use in the present invention.

Ensemble Regression

In some embodiments, the present invention utilizes an ensemble regression technique to prepare the sequence-activity model. An ensemble regression model is based on several regression models. The prediction of each model is weighted based upon a particular information criterion (IC), and the prediction of the ensemble is a weighted sum of the prediction of all the models it contains. In some embodiments, model development starts with a base model containing all of the interaction terms. Subsequent models are constructed by adding interaction coefficients in some or all possible combination. In some embodiments, the interaction coefficients are added in a step-wise process. Each model is fit to the data, and an IC is generated. Weight for each model is based upon the IC, which can be the IC itself, or a transformed version, e.g., log value, negated value, etc. Predictions can be made for an observation by generating the prediction of each model in the ensemble, and determining the ensemble prediction by taking the weighted mean of the prediction from each model. A complete ensemble contains all possible models, but can be trimmed to remove poor performing models by setting a threshold on either the number of models it contains or on IC.

The constituent models of the ensemble can be produced using various techniques. For instance, in some embodiments, genetic algorithm is used to create the constituent models. Sequence/activity data is used to produce a plurality of regression models, each of which has its own set of coefficients. The best models are selected according to fitness criterion (e.g., AIC or BIC). These models are "mated" to produce new hybrid models that are then evaluated for fitness and selected accordingly. In some embodiments, this process is repeated for multiple rounds of "computational evolution" to produce an ensemble of the best models. Alternatively, in some embodiments, the ensemble constituents are created by stepwise regression as described above, and the best n models are selected to form an ensemble.

Figure 6:
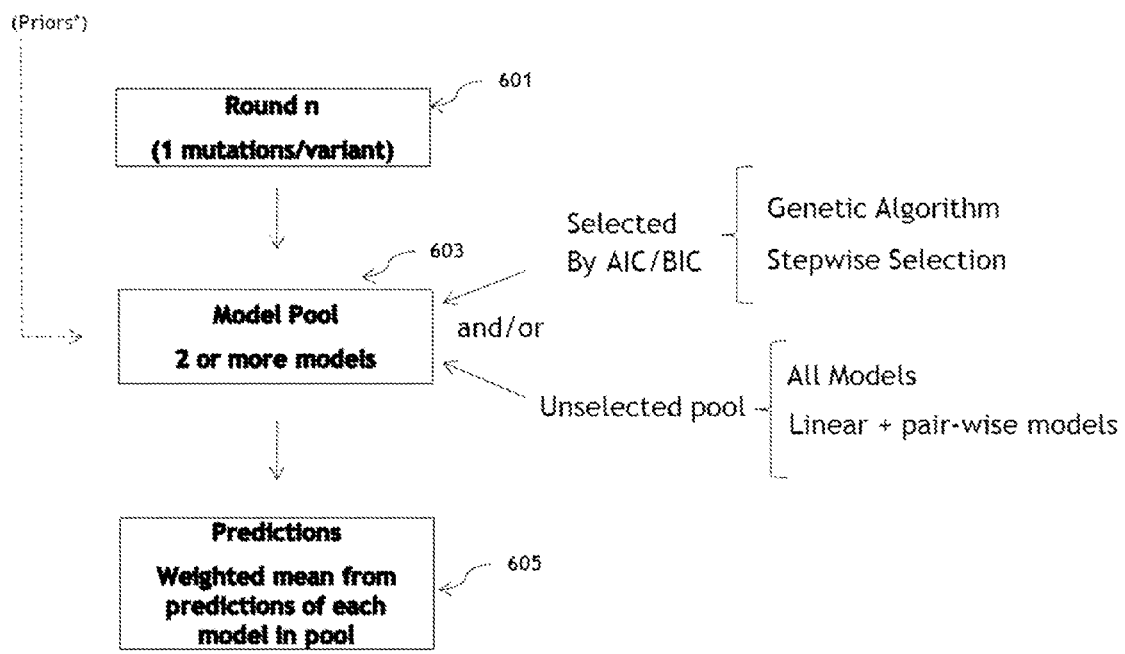
FIG. 6 illustrates a flow chart of a process implementing ensemble regression in directed evolution of sequence variants in accordance with an embodiment.

FIG. 6 provides a flow chart for a process that implements ensemble regression in directed evolution of sequence variants in accordance with an embodiment of the present invention. In this embodiment, the ensemble regression technique may be applied at any stage of multiple rounds of sequence evolution. For instance, at round n, sequence variants shown in block 601 provide a training set of data for various models to form a model pool as indicated by block 603. The models in the model pool may be models generated by a genetic algorithm and/or stepwise selection. In other embodiments, the model pool comprises n-fold cross validation models and/or bootstrapping models. In some embodiments, only models with superior predictive power are selected to enter the pool based on various model selection criteria, such as AIC or BIC.

Alternatively or additionally in some embodiments, models that have not been screened by model selection also enter the model pool. In one embodiment, all models with all non-interaction and interaction terms are entered into the model pool. For a large number of residues and a much larger number of factorial interactions among residues, this embodiment can be very computationally intensive. In some alternative embodiments, only models containing non-interaction terms and pairwise interaction terms are entered into the model pool. Regardless the inclusion method of the model pool, an ensemble model includes all the terms of its constituents. The model pool can contain any number of models, including, but not limited to Bayesian models, in which case, prior information can be incorporated into the ensemble.

In some embodiments, the ensemble predicts sequence activity based on the weighted mean of the coefficients of each model in the pool, wherein the weights are determined by the predictive power of the corresponding models, as indicated by block 605.

In some embodiments, an ensemble regression uses the following work flow: (1) provide an empty ensemble; (2) select a group size n of 1 or greater; (3) categorize data points into groups of size n, where data points are grouped without replacement; and (4) prepare an ensemble model to predict individual and interaction coefficients. In some embodiments, step (4) to prepare an ensemble model further comprises: a) removing data points of each group, wherein remaining data forms a training set and left out data forms a validation set; b) preparing a model by fitting the training set using stepwise regression; c) testing the model using the validation set, which provides an indication of the predictive ability of the model; d) add model to a pool of models that are used to generate an ensemble model as described above. Bootstrap Approach Other techniques for characterizing the predictive power of a model under consideration in a given iteration find use in the present invention. In some embodiments, these techniques involve cross validation or bootstrap techniques. In some embodiments, cross validation employs a set of observations used to generate the model but leaves some of the observations out to assess the strength of the model. In some embodiments, the bootstrap technique involves using a set of samples that are tested with replacement. In some embodiments, models generated by cross validation or bootstrapping can be combined into an ensemble model as described above.

In some additional embodiments, the methods rank residues not simply by the magnitudes of their predicted contributions to activity, but by the confidence in those predicted contributions as well. In some cases, the researcher is concerned with the generalizability of the model from one set of data to another set. In other words, the researcher wants to know whether or not the values of the coefficients or principal components are spurious. Cross validation and bootstrapping techniques provide measures to indicate the confidence level that the models are generalizable to various data.

In some embodiments, a more statistically rigorous approach is utilized in which the ranking is based on a combination of magnitude and distribution. In some of these embodiments, coefficients with both high magnitudes and tight distributions give the highest ranking. In some cases, one coefficient with a lower magnitude than another may be given a higher ranking by virtue of having less variation. Thus, some embodiments rank amino acid residues or nucleotides based on both magnitude and standard deviation or variance. Various techniques can be used to accomplish this. Indeed, it is not intended that the present invention be limited to any specific technique for ranking. One embodiment using a bootstrap p-value approach is described below.

Figure 7:
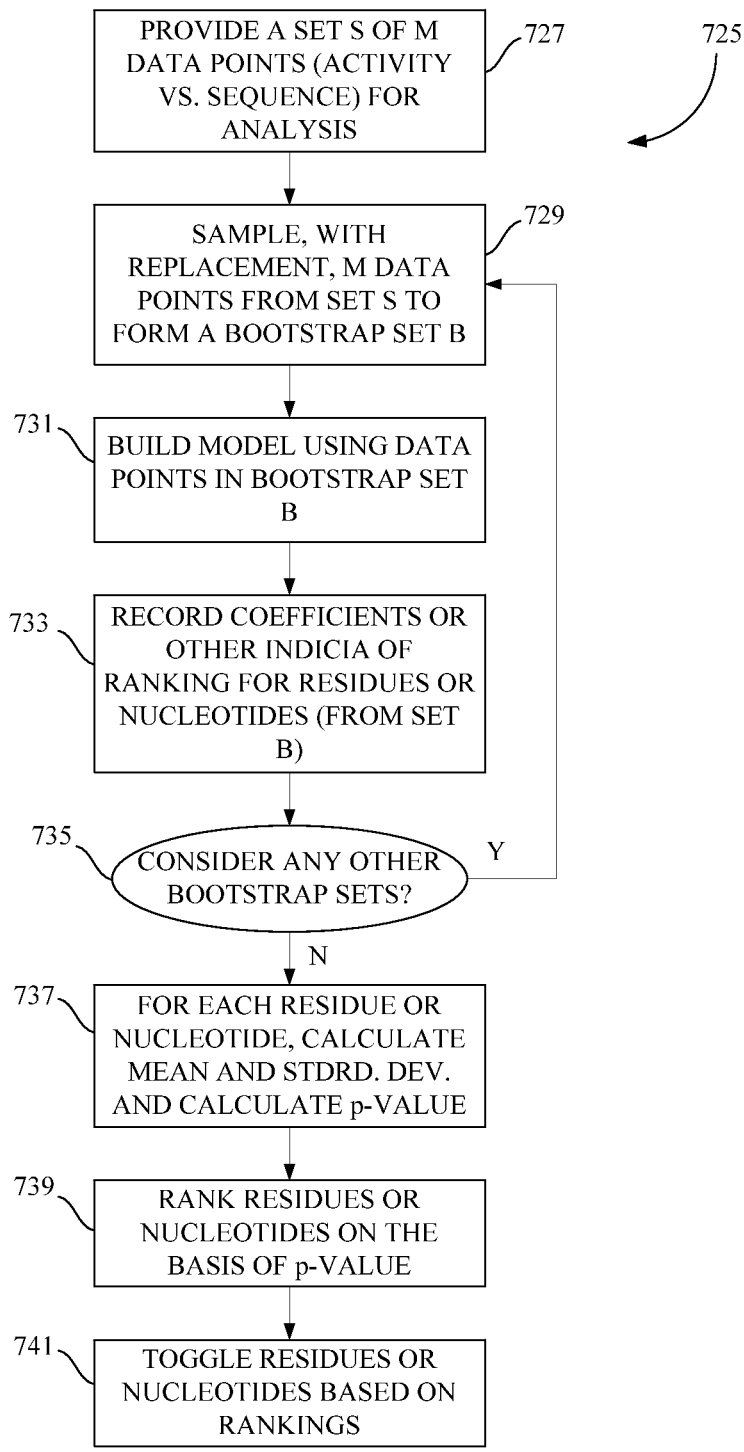
FIG. 7 is a flow chart depicting a bootstrap p-value method of generating protein variant libraries in accordance with an embodiment.

An illustrative example of a method that employs a bootstrap method is depicted in FIG. 7. As shown in FIG. 7, the method 725 begins at block 727, where an original data set S is provided. In some embodiments, this is a training set as described above. For example in some embodiments, it is generated by systematically varying the individual residues of a starting sequence in any manner (e.g., as described above). In the case illustrated by method 725, the data set S has M different data points (activity and sequence information collected from amino acid or nucleotide sequences) for use in the analysis.

From data set S, various bootstrap sets B are created. Each of these sets is obtained by sampling, with replacement, from set S to create a new set of M members—all taken from original set S. See block 729. The "with replacement" condition produces variations on the original set S. The new bootstrap set, B, will sometimes contain replicate samples from S. In some cases, the bootstrap set B also lacks certain samples originally contained in S.

As an illustrative example, a set S of 100 sequences is provided. A bootstrap set B is created by randomly selecting 100 member sequences from the 100 sequences in the original set S. Each bootstrap set B used in the method contains 100 sequences. Thus, it is possible that some sequences will be selected more than once and others will not be selected at all. Using the bootstrap set B produced from the set S of 100 sequences, the method next builds a model. See block 731. The model may be built as described above, using PLS, PCR, a SVM, stepwise regression, etc. Indeed, it is intended that any suitable method will find use in building the model. This model provides coefficients or other indicia of ranking for the residues or nucleotides found in the various samples from set B. As shown at a block 733, these coefficients or other indicia are recorded for subsequent use.

Next, at a decision block 735, the method determines whether another bootstrap set should be created. If yes, the method returns to block 729 where a new bootstrap set B is created as described above. If no, the method proceeds to a block 737 discussed below. The decision at block 735 turns on how many different sets of coefficient values are to be used in assessing the distributions of those values. The number of sets B should be sufficient to generate accurate statistics. In some embodiments, 100 to 1000 bootstrap sets are prepared and analyzed. This is represented by about 100 to 1000 passes through blocks 729, 731, and 733 of method 725. However, it is not intended that the present invention be limited to any particular number of bootstrap sets, as any number suitable for the desired analysis finds use.

After a sufficient number bootstrap sets B have been prepared and analyzed, decision 735 is answered in the negative. As indicated, the method then proceeds to block 737. There, a mean and standard deviation of a coefficient (or other indicator generated by the model) are calculated for each residue or nucleotide (including codons) using the coefficient values (e.g., 100 to 1000 values, one from each bootstrap set). From this information, the method can calculate the t-statistic and determine the confidence interval that the measured value is different from zero. From the t-statistic, it calculates the p-value for the confidence interval. In this illustrative case, the smaller the p-value, the more confidence that the measured regression coefficient is different from zero.

It is noted that the p-value is but one of many different types of characterizations that can account for the statistical variation in a coefficient or other indicator of residue importance. Examples include, but are not limited to calculating 95 percent confidence intervals for regression coefficients and excluding any regression coefficient for consideration for which 95 percent confidence interval crosses line zero. Basically, in some embodiments, any characterization that accounts for standard deviation, variance, or other statistically relevant measure of data distribution finds use. In some embodiments, this characterization step also accounts for the magnitude of the coefficients.

In some embodiments, a large standard deviation results. This large standard deviation may be due to various causes, including but not limited to poor measurements in the data set, and/or limited representation of a particular residue or nucleotide in the original data set. In this latter case, some bootstrap sets will contain no occurrences of a particular residue or nucleotide. In such cases, the value of the coefficient for that residue will be zero. Other bootstrap sets will contain at least some occurrences of the residue or nucleotide and give a non-zero value of the corresponding coefficient. But the sets giving a zero value will cause the standard deviation of the coefficient to become relatively large. This reduces the confidence in the coefficient value and results in a lower rank. But this is to be expected, given that there is relatively little data on the residue or nucleotide involved.

Next, at a block 739, the method ranks the regression coefficients (or other indicators) from lowest (best) p-value to highest (worst) p-value. This ranking correlates highly with the absolute value of the regression coefficients themselves, owing to the fact that the larger are the absolute value, the more standard deviations are removed from zero. Thus, for a given standard deviation, the p-value becomes smaller as the regression coefficient becomes larger. However, the absolute ranking will not always be the same with both p-value and pure magnitude methods, especially when relatively few data points are available to begin with in set S.

Finally, as shown at a block 741, the method fixes and toggles certain residues, based on the rankings observed in the operation of block 739. This is essentially the same use of rankings described above for other embodiments. In one approach, the method fixes the best residues (now those with the lowest p-values) and toggles the others (those with highest p-values).

This method 725 has been shown to perform well in silico. Moreover, in some embodiments, the p-value ranking approach naturally deals with single or few instance residues: the p-values will generally be higher (worse) because in the bootstrap process, those residues that did not appear often in the original data set will be less likely to get picked up at random. Even if their coefficients are large, their variability (measured in standard deviations) will be quite high as well. In some embodiments, this is the desired result, as those residues that are not well represented (i.e., either have not seen with sufficient frequency or have lower regression coefficients) may be good candidates for toggling in the next round of library design.

VI. Generating an Optimized Protein Variant Library by Modifying Model-Predicted Sequences One of the goals of the invention is to generate an optimized protein variant library through directed evolution. Some embodiments of the invention provide methods to guide directed evolution of protein variants using the generated sequence-activity models. The various sequence-activities models prepared and refined according to the methods described above are suitable to guide directed evolution of proteins or biological molecules. As part of the process, the methods may identify sequences that are to be used for generating a new protein variant library. Such sequences include variations on the defined residues identified above, or are precursors used to subsequently introduce such variations. The sequences may be modified by performing mutagenesis or a recombination-based diversity generation mechanism to generate the new library of protein variants. The new library may also be used in developing a new sequence-activity model.

In some embodiments, preparation of oligonucleotides or nucleic acid sequences is achieved by synthesizing the oligonucleotides or nucleic acid sequences using a nucleic acid synthesizer. Some embodiments of the invention include performing a round of directed evolution using the prepared oligonucleotides or protein sequence as building blocks for directed evolution. Various embodiments of the invention can apply recombination and/or mutagenesis to these building blocks to generate diversity.

As one specific example, some embodiments apply recombination techniques to oligonucleotides. In these embodiments, the methods involve selecting one or more mutations for a round of directed evolution by evaluating the coefficients of the terms of the sequence-activity model. Mutations are selected from combinations of defined amino acids or nucleotides of specific types at specific positions based on their contributions to the activity of proteins as predicted by the models. In some embodiments, selection of mutations involves identifying one or more coefficients that are determined to be larger than others of the coefficients, and selecting the defined amino acid or nucleotide at a defined position represented by the one or more coefficients so identified. In some embodiments, after selecting mutations according to the sequence-activity models, the methods involve preparing a plurality of oligonucleotides containing or encoding the one or more mutations, and performing a round of directed evolution using the oligonucleotides prepared. In some embodiments, the directed evolution techniques involve combining and/or recombining the oligonucleotides.

Other embodiments of the invention apply recombination techniques to protein sequences. In some embodiments, the methods involve identifying a new protein or a new nucleic acid sequence, and preparing and assaying the new protein or a protein encoded by the new nucleic acid sequence. In some embodiments, the methods further involve using the new protein or protein encoded by the new nucleic acid sequence as a starting point for further directed evolution. In some embodiments, the directed evolution process involves fragmenting and recombining the protein sequence that is predicted by the model to have a desired level of activity.

In some embodiments, the methods identify and/or prepare a new protein or a new nucleic acid sequence based on individual mutations that are predicted to be important by the model. These methods involve: selecting one or more mutations by evaluating the coefficients of the terms of the sequence-activity model to identify one or more of the defined amino acids or nucleotides at the defined positions that contribute to the activity; identifying a new protein or a new nucleic acid sequence comprising the one or more mutations selected above, and preparing and assaying the new protein or a protein encoded by the new nucleic acid sequence.

In other embodiments, the methods identify and/or prepare a new protein or a new nucleic acid sequence based on the predicted activity of a whole sequence instead of individual mutations. In some of these embodiments, the methods involve applying multiple protein sequences or multiple amino acid sequences to the sequence-activity model and determining activity values predicted by the sequence-activity model for each of the multiple protein sequences or nucleic acid sequences. The methods further involve selecting a new protein sequence or a new nucleic acid sequence from among the multiple protein sequences or multiple amino acid sequences applied above by evaluating the activity values predicted by the sequence-activity model for the multiple sequences. The methods also involve preparing and assaying a protein having the new protein sequence or a protein encoded by the new nucleic acid sequence.

In some embodiments, rather than simply synthesizing the single best-predicted protein, a combinatorial library of proteins is generated based on a sensitivity analysis of the best changes in the residue choices at each location in the protein. In this embodiment, the more sensitive a given residue choice is for the predicted protein, the greater the predicted fitness change will be. In some embodiments these sensitivities are from highest to lowest and the sensitivity scores are used to create combinatorial protein libraries in subsequent rounds (i.e., by incorporating those residues based on sensitivity). In some embodiment, in which a non-interaction model is used, the sensitivity is identified by simply considering the size of the coefficient associated with a given residue term in the model. However, this is not possible for interaction models. Instead, in embodiments utilizing interaction models, the residue sensitivity is determined by using the model to calculate changes in activity when a single residue is varied in the "best" predicted sequence.

Some embodiments of the invention include selecting one or more positions in the protein sequence or nucleic acid sequence and conducting saturation mutagenesis at the one or more positions so identified. In some embodiments, the positions are selected by evaluating the coefficients of the terms of the sequence-activity model to identify one or more of the defined amino acids or nucleotides at the defined positions that contribute to the activity. Accordingly, in some embodiments, a round of directed evolution includes performing saturation mutagenesis on a protein sequence at positions selected using the sequence-activity models. In some embodiments involving models comprising one or more interaction terms, the methods involve applying mutagenesis simultaneously at the two or more interacting residues.

In some embodiments, residues are taken into consideration in the order in which they are ranked. In some embodiments, for each residue under consideration, the process determines whether to "toggle" that residue. The term "toggling" refers to the introduction of multiple amino acid residue types into a specific position in the sequences of protein variants in the optimized library. For example, serine may appear in position 166 in one protein variant, whereas phenylalanine may appear in position 166 in another protein variant in the same library. Amino acid residues that do not vary between protein variant sequences in the training set typically remain fixed in the optimized library. However, this is not always the case, as there can be variation in the optimized libraries.

In some embodiments, an optimized protein variant library is designed such that all of the identified "high" ranking regression coefficient residues are fixed, and the remaining lower ranking regression coefficient residues are toggled. The rationale for this embodiment is that the local space surrounding the 'best' predicted protein should be searched. It is noted that the starting point "backbone" in which the toggles are introduced may be the best protein predicted by a model and/or an already validated 'best' protein from a screened library. Indeed, it is not intended that the starting point backbone be limited to any particular protein.

In an alternative embodiment, at least one or more, but not all of the identified high-ranking regression coefficient residues are fixed in the optimized library, and the others toggled. This approach is recommended in some embodiments, if there is a desire to not drastically change the context of the other amino acid residues by incorporating too many changes at one time. Again, the starting point for toggling may be the best set of residues as predicted by the model, a best validated protein from an existing library, or an "average" clone that models well. In the latter case, it may be desirable to toggle the residues predicted to be of higher importance, as a larger space should be explored in the search for activity hills previously omitted from the sampling. This type of library is typically more relevant in early rounds of library production, as it generates a more refined picture for subsequent rounds. It is also not intended that the starting point backbone be limited to any particular protein.

Some alternatives of the above embodiments involve different procedures for using residue importance (rankings) in determining which residues to toggle. In one such alternative embodiment, higher ranked residue positions are more aggressively favored for toggling. The information needed in this approach includes the sequence of a best protein from the training set, a PLS or PCR predicted best sequence, and a ranking of residues from the PLS or PCR model. The "best" protein is a wet-lab validated "best" clone in the dataset (i.e., the clone with the highest measured function that still models well in that it falls relatively close to the predicted value in cross validation). The method compares each residue from this protein with the corresponding residue from a "best predicted" sequence having the highest value of the desired activity. If the residue with the highest load or regression coefficient is not present in the 'best' clone, the method introduces that position as a toggle position for the subsequent library. If the residue is present in the best clone, the method does not treat the position as a toggle position, and it will move to the next position in succession. The process is repeated for various residues, moving through successively lower load values, until a library of sufficient size is generated.

In some embodiments, the number of regression coefficient residues to retain, and number of regression coefficient residues to toggle, are varied. The determination of which residues to toggle and which to retain is based on various factors including but not limited to the desired library size, the magnitude of difference between regression coefficients, and the degree to which nonlinearity is thought to exist. Retention of residues with small (neutral) coefficients may uncover important nonlinearities in subsequent rounds of evolution. In some embodiments, optimized protein variant libraries contain about $2^N$ protein variants, where N represents the number of positions that are toggled between two residues. Stated another way, the diversity added by each additional toggle doubles the size of the library such that 10 toggle positions produces~1,000 clones (1,024), 13 positions~10,000 clones (8,192) and 20 positions~1,000,000 clones (1,048,576). The appropriate library size depends on factors such as cost of screen, ruggedness of landscape, preferred percentage sampling of space, etc. In some cases, it has been found that a relatively large number of changed residues produce a library in which an inordinately large percentage of the clones are non-functional. Therefore, in some embodiments, the number of residues for toggling ranges from about 2 to about 30; i.e., the library size ranges from between about 4 and $2^{30}$~$10^9$ clones.

In addition, it is contemplated that various subsequent round library strategies be utilized simultaneously, with some strategies being more aggressive (fixing more "beneficial" residues) and other strategies being more conservative (fixing fewer "beneficial" residues with the goal of exploring the space more thoroughly).

In some embodiments, groups or residues or "motifs" that occur in most naturally occurring or otherwise successful peptides are identified and/or preserved, as they may be important in the functionality of the protein (e.g., activity, stability, etc.). For example, it may be found that Ile at variable position 3 is always coupled with Val at variable position 11 in naturally occurring peptides. Hence, in one embodiment, preservation of such groups is required in any toggling strategy. In other words, the only accepted toggles are those that preserve a particular grouping in the base protein or those that generate a different grouping that is also found in active proteins. In the latter case it is necessary to toggle two or more residues.

In some additional embodiments, a wet-lab validated 'best' (or one of the few best) protein in the current optimized library (i.e., a protein with the highest, or one of the few highest, measured function that still models well, i.e., falls relatively close to the predicted value in cross validation) serves as a backbone in which various changes are incorporated. In another approach, a wet-lab validated 'best' (or one of the few best) protein in the current library that may not model well serves as a backbone where various changes are incorporated. In some other approaches, a sequence predicted by the sequence-activity model to have the highest value (or one of the highest values) of the desired activity serves as the backbone. In these approaches, the dataset for the "next generation" library (and possibly a corresponding model) is obtained by changing residues in one or a few of the best proteins. In one embodiment, these changes comprise a systematic variation of the residues in the backbone. In some cases, the changes comprise various mutagenesis, recombination and/or subsequence selection techniques. Each of these may be performed in vitro, in vivo, and/or in silico. Indeed, it is not intended that the present invention be limited to any particular format, as any suitable format finds use.

In some embodiments, while the optimal sequence predicted by a non-interaction model can be identified by inspection as described above, the same is not true for interaction models. Certain residues appear in both non-interaction and interaction terms and their overall effect on activity in the context of many possible combinations of other residues can be problematic. Thus, as with selection of interaction terms for an interaction model, the optimal sequence predicted by an interaction model can be identified by testing all possible sequences with the model (assuming sufficient computational resources) or by utilizing a searching algorithm such as a stepwise algorithm.

In some embodiments, the information contained in the computer-evolved proteins identified as described above is used to synthesize novel proteins and test them on physical assays. An accurate in silico representation of the actual wet lab-determined fitness function, allows researchers to reduce the number of cycles of evolution and/or the number variants needed to be screened in the lab. In some embodiments, optimized protein variant libraries are generated using the recombination methods described herein, or alternatively, by gene synthesis methods, followed by in vivo or in vitro expression. In some embodiments, after the optimized protein variant libraries are screened for desired activity, they are sequenced. As indicated above in the discussion of FIGS. 1 and 2, the activity and sequence information from the optimized protein variant library can be employed to generate another sequence-activity model from which a further optimized library can be designed, using the methods described herein. In one embodiment, all of the proteins from this new library are used as part of the dataset.

VII. Digital Apparatus and Systems

As should be apparent, embodiments described herein employ processes acting under control of instructions and/or data stored in or transferred through one or more computer systems. Embodiments disclosed herein also relate to apparatus for performing these operations. In some embodiments, the apparatus is specially designed and/or constructed for the required purposes, or it may be a general-purpose computer selectively activated or reconfigured by a computer program and/or data structure stored in the computer. The processes provided by the present invention are not inherently related to any particular computer or other specific apparatus. In particular, various general-purpose machines find use with programs written in accordance with the teachings herein. However, in some embodiments, a specialized apparatus is constructed to perform the required method operations. One embodiment of a particular structure for a variety of these machines is described below.

In addition, certain embodiments of the present invention relate to computer readable media or computer program products that include program instructions and/or data (including data structures) for performing various computer-implemented operations. Examples of computer-readable media include, but are not limited to, magnetic media such as hard disks, floppy disks, magnetic tape; optical media such as CD-ROM devices and holographic devices; magneto-optical media; semiconductor memory devices; and hardware devices that are specially configured to store and perform program instructions, such as read-only memory devices (ROM) and random access memory (RAM), application-specific integrated circuits (ASICs), and programmable logic devices (PLDs). The data and program instructions may also be embodied on a carrier wave or other transport medium (e.g., optical lines, electrical lines, and/or airwaves). Indeed, it is not intended that the present invention be limited to any particular computer-readable media or any other computer program products that include instructions and/or data for performing computer-implemented operations.

Examples of program instructions include, but are not limited to low-level code such as produced by a compiler, and files containing higher level code that may be executed by the computer using an interpreter. Further, the program instructions include, but are not limited to machine code, source code and any other code that directly or indirectly controls operation of a computing machine in accordance with the present invention. The code may specify input, output, calculations, conditionals, branches, iterative loops, etc.

Figure 8:
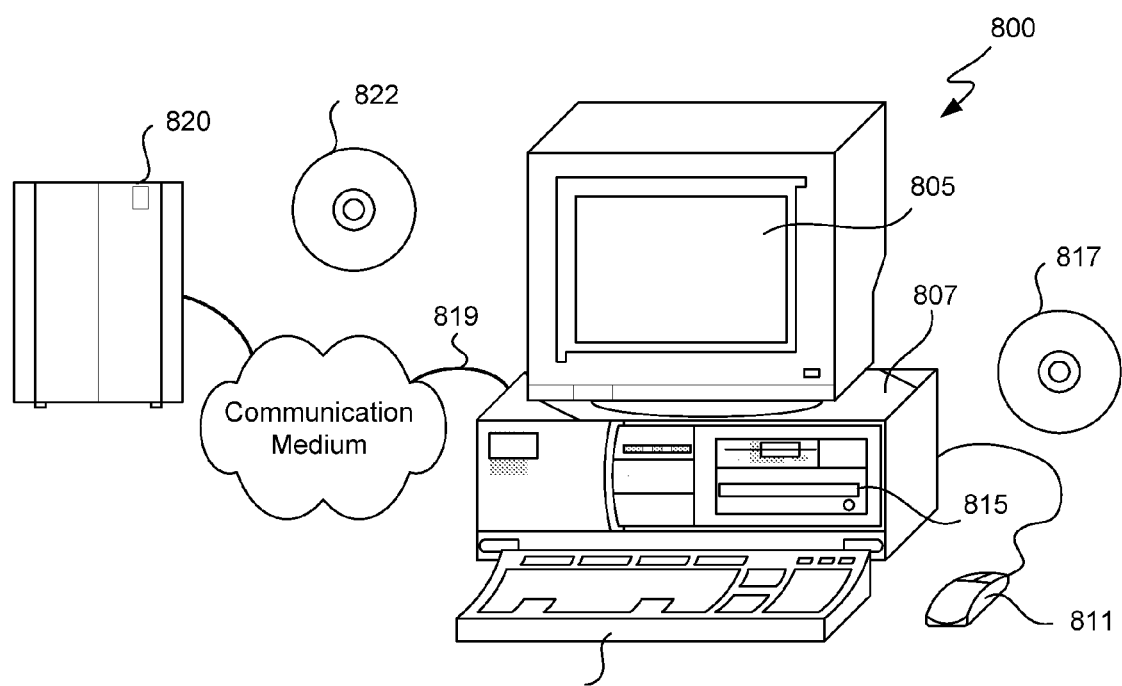
FIG. 8 is a schematic of an exemplary digital device.

In one illustrative example, code embodying methods disclosed herein are embodied in a fixed media or transmissible program component containing logic instructions and/or data that when loaded into an appropriately configured computing device causes the device to perform a simulated genetic operation (GO) on one or more character string(s). FIG. 8 shows an example digital device 800 that is a logical apparatus that can read instructions from media 817, network port 819, user input keyboard 809, user input 811, or other inputting means. Apparatus 800 can thereafter use those instructions to direct statistical operations in data space, e.g., to construct one or more data set (e.g., to determine a plurality of representative members of the data space). One type of logical apparatus that can embody disclosed embodiments is a computer system as in computer system 800 comprising CPU 807, optional user input devices keyboard 809, and GUI pointing device 811, as well as peripheral components such as disk drives 815 and monitor 805 (which displays GO modified character strings and provides for simplified selection of subsets of such character strings by a user. Fixed media 817 is optionally used to program the overall system and can include, e.g., a disk-type optical or magnetic media or other electronic memory storage element. Communication port 819 can be used to program the system and can represent any type of communication connection.

In some embodiments, the disclosure provides a computer system, comprising: one or more processors; system memory; and one or more computer-readable storage media having stored thereon computer-executable instructions that, when executed by the one or more processors, cause the computer system to implement a method for conducting directed evolution of biological molecules. The method comprising: (a) obtaining sequence and activity data for a plurality of biological molecules, each biological molecule comprising a sequence having subunits of various types and sequence positions; (b) building a sequence-activity model from the obtained data; and (c) using the sequence-activity model to identify one or more subunits of specific types at specific positions for variation to impact a desired activity of the biological molecules. In some embodiments, the sequence-activity model includes a product of a plurality of base multiplicative terms, each of the base multiplicative terms comprising (1) a dummy variable representing the presence/absence of a defined subunit of a specific type at a specific sequence position, and (2) a coefficient representing the defined subunit's contribution to activity;

Certain embodiments can also be embodied within the circuitry of an application specific integrated circuit (ASIC) or programmable logic device (PLD). In such a case, the embodiments are implemented in a computer readable descriptor language that can be used to create an ASIC or PLD. Some embodiments of the present invention are implemented within the circuitry or logic processors of a variety of other digital apparatus, such as PDAs, laptop computer systems, displays, image editing equipment, etc.

In some embodiments, the present invention relates to a computer program product comprising one or more computer-readable storage media having stored thereon computer-executable instructions that, when executed by one or more processors of a computer system, cause the computer system to implement a method for identifying biological molecules to affect a desired activity. Such method be any method described herein such as those encompassed by the Figures and pseudocode. In some embodiments, the method receives sequence and activity data for a plurality of biological molecules, and prepares a base model and an improved model from the sequence and activity data. In some embodiments, the model predicts activity as a function of the presence or absence of sub-units of the sequence.

In some embodiments of the present invention, the method implemented by the computer program product prepares at least one new model by adding/subtracting at least one new interaction term to/from the base model, wherein the new interaction term represents the interaction between two or more interacting sub-units. In some embodiments, the method determines the ability of at least one new model to predict activity as a function of the presence or absence of the sub-units. The method also determines whether to add/subtract the new interaction term to/from the base model based on the ability of at least one new model to predict activity as determined above and with a bias against including additional interaction terms.

VIII. Examples

The following examples show a process of directed evolution implementing various embodiments of the invention. The process involve creating a protein variant library, generating sequence-activity models of various forms based on variants of the library, and conducting directed evolution of proteins to achieve a desired level of protein activity of interest.

First, a combinatorial protein variant library was constructed, the protein variants having 11 mutations using Automated Parallel Splicing by Overlap Extension (SOEing), or APS technology. The library incorporates mutations randomly at a rate of about 3 mutations per variant. The 11 mutations of the protein variants are shown in the first 11 rows of Table VI.

TABLE VI

Coefficients Values for Linear Additive Model, Non-interaction Multiplicative and Interaction Multiplicative Models

| Mutations (position, nucleotide) | Additive Model Coefficients | Multiplicative Model Coefficients | Multiplicative & Interaction Model Coefficients |
|---|---|---|---|
| 1A | 0.33 | 0.48 | 0.35 |
| 1G | 0.28 | 0.49 | 0.53 |
| 2A | −0.63 | −0.43 | 0.1 |
| 2G | −0.92 | −0.67 | −0.35 |
| 3A | 0.035 | 0.13 | 0.037 |
| 4A | −0.32 | −0.06 | −0.17 |
| 5A | −1.5 | −0.86 | −0.84 |
| 6A | 0.50 | 1.3 | 1.4 |
| 6G | 0.58 | 1.15 | 0.95 |
| 7A | 0.22 | 0.42 | 0.84 |
| 8A | −1.6 | −0.88 | −0.83 |
| Intercept | 1.9 | — | — |
| 2A*7A | — | — | 0.89 |
| 2G*7A | — | — | 0.80 |
| 2A*3A | — | — | 0.28 |
| 2G*4A | — | — | 0.65 |

Then the process obtained the sequence/activity data for the library. The constructed variants were sequenced using a next-generation sequencing method with barcoding capability. The sequencing essay included 6×96 well plates, each plate containing 6 backbone positive control wells and 6 negative control wells. The essay also measured fitness or desired activity of the proteins. Fitness was recorded as a ratio relative to the positive control as a fold improvement over positive control (FIOP) measure.

The sequence/activity data obtained above was used to construct a data matrix representing the presence/absence of mutations. Each row of the data matrix represented a variant (sequence) for a total of nrows (179). First column of the matrix contained FIOP values representing the activity of the variants. All other columns contained values representing the presence/absence of a mutation.

The data matrix obtained is fit using a non-interaction additive base model as of the following form:

$$y = \beta + C_{1A}X_{1A} + G_{1G}X_{1G} + C_{2A}X_{2A} + C_{2G}X_{2G} + C_{3A}X_{3A} + C_{4A}X_{4A} + C_{5A}X_{5A} + C_{6A}X_{6A} + C_{6G}X_{6G} + C_{7A}X_{7A} + C_{8A}X_{8A}$$

where y is the activity predicted by the model, and β is the "intercept" of the linear equation.

A bootstrap technique using random sampling with replacement was applied to fit the model to the obtained data using the following procedure:

(a) Rows of data in the data matrix were sampled with replacement nrows (179) number of times.

(b) Sampled data were fit using ordinary least squares regression (c) Steps (a) and (b) were repeated 500 times.

(d) Coefficients from each of (c) were averaged to obtain the final model coefficient values.

(e) The model obtained from (d) was used to predict the FIOP value of the sequence data in the data matrix. The observed and predicted values were plotted together for each observation in FIG. 9A.

Figure 9A:
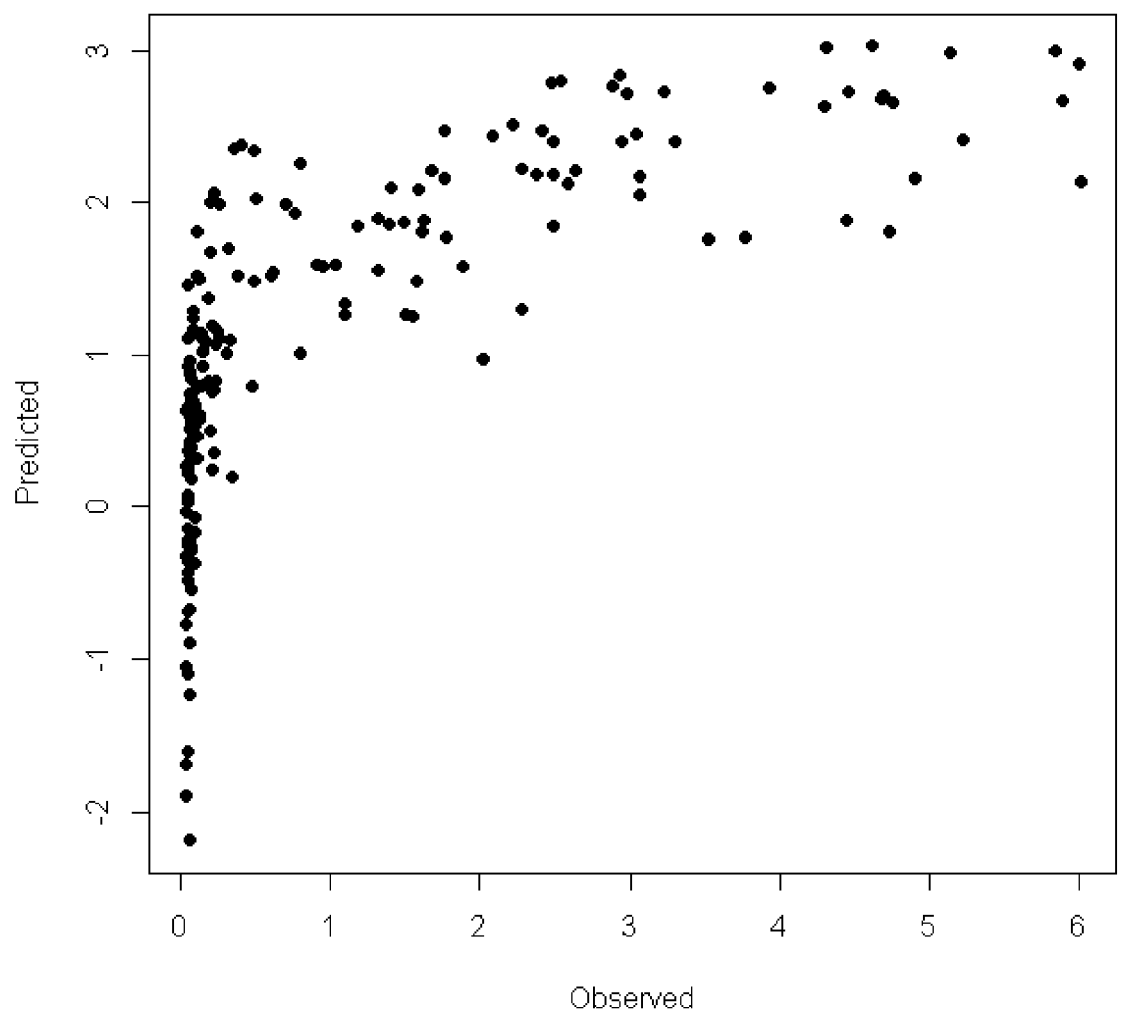
FIGS. 9A-C are graphs that respectively show the predictive power of a linear additive model, a non-interaction multiplicative model, and an interaction multiplicative model.

The values of the coefficients of this non-interaction additive model is shown in the second column of Table VI. As can be seen in FIG. 9A, the non-interaction additive model overestimates the activity levels for many observations, especially those that have low observed activity levels.

The second example used a multiplicative model to fit the same data. The model has the following form:

$$y = \beta \times (1 - C_{1A}X_{1A}) \times (1 - C_{1G}X_{1G}) \times (1 - C_{2A}X_{2A}) \times (1 - C_{2G}X_{2G}) \times (1 - C_{3A}X_{3A}) \times (1 - C_{4A}X_{4A}) \times (1 - C_{5A}X_{5A}) \times (1 - C_{6A}X_{6A}) \times (1 - C_{6G}X_{6G}) \times (1 - C_{7A}X_{7A}) \times (1 - C_{8A}X_{8A})$$

Alternatively, a model can take on the following form if the coefficient values are set to effectively incorporate the constant 1 into calculation of the y value. For instance, if the coefficients for the above model are set to span the range of −0.9 to 1.5, then the coefficients can be set to span the range of 0.1 to 2.5 for the following alternative model to achieve similar model output:

$$y = \beta \times C_{1A}X_{1A} \times C_{1G}X_{1G} \times C_{2A}X_{2A} \times C_{2G}X_{2G} \times C_{3A}X_{3A} \times C_{4A}X_{4A} \times C_{5A}X_{5A} \times C_{6A}X_{6A} \times C_{6G}X_{6G} \times C_{7A}X_{7A} \times C_{8A}X_{8A}$$

The model was refined by adjusting the coefficient values using both bootstrapping and genetic algorithm techniques. The model fitting was performed by minimizing the mean squared error of predicted activity (or fitness) relative to observation as follows:

(a) Sequence/activity data of rows were sampled with replacement for nrows number to provide bootstrapping data.

(b) The model was fitted to sampled data using a genetic algorithm, which restricted the coefficient values to be between −0.9 and 1.5. The genetic algorithm had a population size of 200, and it ran for 100 generations.

(c) Steps (a) and (b) were repeated for 500 times.

(d) The top 10 chromosomes/individuals from each of (c) are averaged to obtain the final model coefficients.

(e) For each row of the data matrix, (d) is used to predict the FIOP value. Observed and predicted values were plotted together for each row of data (an observation) in FIG. 9B. The coefficient values of this multiplicative base model are shown in the third column of Table VI.

Figure 9B:
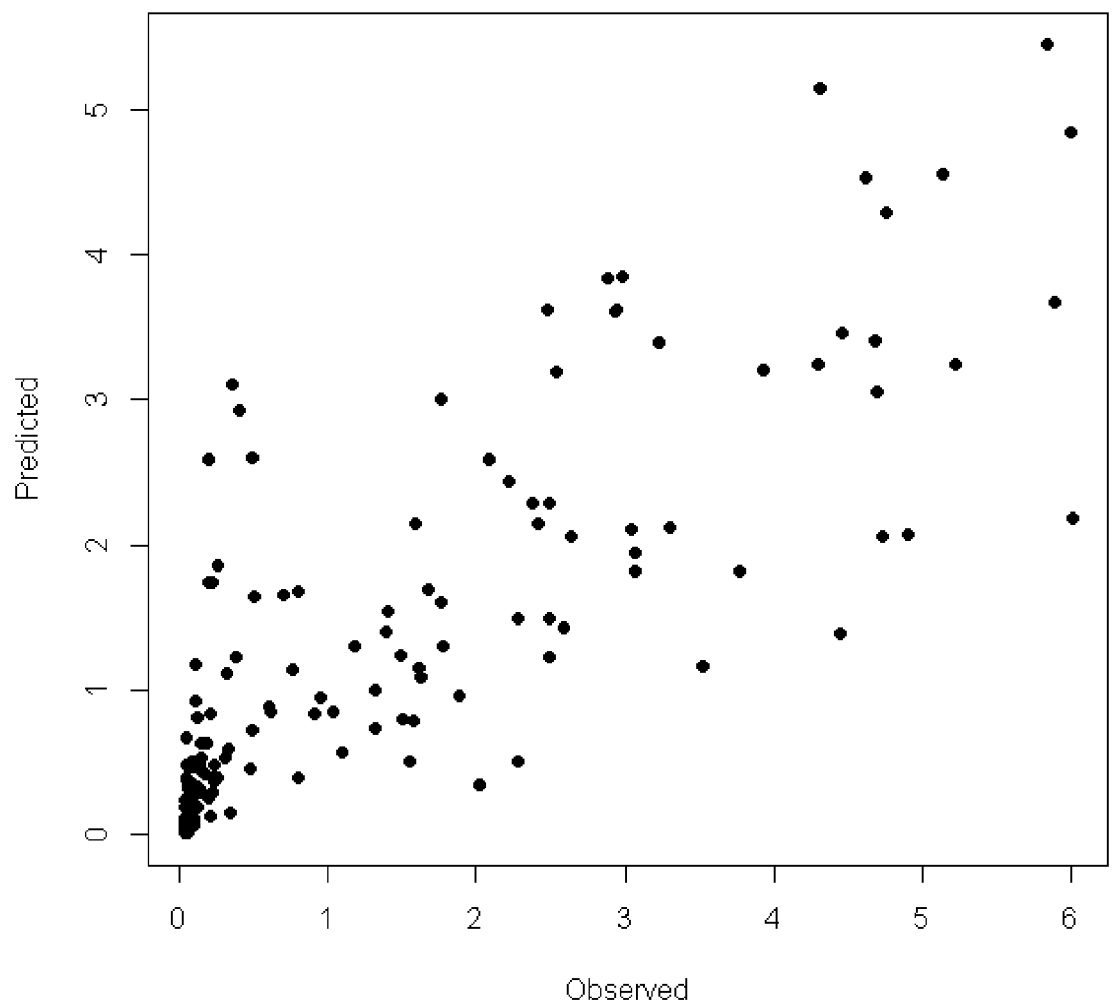

As can be seen in FIG. 9B, this non-interaction multiplicative model has predictions that better match the observed activity values of the variant library, such that it does not have significant, consistent overestimates for protein variants having low observed activity levels. However, the residual errors are still relatively large, with data points scattered away from the diagonal line of the plot.

The next example demonstrates a multiplicative base model refined using a stepwise method to identify appropriate interaction terms, forming an interaction multiplicative model. This procedure started to refine the multiplicative model from a the multiplicative base model outlined in the previous example with the following steps.

(a) The base model obtained above was set as the best model.

(b) All possible pairwise interaction coefficients were placed into a pool of coefficients. (1A*2A, 1A*3A, 1A*4A, . . . , 6G*8A, 7A*8A)

(c) Each coefficient was added to the best model, which was fitted using a genetic algorithm having the same parameters as described in the previous example.

(d) The fitness of each new model was obtained from (c) using AIC.

(e) The model with the lowest AIC (i.e. the fittest model) from (d) was set to be the best of model of the current round.

(f) If the model from (e) was better than the best model, the best model was set to this model, and the coefficient in this model was removed from the coefficient pool, and the algorithm goes to (c)—otherwise, there were no new models and the algorithm is completed.

(g) The new model from (f) is fit using the bootstrapping/fitting method outlined in the preceding example.

The values of the coefficient for this interaction multiplicative model are shown in the fourth column of Table VI, where the last 4 coefficients are for interaction terms. As can be seen in the table across the three columns of coefficient values, the relative magnitudes of the coefficients within a model maintained a similar pattern, suggesting the correct convergence of the optimization procedures for all the models.

Figure 9C:
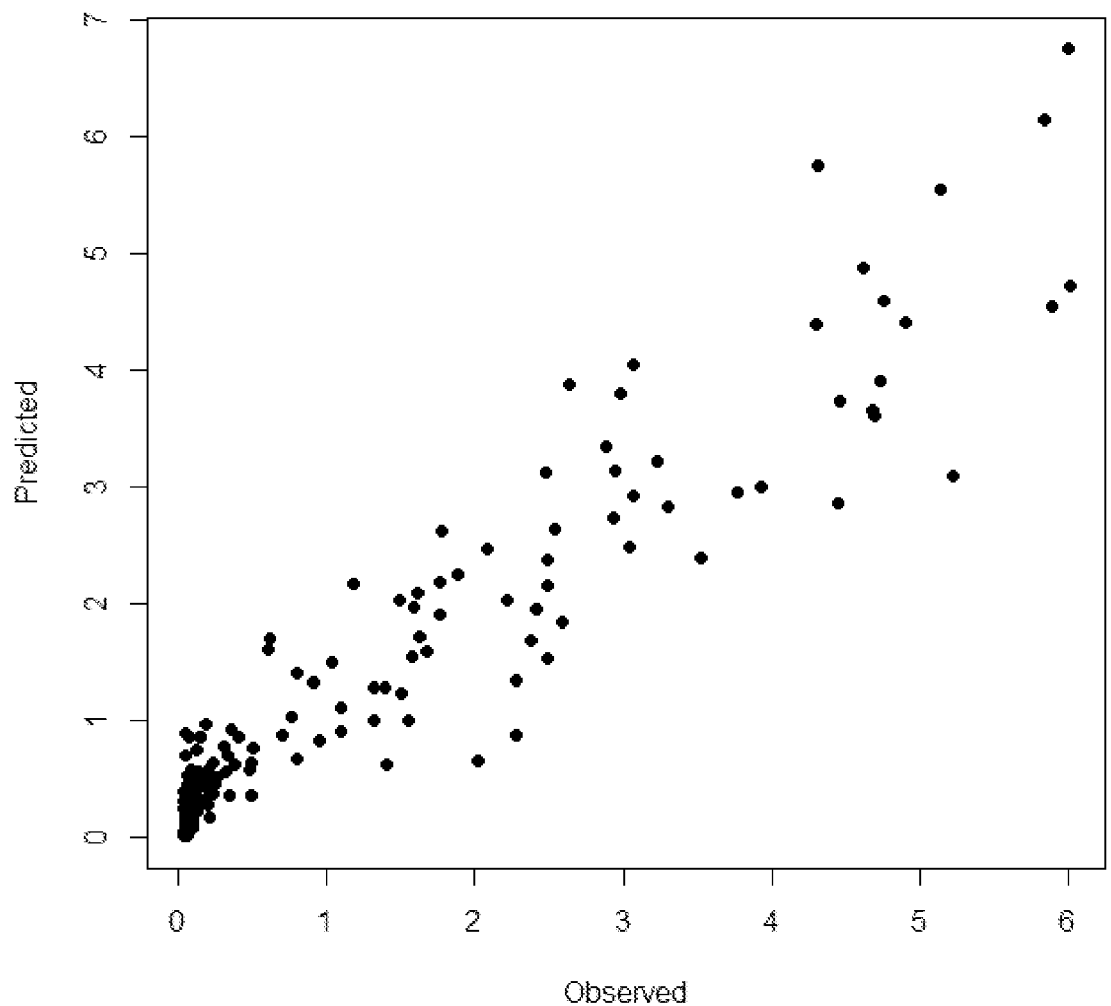

FIG. 9C plots the activity of the protein variants as predicted by the interaction multiplicative model versus the observed activity levels of the protein variants. Here, the interaction multiplicative model does the best in predicting the activities of the observations among the three models. The residual errors are consistently small through the whole range of activity levels, with the data points distributed near the diagonal line.

The next examples show how the interaction multiplicative model obtained above was used to guide directed evolution of protein variants to achieve the desired protein activity.

One example uses mutations that already exist in the current library. In this example, activity of all plausible combinations of mutations was predicted using the interaction multiplicative model obtained above. Then sequences for all possible variants were constructed in silico, and their activities (FIOPs) were calculated using the interaction multiplicative model. The predicted FIOPs were ordered from highest to lowest, and listed in Table VII.

The top 5 predictions are shown below, along with their predicted values and observed values (if available). The unobserved variants were synthesized and re-tested, and compared together with the observed variants. The best performing variant in retest was carried forward to create a new backbone for evolution.

TABLE VII

The fittest sequences predicted by an interaction multiplicative model.

| Predicted | Observed | Mutations |
|---|---|---|
| 7 | NA | 1G, 3A, 6A, 7A |
| 6.7 | 5.99 | 1G, 6A, 7A |
| 6.2 | 5.8 | 1A, 3A, 6A, 7A |
| 5.9 | NA | 1A, 6A. 7A |
| 5.8 | NA | 1G, 3A, 4A, 6A, 7A |

In this example of directed evolution, deleterious mutations and combination of mutations were recorded, and were excluded from immediate rounds of evolution. Furthermore, beneficial diversity identified but not included in the next round backbone was recombined together with (if available) previously identified beneficial diversity in a combinatorial fashion.

Another example of directed evolution generated new diversity using mutagenesis diversity mechanisms. The sequence space was search by generating diversity through saturated mutagenesis in a combinatorial fashion at positions that were identified by the interaction multiplicative model as having significant interacting effects on the activity of interest. These positions are those having high values of interaction coefficients: in this case, positions 2, 3, 4, and 7. Saturation mutagenesis was performed on these positions simultaneously. Resulting libraries were screened for activity relative to the backbone, which helped to identify better performing variants.

While the foregoing has been described in some detail for purposes of clarity and understanding, it will be clear to one skilled in the art from a reading of this disclosure that various changes in form and detail can be made without departing from the true scope of the disclosure. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of conducting directed evolution of one or more polypeptide or polynucleotide molecules, the method comprising, (a) receiving sequence data of a plurality of polypeptide molecules or a plurality of polynucleotide molecules encoding the plurality of polypeptide molecules, wherein the sequence data comprises identities and positions of a plurality of amino acids for each molecule of the plurality of polypeptide molecules or a plurality of nucleotides for each molecule of the plurality of polynucleotide molecules;

(b) receiving activity data of the plurality of polypeptide molecules;

(c) fitting a sequence-activity model to the received sequence data and the received activity data, wherein
the sequence-activity model receives as one or more inputs one or more amino acids of a polypeptide molecule or one or more nucleotides of a polynucleotide molecule encoding the polypeptide molecule,
the sequence-activity model provides as an output an activity of the polypeptide molecule,
the sequence-activity model has a form comprising a product of a plurality of terms, and
each of two or more of the plurality of terms comprises an independent variable representing at least one amino acid or at least one nucleotide at a sequence position and a coefficient representing a contribution to the activity by the at least one amino acid or the at least one nucleotide at the sequence position;

(d) determining one or more amino acid sequences or one or more nucleic acid sequences using the sequence-activity model;

(e) synthesizing one or more amino acid molecules or one or more nucleic acid molecules based on the one or more amino acid sequences or one or more nucleic acid sequences; and (f) recombining or performing mutagenesis on the one or more amino acid molecules or one or more nucleic acid molecules to provide the one or more polypeptide or polynucleotide molecules.

2. The method of claim 1, wherein (d) comprises:
selecting one or more mutations for a round of directed evolution by evaluating the coefficients of the two or more of the plurality of terms of the sequence-activity model to identify one or more defined amino acids or nucleotides at defined sequence positions that contribute to the activity; and
determining a plurality of oligonucleotides containing or encoding the one or more mutations, wherein the plurality of oligonucleotides comprise at least portions of the one or more nucleic acid sequences.

3. The method of claim 2, wherein selecting mutations for a round of directed evolution comprises identifying one or more coefficients that are determined to be larger than others of the coefficients, and selecting the defined amino acid or nucleotide at a defined position represented by the one or more coefficients so identified.

4. The method of claim 2, wherein the recombining in (f) comprises shuffling a plurality of oligonucleotides containing or encoding the one or more mutations.

5. The method of claim 2, further comprises synthesizing the plurality of oligonucleotides using a nucleic acid synthesizer.

6. The method of claim 2, wherein the one or more mutations are located at the defined sequence positions or associated with the one or more defined amino acids or nucleotides.

7. The method of claim 1, wherein (f) comprises fragmenting and recombining a polynucleotide molecule encoding a polypeptide molecule that is predicted by the sequence-activity model to have a desired level of activity.

8. The method of claim 1, wherein (f) comprises performing saturation mutagenesis on a polypeptide molecule that is predicted by the model to have a desired level of activity.

9. The method of claim 1, wherein (d) comprises:
selecting one or more mutations by evaluating the coefficients of the two or more of the plurality of terms of the sequence-activity model to identify one or more defined amino acids or nucleotides at defined sequence positions that contribute to the activity; and
identifying a new protein or a new nucleic acid sequence comprising the one or more mutations.

10. The method of claim 9, further comprising using the new protein or new nucleic acid sequence as a starting point for further directed evolution.

11. The method of claim 9, further comprising conducting saturation mutagenesis at one or more positions of the selected mutations.

12. The method of claim 1, wherein (d) comprises:
selecting one or more positions in an amino acid sequence or nucleic acid sequence by evaluating the coefficients of the two or more of the plurality of terms of the sequence-activity model to identify one or more defined amino acids or nucleotides at the one or more positions that contribute to the activity; and
conducting saturation mutagenesis at the one or more positions.

13. The method of claim 1, wherein (d) comprises:
applying multiple protein sequences or multiple amino acid sequences to the sequence-activity model and determining activity values predicted by the sequence-activity model for each of the multiple protein sequences or nucleic acid sequences; and
selecting a new protein sequence or a new nucleic acid sequence from among the multiple protein sequences or multiple amino acid sequences by evaluating the activity values predicted by the sequence-activity model for the multiple sequences;
and wherein (e) comprises:
preparing and assaying a protein having the new protein sequence or a protein encoded by the new nucleic acid sequence.

14. The method of claim 13, wherein preparing the protein having the new protein sequence or the protein encoded by the new nucleic acid sequence comprises synthesizing a new protein molecule or a new nucleic acid molecule corresponding to the new protein sequence or the new nucleic acid sequence.

15. The method of claim 1, wherein each of the two or more of the plurality of terms comprises a product of the coefficient and the independent variable, wherein the independent variable represents the presence or absence of the at least one amino acid or the at least one nucleotide at the sequence position.

16. The method of claim 15, wherein each of the two or more of the plurality of terms are provided in the form of (1+coefficient×independent variable).

17. The method of claim 15, wherein the at least one amino acid or the at least one nucleotide at the sequence position is one amino acid or one nucleotide at the sequence position.

18. The method of claim 17, wherein the independent variable is a dummy variable with value 0 representing the absence of the amino acid or the nucleotide at the sequence position, and value 1 representing the presence of the amino acid or the nucleotide at the sequence position.

19. The method of claim 15, wherein the at least one amino acid or the at least one nucleotide at the sequence position comprises two amino acids or two nucleotides at the sequence position alternatively.

20. The method of claim 19, wherein the independent variable is a dummy variable with value −1 representing the presence of one of the two amino acids or one of the two nucleotides, and value 1 representing the presence of another of the two amino acids or another of the two nucleotides.

21. The method of claim 1, wherein the coefficients are provided in a look-up table.

22. The method of claim 1, further comprising forming a protein variant library using the one or more polypeptide or a polynucleotide molecules provided by operation (f).

23. The method of claim 22, further comprising assaying for activity and sequencing members of the protein variant library.

24. The method of claim 23, further comprising using activity and sequence information for the protein variant library to generate and use a new sequence-activity model by performing operations (c)-(f) on the activity and sequence information for the protein variant library.

25. The method of claim 1, wherein at least one of the two or more of the plurality of terms comprises an interaction coefficient representing the contribution to activity of a defined combination of (i) a first amino acid or nucleotide at a first sequence position, and (ii) a second amino acid or nucleotide at a second sequence position, and
wherein the interaction coefficient represents the contribution to activity of said defined combination.

26. The method of any of claim 25, wherein the sequence-activity model is generated by a stepwise addition or subtraction of terms comprising interaction coefficients.

27. The method of claim 25, wherein the sequence-activity model is generated by using a genetic algorithm to select one or more terms comprising interaction coefficients.

28. The method of claim 1, wherein the sequence-activity model is generated by using a genetic algorithm to refine values of the coefficients.

29. The method of claim 27 or 28, wherein the sequence-activity model is generated by:
(i) preparing a generation of models each comprising a product of multiple terms and a dependent variable as recited in (c);

(ii) using each of the models in the generation of models to predict activity of at least some of the plurality of polypeptide molecules using sequences of the polypeptide molecules;
(iii) selecting one or more models from the generation of models based on the models' ability to accurately predict activity of the plurality of polypeptide molecules;
(iv) modifying the selected one or more models to produce a next generation of models; and
(v) repeating (ii) through (iv) with the a next generation of models multiple times to generate the sequence-activity model of (c).

30. The method of claim 1, the sequence-activity model is generated using prior information to determine posterior probability distributions of the model.

31. The method of claim 1, further comprising providing two or more sequence-activity models, each having the form recited in (c).

32. The method of claim 31, further comprising generating an ensemble model including terms from the two or more sequence-activity models, wherein the terms of the ensemble model are weighted by abilities of the two or more sequence-activity models to predict activity.

33. The method of claim 32, further comprising using the ensemble model to select mutations for a round of directed evolution.

34. A method of conducting directed evolution of biological molecules, the method comprising,
(a) obtaining sequence and activity data for a plurality of biological molecules, each biological molecule comprising a sequence having subunits of various types and sequence positions;
(b) fitting a sequence-activity model to the obtained sequence and activity data, wherein
 the sequence-activity model receives as inputs a plurality of subunits of a biological molecule,
 the sequence-activity model predicts an activity of the biological molecule as a function of types and sequence positions of the plurality of subunits of the biological molecule,
 the sequence-activity model comprises a product of a plurality of base multiplicative terms, each of the base multiplicative terms comprising (1) a dummy variable representing the presence or absence of at least one defined subunit at a specific sequence position, and (2) a coefficient representing the at least one defined subunit's contribution to activity;
(c) determining one or more biological molecules using the sequence-activity model;
(d) synthesizing the one or more biological molecules; and
(e) recombining or performing mutagenesis on the one or more biological molecules.

35. The method of claim 34, wherein the sequence is a whole genome, whole chromosome, chromosome segment, a collection of gene sequences for interacting genes, gene, protein, or polysaccharide, or any combination thereof.

36. The method of claim 34, wherein each subunit is selected from the group consisting of: a chromosome, chromosome segment, haplotype, gene, codon, mutation, nucleotide, amino acid, monosaccharide, lipid, or any combination thereof.

37. A computer system, comprising:
one or more processors;
system memory; and
one or more computer-readable storage media having stored thereon computer-executable instructions that, when executed by the one or more processors, cause the computer system to implement a method for conducting directed evolution of biological molecules, the method comprising:
(a) obtaining sequence and activity data for a plurality of biological molecules, each biological molecule comprising a sequence having subunits of various types and sequence positions;
(b) fitting a sequence-activity model to the obtained sequence and activity data, wherein
 the sequence-activity model receives as inputs a plurality of subunits of a biological molecule,
 the sequence-activity model predicts an activity of the biological molecule as a function of types and sequence positions of the plurality of subunits of the biological molecule,
 the sequence-activity model comprises a product of a plurality of base multiplicative terms, each of the base multiplicative terms comprising (1) a dummy variable representing the presence or absence of at least one defined subunit at a specific sequence position, and (2) a coefficient representing the at least one defined subunit's contribution to activity;
(c) determining one or more biological molecules using the sequence-activity model;
(d) synthesizing the one or more biological molecules; and
(e) recombining or performing mutagenesis on the one or more biological molecules.

* * * * *